United States Patent
Tazi et al.

(10) Patent No.: US 10,017,498 B2
(45) Date of Patent: *Jul. 10, 2018

(54) COMPOUNDS USEFUL FOR TREATING AIDS

(71) Applicants: ABIVAX, Paris (FR); CENTRE NATIONALE DE RECHERCHE SCIENTIFIQUE, Paris (FR); INSTITUT CURIE, Paris (FR); UNIVERSITE MONTPELLIER 2, Montpellier (FR)

(72) Inventors: Jamal Tazi, Clapiers (FR); Florence Mahuteau, Saint Remy les Chevreuses (FR); Romain Najman, L'Hay-les-Roses (FR); Didier Scherrer, Castelnau le Lez (FR); Noelie Campos, Le Cres (FR); Aude Garcel, Le Cres (FR)

(73) Assignees: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/789,250

(22) Filed: Jul. 1, 2015

(65) Prior Publication Data
US 2015/0307478 A1 Oct. 29, 2015

Related U.S. Application Data

(63) Continuation of application No. 13/377,760, filed as application No. PCT/IB2010/052651 on Jun. 14, 2010, now Pat. No. 9,145,367.

(30) Foreign Application Priority Data

Jun. 12, 2009 (EP) .................................... 09162630
Jun. 12, 2009 (EP) .................................... 09305540

(51) Int. Cl.
| | | |
|---|---|---|
| C07D 403/12 | (2006.01) |
| A61K 31/4709 | (2006.01) |
| A61K 31/4985 | (2006.01) |
| C07D 213/74 | (2006.01) |
| C07D 215/38 | (2006.01) |
| C07D 241/44 | (2006.01) |
| C07D 401/12 | (2006.01) |
| C07D 215/42 | (2006.01) |
| C07D 215/46 | (2006.01) |

(52) U.S. Cl.
CPC ........ *C07D 403/12* (2013.01); *A61K 31/4709* (2013.01); *A61K 31/4985* (2013.01); *C07D 213/74* (2013.01); *C07D 215/38* (2013.01); *C07D 215/42* (2013.01); *C07D 215/46* (2013.01); *C07D 241/44* (2013.01); *C07D 401/12* (2013.01)

(58) Field of Classification Search
CPC ........................... C07D 215/38; A61K 31/4709
See application file for complete search history.

(56) References Cited

U.S. PATENT DOCUMENTS 2,605,182 A * 7/1952 Peterson .................. G03C 1/54
430/146
7,019,147 B1 3/2006 Barth et al.
(Continued)

FOREIGN PATENT DOCUMENTS

DE 958 647 C 2/1957
EP 0 394 112 A2 10/1990
(Continued)

OTHER PUBLICATIONS

Molina et al., J. Org. Chem. 57, 929-39 (1992).*
Desai et al., Asian. J. Chem. 10, 993-94 (1998).*
Desai et al., Asian. J. Chem. 10, 370-72 (1998).*
Gordon et al., "Hutchinson-Gilford Progeria Syndrome," NCBI Bookshelf, 2003, accessed Http://www.ncbi.nlm.gov/books/NBK1121/on Jan. 26, 2016, 21 pages.
Feb. 16, 2016 Office Action Issued in U.S. Appl. No. 13/377,753.
Mar. 25, 2016 US Office Action issued in U.S. Appl. No. 14/256,334.
Park et al., "Efficient Palladium-Catalyzed Amination of Aryl Chlorides Using Dicyclo-hexylamino[(2,6- dimethyl) morpholino]phenylphosphine as a PN2 Ligand," Synthesis, 2009, No. 5, pp. 0815-0823.
(Continued)

*Primary Examiner* — Theodore R. West
(74) *Attorney, Agent, or Firm* — Oliff PLC

(57) ABSTRACT

A compound having the following formula or a pharmaceutically acceptable salt thereof:

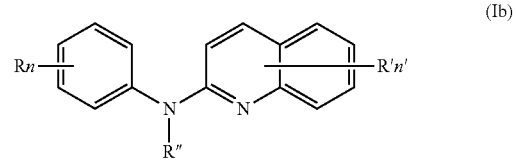

(Ib)

where:
R independently represents a hydrogen atom, a halogen atom, a ($C_1$-$C_3$)alkyl group, a —$NR_1R_2$ group, a ($C_1$-$C_3$)fluoroalkoxy group, a —$NO_2$ group, a phenoxy group, or a ($C_1$-$C_4$)alkoxy group,
$R_1$ and $R_2$ are independently a hydrogen atom or a ($C_1$-$C_3$)alkyl group,
R' is a hydrogen atom, a halogen atom, a ($C_1$-$C_3$)alkyl group, or a ($C_1$-$C_4$)alkoxy group,
R" is a hydrogen atom or a ($C_1$-$C_4$)alkyl group,
n is 1, 2, or 3, and
n' is 1 or 2.

18 Claims, No Drawings

Related U.S. Application Data

(60) Provisional application No. 61/186,552, filed on Jun. 12, 2009, provisional application No. 61/186,544, filed on Jun. 12, 2009.

(56) References Cited

U.S. PATENT DOCUMENTS

| | | | |
|---|---|---|---|
| 9,061,999 | B2 | 6/2015 | Tazi et al. |
| 9,108,919 | B2 | 8/2015 | Roux et al. |
| 9,145,367 | B2 * | 9/2015 | Tazi .................... C07D 213/74 |
| 9,637,475 | B2 | 5/2017 | Roux et al. |
| 2003/0207886 | A1 | 11/2003 | Plucker et al. |
| 2004/0038969 | A1 | 2/2004 | Doherty et al. |
| 2005/0119225 | A1 | 6/2005 | Schumacher et al. |
| 2006/0089380 | A1 | 4/2006 | Barnham et al. |
| 2008/0161353 | A1 | 7/2008 | Barnham et al. |
| 2011/0003843 | A1 | 1/2011 | Lejeune et al. |

FOREIGN PATENT DOCUMENTS

| | | | |
|---|---|---|---|
| EP | 2 266 972 A1 | 12/2010 | |
| EP | 2 465 502 A1 | 6/2012 | |
| EP | 2 757 161 A1 | 7/2014 | |
| FR | 2 387 229 A1 | 11/1978 | |
| FR | 2 436 786 A1 | 4/1980 | |
| FR | 2 627 493 A1 | 8/1989 | |
| FR | 2 645 861 A1 | 10/1990 | |
| FR | 2 859 474 A1 | 3/2005 | |
| FR | 2 859 475 A1 | 3/2005 | |
| GB | 585362 A * | 2/1947 | ........... C07D 215/38 |
| JP | H09-508642 A | 9/1997 | |
| JP | 2005-507365 A | 3/2005 | |
| WO | 95-21613 A1 | 8/1995 | |
| WO | 00/59875 A2 | 10/2000 | |
| WO | 02/074726 A2 | 9/2002 | |
| WO | 2004/007461 A1 | 1/2004 | |
| WO | 2004/078731 A1 | 9/2004 | |
| WO | 2005/023255 A2 | 3/2005 | |
| WO | 2005/051302 A2 | 6/2005 | |
| WO | 2006/081444 A2 | 8/2006 | |
| WO | 2008/003864 A1 | 1/2008 | |
| WO | 2008/008234 A1 | 1/2008 | |
| WO | 2008/089459 A1 | 7/2008 | |
| WO | 2008/101935 A2 | 8/2008 | |
| WO | 2008/115870 A2 | 9/2008 | |
| WO | 2008/143440 A1 | 11/2008 | |
| WO | 2009/023844 A2 | 2/2009 | |
| WO | WO 2009029617 A1 * | 3/2009 | ........... C07D 495/04 |
| WO | 2009/087238 A2 | 7/2009 | |
| WO | 2010/143168 A2 | 12/2010 | |
| WO | 2010/143169 A2 | 12/2010 | |
| WO | 2010/143170 A2 | 12/2010 | |
| WO | 2010/151755 A2 | 12/2010 | |
| WO | 2012/080953 A1 | 6/2012 | |
| WO | 2014/055944 A1 | 4/2014 | |

OTHER PUBLICATIONS

Loones et al., "Examination of the Mechanism of the Intramolecular Amination of N-(3-bromopyridin- 2-yl)azaheteroarylamines and N-(2-chloropyridin-3-yl)azaheteroarylamines: a Pd-catalyzed Amination and/or a Base-Assisted Nucleophilic Aromatic Substitution?," Tetrahedron, 2007, vol. 63, pp. 3818-3825.
Dhanabal et al., "Heteroatom Directed Photoannulation: Synthesis of Indoloquinoline Alkaloids: Cryptolepine, Cryptotackieine, Cryptosanguinolentine, and their Methyl Derivatives," Tetrahedron, 2006, vol. 62, pp. 6258-6263.
Boganyi et al.,"Syntheses of New Quinoline-Containing Heterocyclic Scaffolds Using Inter- and Intramolecular Pd-Catalyzed Amination," Journal of Heterocyclic Chemistry, 2009, vol. 46, No. 1, pp. 33-38.
Fors et al., "An Efficient Process for Pd-Catalyzed C—N Cross-Coupling Reactions of Aryl Iodides: Insight Into Controlling Factors," Journal of the American Chemical Society, 2009, vol. 131, No. 16, 5766-5768.
Jonckers et al., "Selective Palladium-Catalyzed Aminations of Dicholoropyridines," Tetrahedron, 2001, vol. 57, pp. 7027-7034.
Kaczmarek et al., "Synthesis and Antineoplastic Properties of Some Benzoiso-.Alpha.-Carbolines," Archiv Der Pharmazie, Weinheim, Germany, 1988, vol. 321, No. 8, pp. 463-467.
Loones et al., "Synthesis of Pyrido[2', 1':2,3]imidazo[4,5-b]quinoline and pyrido[1',2':1,2]imidazo [4,5b]quinoline and their Benzo and Aza Analogs via Tandem Catalysis," Tetrahedron, 2007, vol. 63, pp. 8954-8961.
Solekhova et al., "Reductive Amination of Quinoline N-Oxide with Aminopyridines and their N-Tosyl Derivatives," Russian Journal of Organic Chemistry, 2002, vol. 38, No. 8, pp. 1192-1194.
Nguyen et al., "Synthesis and Biological Evaluation of Amino-Substituted Benzo [f]pyrido[4,3-b] and Pyrido [3,4-b] quinoxalines: a New Class of Antineoplastic Agents," Anti-Cancer Drug Design, 1995, vol. 10, No. 4, 277-97.
Baklanov et al., "Photocyclization of (o-haloaryl)hetarylamines," Zhurnal Organicheskoi Khimii, 1991, vol. 27, No. 3, pp. 638-649.
Ducrocq et al., "Synthesis of 10-substituted 5H-pyrido[3', 4':4,5]pyrrolo[2,3-]isoquinolines," Journal of the Chemical Society, Perkin Transactions 1: Organic and Bio-Organic Chemistry (1972-1999), 1979, vol. 1, pp. 142-145.
Prostakov et al., "Schiff Bases in Syntheses of Substituted Naphthylamines, Napthyridines, Azophenanthrenes, and Benzocarbazole," Khimiya Geterotsiklicheskikh Soedinenii, 1972, vol. 10, pp. 1400-1403.
Grout et al., "Polyazabenzo[a]pyrenes," Journal of the Chemical Society [Section] C: Organic, 1968, vol. 21, pp. 2689-2693.
Talik et al., "2-Chloro-3, 5-dinitropyridine. I. Exchange Reactions of the Chlorine Atom," Bulletin de L'Academie Polonaise des Sciences, Serie Des Sciences Chimiques, 1960, vol. 8, No. 5, pp. 219-222.
Deuerleine, "Dipryridyl-, diquinolyl-, and Pyridylquinolylamines," Journal fuer Praktische Chemie (Liepzig), 1923, vol. 106, pp. 53-65.
Kondratenko et al., "Bactericidal Activity of Some Derivatives of N-heteroaromatic Compounds," Mikrobiologichnii Zhurnal, 1934-1977, 1978, vol. 40, No. 3, pp. 368-370.
Gritsenko et al., "Synthesis in Phenothiazines. XXXIX. Dimethylpyridophenothiazines," Khimiya Geterotsiklicheskikh Soedinenii, 1975, vol. 1, pp. 50-54.
Buchmann et al., "The Preparation and Reactivity of 4-hydroxy-7-chloroquinaldine," Journal fuer Praktische Chemie, 1962, vol. 17, pp. 135-146.
Khalifa, "Hutchinson-Gilford Progeria Syndrome: Report of a Libyan Family and Evidence of Autosomal Recessive Inheritance," Clinical Genetics, 1989, vol. 35, pp. 125-132.
Pendas et al., "Defective Prelamin A Processing and Muscular and Adipocyte Alterations in Zmpste24 Metalloproteinase-deficient Mice," Nature Genetics, 2002, vol. 31, pp. 94-99.
De Sandre-Giovannoli et al., "Altered Splicing in Prelamin A-associated Premature Aging Phenotypes," Progress in Molecular and Subcellular Biology, 2006, pp. 199-232.
Fong et al., "A Protein Farnesyltransferase Inhibitor Ameliorates Disease in a Mouse Model of Progeria," Science, 2006, vol. 311, pp. 1621-1623.
Varela et al., "Combined Treatment with Statins and Aminobisphosphonates Extends Longevity in a Mouse Model of Human Premature Aging," Nature Medicine, 2008, vol. 14, No. 7, pp. 767-772.
Labourier et al., "Recognition of Exonic Splicing Enhancer Sequences by the *Drosophila* Splicing Repressor RSF1," Nucleic Acids Research, 1999, vol. 27, No. 11, pp. 2377-2386.
Dignam et al., "Eukaryotic Gene Transcription with Purified Components," Methods in Enzymology, 1983, vol. 101, pp. 582-598.
Tazi et al., "A Protein that Specifically Recognizes the 3' Splice Site of Mammalian Pre-mRNA Introns is Associated with a Small Nuclear Ribonucleoprotein," Cell, 1986, vol. 47, pp. 755-766.
Sanchez-Martin et al., "Symmetrical Bis-Quinolinium Compounds: New Human Choline Kinase Inhibitors with Antiproliferative Activity against the HT-29 Cell Line," Journal of Medicinal Chemistry, 2005, vol. 48, No. 9 pp. 3354-3363.

(56) References Cited

OTHER PUBLICATIONS

Cottet et al., "Recommendable Routes to Trifluoromethyl-Substituted Pyridine-and Quinolinecarboxylic Acids," Eur. J. Org. Chem., 2003, pp. 1559-1568.
Balkau et al., "Syntheis of Ellipticine Intermediates: 6-Amino-, 6-hydroxy-, and 6-Methoxy-5,8-Dimethylisoquinoline," Australian. J. Chem., 1969, vol. 22, pp. 2489-2492.
Sharp, "Split Genes and RNA Splicing," Cell, 1994, vol. 77, pp. 805-815.
Black, "Mechanisms of Alternative Pre-Messenger RNA Splicing," Annu. Rev. Biochem., 2003, vol. 72, pp. 291-336.
Manley et al., "SR Proteins and Splicing Control," Genes & Development, 1996, vol. 10, pp. 1569-1579.
Graveley, "Sorting out the Complexity of SR Protein Functions," RNA, 2000, vol. 6, pp. 1197-1211.
Wang et al., "SC35 Plays a Role in T Cell Development and Alternative Splicing of CD45," Molecular Cell, 2001, vol. 7, pp. 331-342.
Ewing et al., "Analysis of Expressed Sequence Tags Indicates 35,000 Human Genes," Nature Genetics, 2000, vol. 25, pp. 232-234.
Johnson et al., "Genome-Wide Survey of Human Alternative Pre-mRNA Splicing with Exon Junction Microarrays," Science, vol. 302, pp. 2141-2144.
Cartegni et al., "Listening to Silence and Understanding Nonsense: Exonic Mutations that Affect Splicing," Nature Reviews—Genetics, Apr. 2002, vol. 3, pp. 285-298.
Tazi et al., "The Spliceosome: a Novel Multi-faceted Target for Therapy," Trends in Biochemical Sciences, 2005, vol. 30, No. 8, pp. 469-478.
Nissim-Rafinia et al., "Cellular and Viral Splicing Factors Can Modify the Splicing Pattern of CFTR Transcripts Carrying Splicing Mutations," Human Molecular Genetics, 2000, vol. 9, No. 12, pp. 1771-1778.
Hofmann et al., "Htra2-β1 Stimulates an Exonic Splicing Enhancer and can Restore Full-length SMN Expression to Survival Motor Neuron 2 (SMN2)," PNAS, 2000, vol. 97, No. 17, pp. 9618-9623.
Sazani et al., "Systemically Delivered Antisense Oligomers Upregulate Gene Expression in Mouse Tissues," Nature Biotechnology, 2002, vol. 20, pp. 1228-1233.
Sazani et al., "Modulation of Alternative Splicing by Antisense Oligonucleotides," Prog. Mol. Subcell. Biol., vol. 31, pp. 217-239, 2003.
Cartegini et al., "Correction of Disease-associated Exon Skipping by Synthetic Exon-specific Activators," Nature Structural Biology, 2003, vol. 10, No. 2, pp. 120-125.
Andreassi et al., "Aclarubicin Treatment Restores SMN Levels to Cells Derived from Type 1 Spinal Muscular Atrophy Patients," Human Molecular Genetics, 2001, vol. 10, No. 24, pp. 2841-2849.
Liu et al., "Partial Correction of Endogenous F508 CFTR in Human Cystic Fibrosis Airway Epithelia by Spliceosome-mediated RNA Trans-splicing,"Nature Biotechnology, 2002, vol. 20, pp. 47-52.
Bakkour et al., "Small-Molecule Inhibition of HIV pre-mRNA Splicing as a Novel Antiretroviral Therapy to Overcome Drug Resistance," PLOS Pathogens, 2007, vol. 3, issue 10, pp. 1530-1539.
Connor et al., "Vpr is Required for Efficient Replication of Human Immunodeficiency Virus type-1 in Mononuclear Phagocytes," Virology, (1995), vol. 206, pp. 935-944.
Perry et al., "AIDS Dementia: A Review of the Literature," Alzheimer Dis. Assoc. Disord., vol. 1, pp. 221-235, 1987, (PubMed Abstract 3331119).
Pauwels, "Aspects of Successful Drug Discovery and Development," Antiviral Research, vol. 71, pp. 77-89, 2006.
Respess et al., "Evaluation of an Ultrasensitive p24 Antigen Assay as a Potential Alternative to Human Immunodeficiency Virus Type 1 RNA Viral Load Assay in Resource-Limited Settings," Journal of Clinical Microbiology, vol. 43, No. 1, pp. 506-508, 2005.
Loriga et al., "Quinoxaline Chemistry. Part 8. 2[Anilino]-3-[Carboxy]-6(7)-Substituted Quinoxalines as Non Classical Antifolate Agents. Synthesis and Evaluation of In Vitro Anticancer, Anti-HIV and Antifungal Activity," Farmaco, vol. 52, pp. 531-537, 1997.
CAPLUS Record for Loriga et al., "Part 8." (Retrieved Nov. 2013).
Loriga et al., "Quinoxaline Chemistry. Part 7. 2-[Aminobenzoates]- and 2-[Aminobenzoylglutamate]-Quinoxalines as Classical Antifolate Agents. Synthesis and Evaluation of In Vitro Anticancer, Anti-HIV and Antifungal Activity," Farmaco, vol. 52, pp. 157-166, (PubMed Abstract No. 9212450), 1997.
CAPLUS Record for Loriga et al., "Part 7." (Retrieved Nov. 2013).
CAS Registry No. 215589-34-7 added on STN on Dec. 15, 1998.
CAS Registry No. 208661-32-9 added on STN on Jul. 19, 1998.
CAS Registry No. 204851-25-2 added on STN on Apr. 30, 1998.
CAS Registry No. 138386-77-3 added on STN on Jan. 17, 1992.
CAS Registry No. 70682-97-2 added on STN on Nov. 16, 1984.
CAS Registry No. 10562-04-6 added on STN on Nov. 16, 1984.
CAS Registry No. 5468-85-9 added on STN on Nov. 16, 1984.
CAS Registry No. 313266-85-2 added on STN on Jan. 9, 2001.
CAS Registry No. 294668-01-2 added on STN on Oct. 11, 2000.
CAS Registry No. 342653-87-6 added on STN on Jun. 20, 2001.
CAS Registry No. 449780-95-4 added on STN on Sep. 12, 2002.
CAS Registry No. 449780-94-3 added on STN on Sep. 12, 2002.
CAS Registry No. 324526-73-0 added on STN on Feb. 27, 2001.
Jan. 13, 2015 Russian Office Action issued in Russian Application No. 2011149572/04(074427).
Dec. 5, 2014 Office Action issued in U.S. Appl. No. 14/087,762.
Oct. 27, 2014 Office Action issued in U.S. Appl. No. 13/993,990.
El-Sayed et al., "Synthesis of Some Novel Quinoline-3-carboxylic Acids and Pyrimidoquinoline Derivatives as Potential Antimicrobial Agents", Archiv der Pharmize, 2002, pp. 403-410, vol. 335(9).
Silberg et al., "N-Acyl-N, N-dipyridyl and N-acyl-N-pyridyl-N-quinoyl amine based palladium complexes. Synthesis, X-ray structures, heterogenization and use in Heck couplings", Journal of Organmetallic Chemistry, 2001, pp. 6-18, vol. 622.
File Registry on STN, 195876-33-6/RN, entered on Oct. 23, 1997.
File Registry on STN, 70125-24-5/RN, entered on Nov. 16, 1984.
Aug. 15, 2014 Office Action issued in U.S. Appl. No. 13/377,753.
Jun. 27, 2014 Office Action issued in U.S. Appl. No. 13/993,990.
Brandt et al., "Uncoupling activity and physicochemical properties of derivatives of fluazinam," Biochimica et Biophysica Acta, Protein Structure and Molecular Enzymology, 1101(1): 41-7, 1992, abstract only CA 117:82915.
Dec. 23, 2013 Office Action issued in U.S. Appl. No. 13/377,753.
Wang et al., "Alternative isoform regulation in human tissue transcriptomes," Nature, vol. 456, pp. 470-476, Nov. 2008.
Pan et al., "Deep surveying of alternative splicing complexity in the human transcriptome by high-throughput sequencing," Nature Genetics, vol. 40, No. 12, pp. 1413-1415, Dec. 2008.
F. J. Leinweber, "Possible Physiological Roles of Carboxylic Ester Hydrolases," Drug Metabolism Reviews, vol. 18, No. 4, pp. 379-439, 1987.
Mar. 9, 2012 International Search Report issued in International Patent Application No. PCT/IB2011/055643.
Jun. 18, 2013 International Preliminary Report on Patentability issued in International Patent Application No. PCT/IB2011/055643.
U.S. Appl. No. 13/377,753 in the name of Tazi et al., filed Jul. 4, 2012.
U.S. Appl. No. 13/377,745 in the name of Roux et al., filed Jul. 5, 2012.
U.S. Appl. No. 13/993,990 in the name of Tazi et al., filed Jul. 13, 2012.
Johnson et al., "Genome-Wide Survey of Human Alternative Pre-mRNA Splicing with Exon Junction Microarrays," Science, vol. 302, pp. 2141-2144, 2003.
Jun. 27, 2011 International Search Report issued in International Patent Application No. PCT/IB2010/052652.
Jun. 27, 2011 Written Opinion of the International Searching Authority issued in International Patent Application No. PCT/IB2010/052652.
Aug. 9, 2011—International Search Report issued in International Patent Application No. PCT/IB2010/052651.

(56) References Cited

OTHER PUBLICATIONS

Aug. 9, 2011—Written Opinion of the International Searching Authority issued in International Patent Application No. PCT/IB2010/052651.
Apr. 13, 2011 International Search Report issued in International Patent Application No. PCT/IB2010/052650.
Apr. 13, 2011 Written Opinion of the International Searching Authority issued in International Patent Application No. PCT/IB2010/052650.
Dec. 10, 2009 Partial European Search Report issued in European Patent Application No. 09162630.9.
Nov. 19, 2009 European Search Report issued in European Patent Application No. 09305540.
Vulliamy et al., "Mutations in the Telomerase Component NHP2 Cause the Premature Ageing Syndrome Dyskeratosis Congenita," PNAS, 2008, vol. 105, No. 23, pp. 8073-8078.
Brune et al., "Progeria: A New Kind of Laminopathy—Clinical and Molecular Update of the Hutchinson-Gilford Syndrome," 1st European Symposium, 2003.
De Sandre-Giovannoli et al. "Lamin A Truncation in Hutchinson-Gilford Progeria". Science, vol. 300, p. 2055, 2003.
Nov. 10, 2014 International Search Report issued in International Application No. PCT/IB2014/062849.
Nov. 10, 2014 Written Opinion issued in International Application No. PCT/IB2014/062849.
Jun. 10, 2015 Notice of Allowance issued in U.S. Appl. No. 13/377,760.
Jul. 18, 2014 Office Action issued in U.S. Appl. No. 13/377,760.
Aug. 3, 2016 Office Action Issued in U.S. Appl. No. 14/256,334.
Jun. 21, 2016 Office Action issued in U.S. Appl. No. 14/789,149.
Dec. 5, 2016 Office Action Issued in U.S. Appl. No. 14/256,334.
Katoh et al. "Isolation of the intermediates and improved synthesis of pyrido[1',2':1,2]imidazo[4,5b]pyrazines and -quinoxalines", Heterocycles, 1992, 34(10), p. 1965-1972).
Carter et al., "Quinoxalines and related compounds-X1", Tetrahedron, 34(7), p. 981-988, 1978.
Lombardino, "Some 3-Arylaminoquinoxaline-2-carboxylic Acids", Journal of Medicinal Chemistry, 9(5), p. 770-771, 1996.
CAS Registry No. 1004363-48-7 added on STN on Feb. 19, 2008.
CAS Registry No. 438481-24-4 added on STN on Jul. 12, 2002.
CAS Registry No. 933238-11-0 added on STN on Apr. 29, 2007.
CAS Registry No. 1011408-51-7 added on STN on Apr. 1, 2008.
CAS Registry No. 1135230-99-7 added on STN on Apr. 16, 2009.
CAS Registry No. 374598-11-5 added on STN on Dec. 10, 2001.
Dudash et al., "Synthesis and Evaluation of 3-anilio-quinoxalinones as glycogen phosphorlyase inhibitors", Bioorganic & Medicinal Chemistry Letters, 15(21), p. 4790-4793, 2005.
Nov. 17, 2016 Office Action issued in Japanese Patent Application No. 2016-006105.
Nov. 16, 2016 Office Action issued in Japanese Patent Application No. 2016-006102.
Nov. 17, 2016 Office Action issued in Japanese Patent Application No. 2016-006104.
Oct. 3, 2016 Office Action issued in U.S. Appl. no. 13/377,753.
Sep. 27, 2016 Office Action issued in Chinese Application No. 201510023109.1.
Lin Min et al., "Nonsense-mediated mRNA decay and tumors," Journal of International Pathology and Clinical Medicine, vol. 26, No. 4, pp. 291-294.
CAS Registry No. 330663-16-6 added on STN on Apr. 10, 2001.
Jul. 15, 2016 Office Action issued in Japanese Application No. 2015-120567.
Jan. 31, 2017 Office Action Issued in U.S. Appl. No. 14/902,935.
Hernandez-Lopez et al., "Alternative splicing in human tumour viruses: a therapeutic target?" Biochemical Journal, 2012, Biochemical Society, vol. 445, pp. 145-156.
Edwards et al., "Orf-I amd Orf-II- Encoded Proteins in HTLV-1 Infection and Persistence", Viruses, 2011, MDPI, vol. 3, pp. 861-885.
Bisset et. al., "Combined effect of zidovudine (ZDV), lamivudine (3TC) and abacavir (ABC) antiretoviral therapy in suppressing in vitro FIV replication," Antiviral Research, 2002, Elsevier, vol. 53 pp. 35-45.
Powell et. al., "Expression, characterisation and mutagensis of the aspartic proteinase from equine infections anaemia virus," European Journal of Biochemistry, 1996, FEBS, vol. 241, pp. 664-674.
U.S. Appl. No. 15/326,698 filed Jan. 17, 2017 in the name of Tazi et al.
U.S. Appl. No. 14/902,935 filed Jan. 5, 2016 in the name of Tazi et al.
Jan. 17, 2017 International Preliminary Report on Patentability issued in International Patent Application No. PCT/EP2015/066462.
Sep. 22, 2015 International Search Report issued in International Patent Application No. PCT/EP2015/066462.
Ex Parte Gerard Marguierie and Eric Malaud, PTAB 2016, Appeal 2013-004606, U.S. Appl. No. 10/587,697, 7 pages.
Apr. 6, 2017 Office Action Issued in U.S. Appl. No. 13/377,753.
May 5, 2017 Office Action issued in Chinese Application No. 201510023124.6.
Nov. 6, 2017 Office Action issued in U.S. Appl. No. 15/326,698.
Jan. 24, 2018 Office Action issued in U.S. Appl. No. 15/486,836.
Feb. 1, 2018 Office Action issued in U.S. Appl. No. 13/377,753.
Fors et al., "An Efficient Process for Pd-Catalyzed C-N. Cross-Coupling Reactions of Aryl Iodides: Insight Into Controlling Factors," J. Am. Chem. Soc., 2009, 131, 5766-5768.
File Registry on STN, 408510-56-5, dated Apr. 29, 2002.
File Registry on STN, 92873-44-4, dated Dec. 7, 1984.
File Registry on STN, 94541-69-2, dated Feb. 3, 1985.
File Registry on STN, 97978-62-6, dated Sep. 16, 1985.
File Registry on STN, 67412-46-8, dated Nov. 16, 1984.
File Registry on STN, 55360-88-8, dated Nov. 16, 1984.
File Registry on STN, 101350-67-8, dated Apr. 5, 1986.

\* cited by examiner

COMPOUNDS USEFUL FOR TREATING AIDS

This is a continuation of application Ser. No. 13/377,760 filed Jul. 2, 2012, which is a National Stage Application of PCT/IB2010/052651 filed Jun. 14, 2010, and claims the benefit of U.S. Provisional Application Nos. 61/186,544 and 61/186,552 and European Application Nos. 09162630.9 and 09305540.8, all of which were filed on Jun. 12, 2009. The entire disclosures of the prior applications are hereby incorporated by reference herein in their entirety.

The invention relates to novel compounds for the preparation of compositions useful for the treatment of diseases resulting from changes in splicing processes.

Certain indole derivative compounds such as ellipticine derivatives and aza-ellipticine derivatives are already known as intercalating molecules for correcting dysfunctions in gene expression, notably in DNA replication. They have been more specifically described for treating diseases such as cancer, leukemia or AIDS (see in particular patents FR 2 627 493, FR 2 645 861, FR 2 436 786).

Concerning current treatments for AIDS, the various approaches aimed at reducing viral load in patients infected by HIV utilize molecules intended to inhibit the enzymatic activity of viral reverse transcriptase or of the protease involved in virus protein maturation. Regarding reverse transcriptase inhibitors, these can be nucleosidic (NRTIs), non-nucleosidic (NNRTIs) or nucleotidic in nature. The purpose of using these compounds is to prevent a DNA copy of the retroviral genome from being produced and, consequently, from being integrated into the genome of the host cell. Protease inhibitors (PIs) interfere with the proper maturation of viral proteins and cause the production of incomplete particles with altered infectious capacities. There is another type of anti-retroviral compound used for its ability to prevent viruses from entering the cell. These entry inhibitors can be either peptides that interfere with the fusion of viral glycoproteins gp41 or gp120 with the membrane of CD4 cells or molecules that target HIV cellular co-receptors CCR5 and CXCR4. The absence of cellular proteins resembling HIV integrase has also been exploited to develop novel anti-HIV molecules that inhibit this enzymatic activity. Although a number of integrase inhibitors are in the clinical trial phase, no molecule is yet available on the market.

The intracellular splicing process consists of eliminating introns in pre-messenger RNAs to produce mature messenger RNAs that can be used by the translation mechanism of the cell (SHARP, Cell, vol. 77, p. 805-815, 1994). In the case of alternative splicing, the same precursor can be the source of messenger RNAs coding for proteins with distinct functions (BLACK, Annu. Rev. Biochem. vol. 72, p. 291-336, 2003). The precise selection of 5' and 3' splicing sites is thus a mechanism that generates diversity and that can lead to the regulation of gene expression according to the type of tissue or during the development of an organism. The factors involved in this selection include a family of proteins called SR, characterized by the presence of one or two RNA recognition motifs (RRM) and a domain rich in arginine and serine residues called an RS domain (MANLEY & TACKE, Genes Dev., vol. 10, p. 1569-1579, 1996). By binding to short exon or intron sequences of the pre-mRNA, called ESE (exonic splicing enhancer) or ISE (intronic splicing enhancer), SR proteins are able to activate, in a dose-dependant manner, sub-optimal splicing sites and to enable the inclusion of exons (GRAVELEY, RNA, vol. 6, p. 1197-1211, 2000). The activity of an SR protein in alternative splicing is specific insofar as the inactivation of the corresponding gene is lethal (WANG et al., Mol. Cell, vol. 7, p. 331-342, 2001).

Sequencing of the human genome and analysis of EST (expressed sequence tag) banks has revealed that 65% of genes are expressed in the form of alternatively spliced variants (EWING & GREEN, Nat. Genet., vol. 25, p. 232-234, 2000; JOHNSON et al., Science, vol. 302, p. 2141-2144, 2003). This mechanism is thus a favored target of modifications that can affect the factors involved in regulating splicing and of mutations that affect the sequences necessary for this regulation. At present, it is estimated that roughly 50% of the point mutations responsible for genetic diseases induce aberrant splicing. These mutations can interfere with splicing by inactivating or creating splicing sites, but also by modifying or generating regulating elements such as splicing enhancers or splicing silencers in a particular gene (CARTEGNI et al., Nat. Rev. Genet., vol. 3, p. 285-298, 2002; TAZI et al., TIBS, vol. 40, p. 469-478, 2005).

The strategies currently developed to correct these splicing defects rest on the use of various types of molecules (TAZI et al., cited above, 2005).

One strategy aimed at developing novel molecules to correct or eliminate abnormal splicing, for example, rests on the overexpression of proteins that interfere with this type of splicing (NISSIM-RAFINIA et al., Hum. Mol. Genet., vol. 9, p. 1771-1778, 2000; HOFINANN et al., Proc. Natl. Acad. Sci. USA, vol. 97, p. 9618-9623, 2000).

Other strategies rest on the use of antisense oligonucleotides (SAZANI et al., Nat. Biotechnol., vol. 20, p. 1228-1233, 2002; SAZANI & KOLE, Prog. Mol. Subcell. Biol., vol. 31, p. 217-239, 2003) or of PNA (CARTEGNI et al., Nat. Struct. Biol., vol. 10, p. 120-125, 2003) enabling, respectively, the inhibition or activation of a splicing event.

Yet another strategy rests on the identification of compounds that influence the splicing efficiency of the pre-mRNA of interest (ANDREASSI et al., Hum. Mol. Genet., vol. 10, p. 2841-2849, 2001).

Lastly, a strategy based on the use of trans-splicing to replace mutant exons has been described (LIU et al., Nat. Biotechnol., vol. 20, p. 47-52, 2002).

One of the disadvantages of the developed strategies cited above to correct or eliminate abnormal splicing is their production cost. Indeed, the cost of producing antisense oligonucleotides that must be modified to improve their stability, and that of PNA molecules, is high.

Another disadvantage of the developed strategies cited above is that they require the use of expression vectors, such as, for example, for the strategy based on the use of trans-splicing.

International application WO05023255, under French priority of applications FR0310460 and FR0400973, filed by the Applicant, disclosed the use of indole derivatives to treat diseases related to the pre-messenger RNA splicing process in the cell.

Thus it was recently shown that certain indole derivatives prove particularly effective in treating metastatic cancer and in treating AIDS (BAKKOUR et al., PLoS Pathogens, vol. 3, p. 1530-1539, 2007).

However, the compounds described have a flat structure with four rings that have the disadvantage of intercalating between DNA bases and can thus lead to cellular toxicity.

In order to minimize the risk that these indole derivatives intercalate between DNA bases, the inventors developed novel compounds that are particularly effective in treating diseases related to the splicing process, but which, in a surprising manner, have a cellular toxicity that is clearly less than the indole derivatives of the prior art. In addition, these compounds are able to selectively inhibit certain splicing events.

According to a first aspect, a subject-matter of the present invention relates to a compound of formula (I)

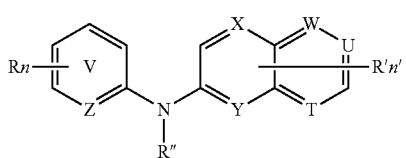

wherein:

means an aromatic ring wherein V is C or N and when V is N, V is in ortho, meta or para of Z, i.e. forms respectively a pyridazine, a pyrimidine or a pyrazine group, R independently represent a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a —NO$_2$ group, a —NR$_1$R$_2$ group, a (C$_1$-C$_4$)alkoxy group, a phenoxy group and a (C$_1$-C$_3$)alkyl group, said alkyl being optionally mono-substituted by a hydroxyl group, R$_1$ and R$_2$ are independently a hydrogen atom or a (C$_1$-C$_3$)alkyl group, n is 1, 2 or 3, n' is 1 or 2, R' is a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$)alkoxy group and a —CN group, R" is a hydrogen atom or a (C$_1$-C$_4$)alkyl group, Z is N or C, Y is N or C, X is N or C, W is N or C, T is N or C, U is N or C, and wherein at most four of the groups V, T, U, Z, Y, X and W are N, and at least one of the groups T, U, Y, X and W is N, or anyone of its pharmaceutically acceptable salt, for use as an agent for preventing, inhibiting or treating AIDS.

According to one aspect, the present invention relates to a compound of formula (I) as defined above, wherein Z is N, V is C, Y is N, X is C, T is C, U is C and W is C, for use as an agent for preventing, inhibiting or treating AIDS.

According to another aspect, the present invention relates to a compound of formula (I) as defined above, wherein Z is C, V is C, Y is N, X is C, T is C, U is C and W is C, for use as an agent for preventing, inhibiting or treating AIDS.

According to another aspect, the present invention relates to a compound of formula (I) as defined above, wherein Z is N, V is C, Y is C, X is N, T is C, U is C and W is C, for use as an agent for preventing, inhibiting or treating AIDS.

According to another aspect, the present invention relates to a compound of formula (I) as defined above, wherein Z is N, V is C, Y is C, X is C, T is C, U is C and W is N, for use as an agent for preventing, inhibiting or treating AIDS.

According to another aspect, the present invention relates to a compound of formula (I) as defined above, wherein Z is N, V is N and is in para of Z, Y is N, X is C, T is C, U is C and W is C, for use as an agent for preventing, inhibiting or treating AIDS.

According to another aspect, the present invention relates to a compound of formula (I) as defined above, wherein Z is C, V is N and is in para of Z, Y is C, X is N, T is C, U is C and W is C, for use as an agent for preventing, inhibiting or treating AIDS.

According to another aspect, the present invention relates to a compound of formula (I) as defined above, wherein Z is C, V is N and is in meta of Z and is in para of the bond linked to NR", Y is N, X is C, T is C, U is C and W is C, for use as an agent for preventing, inhibiting or treating AIDS.

According to another aspect, the present invention relates to a compound of formula (I) as defined above, wherein Z is C, V is N and is in meta of Z and is in para of the bond linked to NR", Y is C, X is N, T is C, U is C and W is C, for use as an agent for preventing, inhibiting or treating AIDS.

According to another aspect, the present invention relates to a compound of formula (I) as defined above, wherein Z is C, V is C, Y is C, X is N, T is C, U is C and W is C, for use as an agent for preventing, inhibiting or treating AIDS.

According to another aspect, the present invention relates to a compound of formula (I) as defined above, wherein Z is C, V is C, Y is N, X is N, T is C, U is C and W is C, for use as an agent for preventing, inhibiting or treating AIDS.

According to another aspect, the present invention relates to a compound of formula (I) as defined above, wherein Z is N, V is N and is in meta of Z and in ortho of the bond linked to NR", Y is N, X is C, T is C, U is C and W is C, for use as an agent for preventing, inhibiting or treating AIDS.

According to another aspect, the present invention relates to a compound of formula (I) as defined above, wherein Z is N, V is N and is in para of Z, Y is C, X is C, T is C, U is C and W is N, for use as an agent for preventing, inhibiting or treating AIDS.

According to another aspect, the present invention relates to a compound of formula (I) as defined above, wherein Z is N, V is N and is in para of Z, Y is C, X is N, T is C, U is C and W is C, for use as an agent for preventing, inhibiting or treating AIDS.

According to another aspect, the present invention relates to a compound of formula (I) as defined above, wherein Z is N, V is C, Y is N, X is N, T is C, U is C and W is C, for use as an agent for preventing, inhibiting or treating AIDS.

According to another aspect, the present invention relates to a compound of formula (I) as defined above, wherein Z is N, V is N and is in meta of Z and is in ortho of the bond linked to NR", Y is N, X is N, T is C, U is C and W is C, for use as an agent for preventing, inhibiting or treating AIDS.

According to another aspect, the present invention relates to a compound of formula (I) as defined above, wherein Z is C, V is C, Y is C, X is C, T is N, U is C and W is C, for use as an agent for preventing, inhibiting or treating AIDS.

According to another aspect, the present invention relates to a compound of formula (I) as defined above, wherein Z is N, V is C, Y is C, X is C, T is N, U is C and W is C, for use as an agent for preventing, inhibiting or treating AIDS.

According to another aspect, the present invention relates to a compound of formula (I) as defined above, wherein Z is N, V is C, Y is C, X is C, T is C, U is N and W is C, for use as an agent for preventing, inhibiting or treating AIDS.

The compounds of the invention may exist in the form of free bases or of addition salts with pharmaceutically acceptable acids.

Suitable physiologically acceptable acid addition salts of compounds of formula (I) include hydrobromide, tartrate, citrate, trifluoroacetate, ascorbate, hydrochloride, tartrate, triflate, maleate, mesylate, formate, acetate and fumarate.

The compounds of formula (I) and or salts thereof may form solvates (e.g. hydrates) and the invention includes all such solvates.

In the context of the present invention, the term:
- "halogen" is understood to mean chlorine, fluorine, bromine, or iodine, and in particular denotes chlorine, fluorine or bromine,
- "$(C_1-C_3)$alkyl" as used herein respectively refers to $C_1-C_3$ normal, secondary or tertiary saturated hydrocarbon. Examples are, but are not limited to, methyl, ethyl, 1-propyl, 2-propyl,
- "$(C_1-C_3)$alkoxy" as used herein respectively refers to O—$(C_1-C_3)$alkyl moiety, wherein alkyl is as defined above. Examples are, but are not limited to, methoxy, ethoxy, 1-propoxy, 2-propoxy,
- "fluoroalkyl group" and "fluoroalkoxy group" refers respectively to alkyl group and alkoxy group as above-defined, said groups being substituted by at least one fluorine atom. Examples are perfluoroalkyl groups, such as trifluoromethyl or perfluoropropyl, and
- "patient" may extend to humans or mammals, such as cats or dogs.

According to one preferred aspect, the present invention relates to a compound of formula (I) as defined above, wherein Z is N, V is C, Y is N, X is C, T is C, U is C and W is C, for use as an agent for preventing, inhibiting or treating AIDS.

According to another preferred aspect, the present invention relates to a compound of formula (I) as defined above, wherein Z is C, V is C, Y is N, X is C, T is C, U is C and W is C, for use as an agent for preventing, inhibiting or treating AIDS.

According to another preferred aspect, the present invention relates to a compound of formula (I) as defined above, wherein Z is N, V is C, Y is C, X is N, T is C, U is C and W is C, for use as an agent for preventing, inhibiting or treating AIDS.

According to another preferred aspect, the present invention relates to a compound of formula (I) as defined above, wherein Z is N, V is N and is in para of Z, Y is N, X is C, T is C, U is C and W is C, for use as an agent for preventing, inhibiting or treating AIDS.

According to another preferred aspect, the present invention relates to a compound of formula (I) as defined above, wherein Z is N, V is C, Y is N, X is N, T is C, U is C and W is C, for use as an agent for preventing, inhibiting or treating AIDS.

Another object of the present invention relates to a compound of the following formula (P):

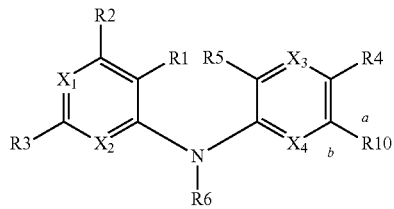

wherein:

X1, X2 and X3 independently represent a nitrogen atom, or a CR8 group, at least one of X1 and X2 being a nitrogen atom;

R8 represents a hydrogen atom or a halogen atom, a hydroxyl, alkyl, trifluoroalkyl, ester, ether, such as a methoxy or trifluoromethoxy group, or benzyl, optionally substituted, a nitro or a cyano group, preferably R8 represents a hydrogen atom, when a ring A, defined below, is in position a, X4 represents a nitrogen atom or a CR8 group, and when a ring A is in position b, X4 represents a carbon atom part of the ring A, R1, R2, R3 and R5 independently represent a hydrogen or a halogen atom, an alkyl, a trifluoroalkylgroup, ether, such as a methoxy or trifluoromethoxy group, or benzyl, optionally substituted, a nitro or a cyano group.

when the ring A is at position b, R4 represents a hydrogen atom, a halogen atom or an alkyl, a trifluoroalkyl, ester, ether group, such as a methoxy or trifluoromethoxy group, or benzyl, optionally substituted, and when the ring A is at position a, R4 is a carbon atom part of the ring A, R10 represents a carbon atom part of ring A, R6 represents a hydrogen atom or an alkyl group, A represents a ring at position a or b of formula I, said ring A corresponding to:

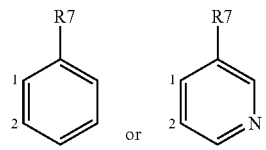

wherein:

R7 represents a hydrogen, or halogen atom or an alkyl, hydroxyl or amine group which can be linear or branched and/or unsaturated and optionally substituted, pharmaceutically acceptable salts of said compounds, isomers thereof and/or mixtures of the same, with the exception of the following compound:

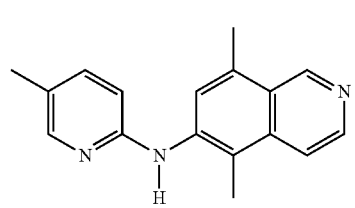

"Halogen atom" means the group comprising F, Cl, Br and I, preferably said halogen atom is a chlorine atom.

"Unsaturated" means that the group comprises at least one double bond.

All the compounds disclosed in the examples are in the scope of the present invention.

Preferably, X1 represents a CR8 group when X2 represents a nitrogen group, and

X2 represents a CR8 group when X1 represents a nitrogen group.

Preferably, at least one of X3 and X4 is a nitrogen atom when the cycle A is in position a.

Preferably X3 and X4 are different, and even more preferably X3 represents a CR8 group when X2 represents a nitrogen group or a and X4 represents a CR8 group when X1 represents a nitrogen group.

Preferably, R1 represents a hydrogen atom or a methoxy group.

Preferably, R2, R3, R4 and R5 independently represent a hydrogen atom or a halogen atom or an alkyl, or benzyl, optionally substituted.

Preferably, R4 represents a hydrogen atom.

Preferably, R2 represents a hydrogen atom or a C1 to C4 alkyl group, preferably a methyl.

Preferably, R3, R5 and R6 independently represent a hydrogen atom.

Preferably, R7 represents a hydrogen, or halogen atom, more preferably a hydrogen or a chlorine atom.

Preferably, the ring A is attached at position a or b of the compound of formula I via the carbons numbered 1 and 2 in ring A.

Preferably, when the ring A is at position a, R4 is the carbon atom numbered 2 of the ring A, more preferably R4 is the carbon atom numbered 2 of the ring A and R10 is the carbon numbered 1.

Preferably, when a ring A is in position b, X4 is the carbon atom numbered 1 of the ring A, more preferably, X4 is the carbon atom numbered 1 of the ring A and R10 is the carbon numbered 2.

Preferably, the compound as described above does not include the following compounds:

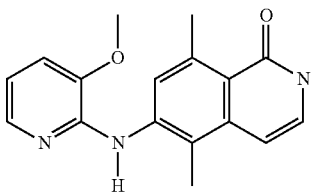 [SMILES: COc1cccnc1Nc1cc(C)c2c(=O)[nH]ccc2c1C]

5,8-Dimethyl-6-(pyridin-2-ylamino)-2H-isoquinolin-1-one

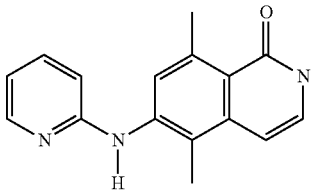 [SMILES: Cc1c(Nc2ccccn2)cc(C)c2c(=O)[nH]ccc12]

5,8-diméthyl-6-(3 methoxy-pyridin-2-ylamino)-isoquinolin-1-one

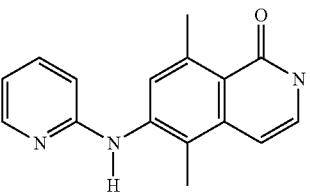

5,8-Dimethyl-6-(pyridin-2-ylamino)-2H-isoquinolin-1-one

Advantageously, the compound of formula I is chosen among the group comprising:

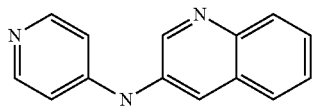 [SMILES: c1ccc2ncc(Nc3ccncc3)cc2c1]

Pyridin-4-yl-quinolin-3-yl-amine; compound (121) of table I

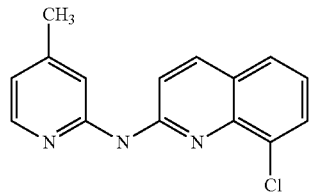

(8-Chloro-quinolin-2-yl)-(4-methyl-pyridin-2-yl)-amine; compound (6) of table I

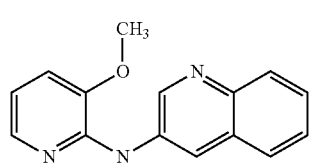 [SMILES: COc1cccnc1Nc1cnc2ccccc2c1]

(3-Methoxy-pyridin-2-yl)-quinolin-3-yl-amine; compound (10) of table I; and

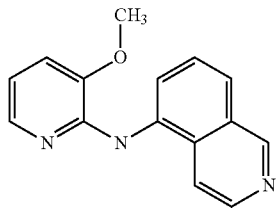 [SMILES: COc1cccnc1Nc1cccc2cnccc12]

Isoquinolin-5-yl-(3-methoxy-pyridin-2-yl)-amine

According to a particular embodiment, an additional subject-matter of the present invention is a compound of formula (Ia)

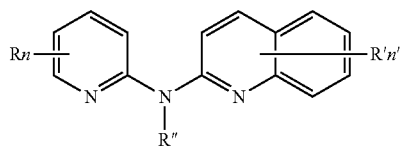
(Ia)

wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a —NO$_2$ group, a —NR$_1$R$_2$ group and a $(C_1-C_3)$alkoxy group, R" is as defined above and is advantageously a hydrogen atom, n is as defined above and is advantageously 1,
n' is as defined above and is advantageously 1,
R' is a hydrogen atom, a halogen atom or a group chosen among a $(C_1-C_3)$alkyl group, a —NO$_2$ group, a $(C_1-C_3)$alkoxy group and a —NR$_1$R$_2$ group, R$_1$ and R$_2$ are a hydrogen atom or a $(C_1-C_3)$alkyl group, or one of its pharmaceutically acceptable salt,
for use as an agent for preventing, inhibiting or treating AIDS.

According to another particular embodiment, an additional subject-matter of the present invention is a compound of formula (Ib)

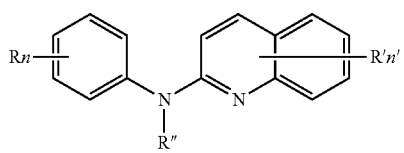
(Ib)

wherein:
R independently represent a hydrogen atom, a halogen atom or a group chosen among a $(C_1-C_3)$alkyl group, a —NR$_1$R$_2$ group, a $(C_1-C_3)$fluoroalkoxy group, a —NO$_2$ group, a phenoxy group and a $(C_1-C_4)$alkoxy group, R$_1$ and R$_2$ are independently a hydrogen atom or a $(C_1-C_3)$alkyl group, R" is as defined above and is advantageously a hydrogen atom, n is as defined above and is preferably 1 or 2,
n' is as defined above and is preferably 1,
R' is a hydrogen atom, a halogen atom or a group chosen among a $(C_1-C_3)$alkyl group and a $(C_1-C_4)$alkoxy group, or one of its pharmaceutically acceptable salt,
for use as an agent for preventing, inhibiting or treating AIDS.

According to another particular embodiment, an additional subject-matter of the present invention is a compound of formula (Ic)

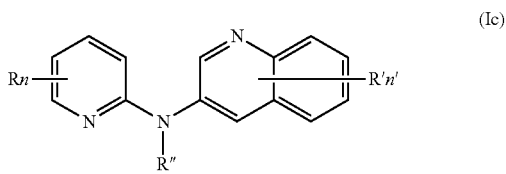
(Ic)

wherein:
R independently represent a hydrogen atom or a group chosen among a $(C_1-C_3)$alkyl group, a $(C_1-C_3)$fluoroalkyl group, a —NR$_1$R$_2$ group, a —COOR$_1$ group, a —NO$_2$ group and a $(C_1-C_3)$alkoxy group, R" is as defined above and is advantageously a hydrogen atom, n is as defined above and is advantageously 1,
n' is as defined above and is advantageously 1,
R' is a hydrogen atom,
R$_1$ and R$_2$ are independently a hydrogen atom or a $(C_1-C_3)$alkyl group, or one of its pharmaceutically acceptable salt,
for use as an agent for preventing, inhibiting or treating AIDS.

According to another particular embodiment, an additional subject-matter of the present invention is a compound of formula (Id)

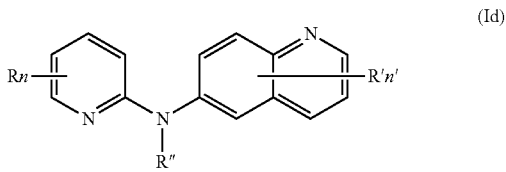
(Id)

wherein:
R independently represent a hydrogen atom or a group chosen among a $(C_1-C_3)$alkyl group, a $(C_1-C_3)$fluoroalkyl group and a $(C_1-C_3)$alkoxy group, R" is as defined above and is advantageously a hydrogen atom, n is as defined above and is advantageously 1,
n' is as defined above and is advantageously 1,
R' is a hydrogen atom, or one of its pharmaceutically acceptable salt,
for use as an agent for preventing, inhibiting or treating AIDS.

According to another particular embodiment, an additional subject-matter of the present invention is a compound of formula (Ie)

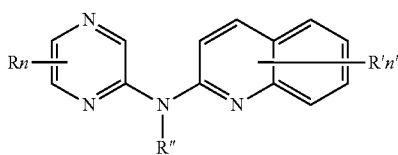

(Ie)

wherein:
R represents a hydrogen atom,
R" is as defined above and is advantageously a hydrogen atom,
n is as defined above and is advantageously 1,
n' is as defined above and is advantageously 1,
R' is a hydrogen atom, a halogen atom or a group chosen among a $(C_1-C_3)$alkyl group and a $(C_1-C_3)$alkoxy group,
or one of its pharmaceutically acceptable salt,
for use as an agent for preventing, inhibiting or treating AIDS.

According to another particular embodiment, an additional subject-matter of the present invention is a compound of formula (If)

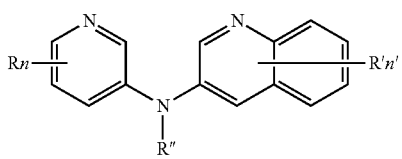

(If)

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating AIDS.

According to another particular embodiment, an additional subject-matter of the present invention is a compound of formula (Ig)

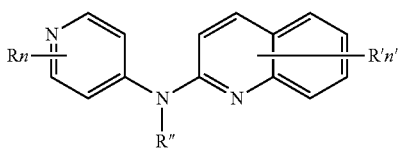

(Ig)

wherein:
R represents a hydrogen atom,
R" is as defined above and is advantageously a hydrogen atom,
n is as defined above and is advantageously 1,
n' is as defined above and is advantageously 1,
R' is a hydrogen atom or a halogen atom,
or one of its pharmaceutically acceptable salt,
for use as an agent for preventing, inhibiting or treating AIDS.

According to another particular embodiment, an additional subject-matter of the present invention is a compound of formula (Ih)

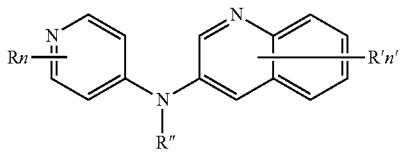

(Ih)

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating AIDS.

According to another particular embodiment, an additional subject-matter of the present invention is a compound of formula (Ii)

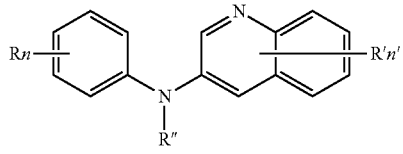

(Ii)

wherein:
R independently represent a hydrogen atom or a group chosen among a $(C_1-C_3)$fluoroalkoxy group and a $(C_1-C_3)$ alkoxy group,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating AIDS.

According to another particular embodiment, an additional subject-matter of the present invention is a compound of formula (Ij)

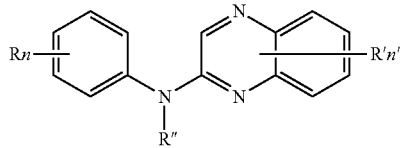

(Ij)

wherein:
R independently represent a hydrogen atom or a group chosen among a $(C_1-C_3)$fluoroalkoxy group and a $(C_1-C_3)$ alkyl group,
R" is as defined above and is advantageously a hydrogen atom, n is as defined above and is advantageously 1,
n' is as defined above and is advantageously 1,
R' is a hydrogen atom,
or one of its pharmaceutically acceptable salt,
for use as an agent for preventing, inhibiting or treating AIDS.

According to another particular embodiment, an additional subject-matter of the present invention is a compound of formula (Ik)

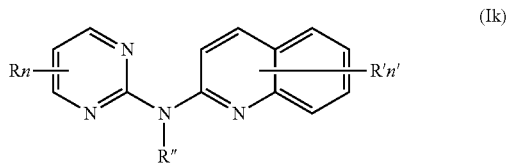

wherein:
R represents a hydrogen atom,
R" is as defined above and is advantageously a hydrogen atom,
n is as defined above and is advantageously 1,
n' is as defined above and is advantageously 1,
R' is a hydrogen atom, a halogen atom or a $(C_1-C_3)$alkyl group,
or one of its pharmaceutically acceptable salt,
for use as an agent for preventing, inhibiting or treating AIDS.

According to another particular embodiment, an additional subject-matter of the present invention is a compound of formula (Il)

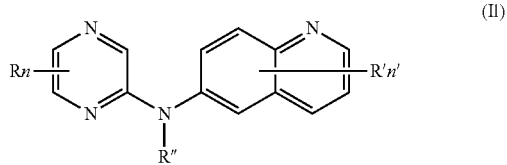

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating AIDS.

According to another particular embodiment, an additional subject-matter of the present invention is a compound of formula (Im)

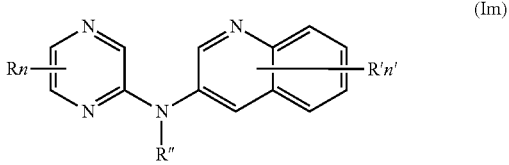

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating AIDS.

According to another particular embodiment, an additional subject-matter of the present invention is a compound of formula (Io)

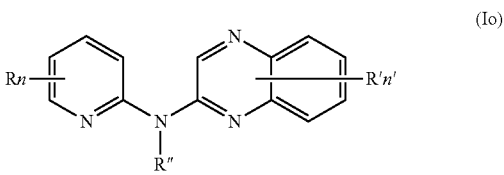

wherein:
R independently represent a hydrogen atom or a halogen atom or a group chosen among, a —$NO_2$ group, a —CN group and a $(C_1-C_3)$alkyl group, said alkyl being optionally mono-substituted by a hydroxyl group,
R" is as defined above and is advantageously a hydrogen atom,
n is as defined above and is advantageously 1,
n' is as defined above and is advantageously 1,
R' is a hydrogen atom, a halogen atom or a $(C_1-C_3)$ fluoroalkyl group,
or one of its pharmaceutically acceptable salt,
for use as an agent for preventing, inhibiting or treating AIDS.

According to another particular embodiment, an additional subject-matter of the present invention is a compound of formula (Ip)

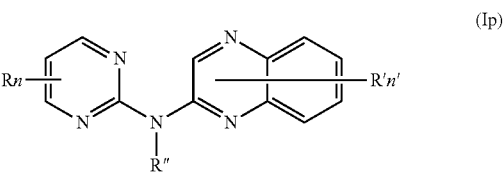

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating AIDS.

According to another particular embodiment, an additional subject-matter of the present invention is a compound of formula (Iq)

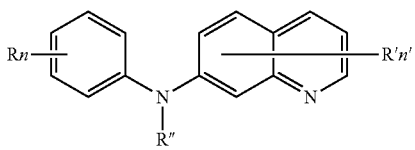

(Iq)

wherein:

R independently represent a hydrogen atom, a $(C_1-C_3)$ alkoxy group or a $(C_1-C_3)$fluoroalkoxy group, R" is as defined above and is advantageously a hydrogen atom, n is as defined above and is advantageously 1, n' is as defined above and is advantageously 1, R' is a hydrogen atom or a group chosen among a —$NR_1R_2$ group, a N-methylpiperazinyl group, a $(C_1-C_3)$ alkoxy group and a morpholino group, $R_1$ and $R_2$ are independently a hydrogen atom or a $(C_1-C_3)$alkyl group, or one of its pharmaceutically acceptable salt, for use as an agent for preventing, inhibiting or treating AIDS.

According to another particular embodiment, an additional subject-matter of the present invention is a compound of formula (Ir)

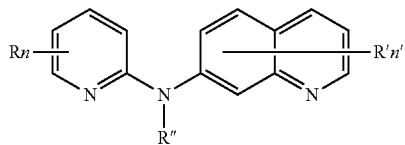

(Ir)

wherein:

R independently represent a hydrogen atom or a $(C_1-C_3)$ alkyl group,

R" is as defined above and is advantageously a hydrogen atom, n is as defined above and is advantageously 1, n' is as defined above and is advantageously 1, R' is a hydrogen atom or a group chosen among a —$NR_1R_2$ group, a morpholino group and a $(C_1-C_3)$alkoxy group, $R_1$ and $R_2$ are independently a hydrogen atom or a $(C_1-C_3)$alkyl group, or one of its pharmaceutically acceptable salt, for use as an agent for preventing, inhibiting or treating AIDS.

According to another particular embodiment, an additional subject-matter of the present invention is a compound of formula (Iee)

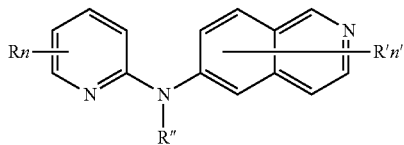

(Iee)

wherein:

R independently represent a hydrogen atom, a $(C_1-C_3)$ alkyl group or a $(C_1-C_3)$fluoroalkyl group, R" is as defined above and is advantageously a hydrogen atom, n is as defined above and is advantageously 1, n' is as defined above and is advantageously 2, R' is a hydrogen atom or a $(C_1-C_3)$alkyl group, or one of its pharmaceutically acceptable salt, for use as an agent for preventing, inhibiting or treating AIDS.

Among the previous defined families of compounds of formulae (Ia) to (Iee), some are more particularly preferred for their use as an agent for preventing, inhibiting or treating AIDS. These preferred compounds particularly belong to formulae (Ia), (Ib), (Ic), (Ie) and (Io), as defined above or one of its pharmaceutically acceptable salts.

Accordingly the present invention further relates to a compound of formula (Ia), (Ib), (Ic), (Ie) and (Io), as defined above, for use as an agent for preventing, inhibiting or treating AIDS.

Thus, according to a more particular embodiment, the present invention particularly focuses on a compound of formula (Ia)

wherein:

R independently represent a hydrogen atom, a halogen atom or a group chosen among a $(C_1-C_3)$alkyl group, a $(C_1-C_3)$fluoroalkyl group, a hydroxyl group, a —CN group, a -COOH group and a $(C_1-C_3)$alkoxy group, R" is as defined above and more preferably is a hydrogen atom, n is as defined above and more preferably is 1, n' is as defined above, R' is a hydrogen atom, a halogen atom, a —$NO_2$ group or a $(C_1-C_3)$alkyl group, or one of its pharmaceutically acceptable salt, for use as an agent for preventing, inhibiting or treating AIDS.

Still according to this more particular embodiment, the present invention more preferably focuses on compounds of formula (Ia'),

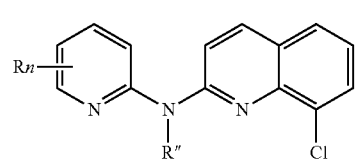

(Ia')

wherein,

R independently represent a hydrogen atom, a —CN group, a $(C_1-C_3)$alkyl group, a $(C_1-C_3)$fluoroalkyl group, a halogen atom or a hydroxyl group, R' is as defined in formula (Ia) and is preferably a halogen, a $(C_1-C_3)$alkyl group or a $NO_2$ group, R" is a hydrogen atom, n is 1 or 2 or one of its pharmaceutically acceptable salt, for use as an agent for preventing, inhibiting or treating AIDS.

According to another more particular embodiment, the present invention particularly focuses on a compound of formula (Ib)

wherein:

R independently represent a hydrogen atom, a halogen atom, a group chosen among a $(C_1-C_4)$alkyl group, a —$NR_1R_2$ group, a $(C_1-C_3)$alkoxy group and a $(C_1-C_3)$ fluoroalkoxy group, $R_1$ and $R_2$ are independently a hydrogen atom or a $(C_1-C_3)$alkyl group, R" is as defined above and more preferably is a hydrogen atom, n is as defined above, n' is as defined above, R' is a hydrogen atom, halogen atom or a $(C_1-C_3)$alkyl group, or one of its pharmaceutically acceptable salt, for use as an agent for preventing, inhibiting or treating AIDS.

Still according to this more particular embodiment, the present invention more preferably focuses on compounds of formula (Ib'),

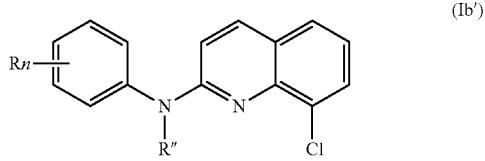

wherein:

R independently represent a hydrogen atom, a halogen atom, a group chosen among a $(C_1-C_3)$alkoxy group, a $(C_1-C_3)$fluoroalkoxy group, R" is as defined above and more preferably is a hydrogen atom, n is as defined above and more preferably is 1, or one of its pharmaceutically acceptable salt, for use as an agent for preventing, inhibiting or treating AIDS.

According to another more particular embodiment, the present invention particularly focuses on a compound of formula (Ic)

wherein:

R independently represent a hydrogen atom or a group chosen among a $(C_1-C_3)$fluoroalkyl group, a —$NO_2$ group, a —$NR_1R_2$ group and a $(C_1-C_3)$alkoxy group, $R_1$ and $R_2$ are independently a hydrogen atom or a $(C_1-C_3)$alkyl group, R" is as defined above and more preferably is a hydrogen atom, n is as defined above and more preferably is 1, n' is as defined above, R is a hydrogen atom, or one of its pharmaceutically acceptable salt, for use as an agent for preventing, inhibiting or treating AIDS.

According to another more particular embodiment, the present invention particularly focuses on a compound of formula (Ie)

wherein:

R represents a hydrogen atom,

R" is as defined above and more preferably is a hydrogen atom, n is as defined above and more preferably is 1, n' is as defined above, R' is a hydrogen atom or a halogen atom, or one of its pharmaceutically acceptable salt, for use as an agent for preventing, inhibiting or treating According to another more particular embodiment, the present invention particularly focuses on a compound of formula (Io)

wherein:

R independently represent a hydrogen atom, a halogen atom or a group chosen among a $(C_1-C_3)$alkyl group and a —$NO_2$ group, R" is as defined above and more preferably is a hydrogen atom, n is 1, 2 or 3, n' is as defined above, R' is a hydrogen atom or a $(C_1-C_3)$fluoroalkyl group, or one of its pharmaceutically acceptable salt, for use as an agent for preventing, inhibiting or treating AIDS.

In a particular embodiment, the present invention relates to a compound of formula (Ia), (Ic) or (Io) as defined above or one of its pharmaceutically acceptable salts, for use as an agent for preventing, inhibiting or treating AIDS.

According to a preferred embodiment of the present invention, the compound for use as an agent for preventing, inhibiting or treating AIDS, is chosen from:

(1) (8-Chloro-quinolin-2-yl)-pyridin-2-yl-amine
(2) 2-(Quinolin-2-ylamino)-isonicotinic acid
(3) (4-Methyl-pyridin-2-yl)-quinolin-2-yl-amine
(4) Pyridin-2-yl-quinolin-2-yl-amine
(5) 2-(8-Chloro-quinolin-2-ylamino)-isonicotinic acid
(6) (8-Chloro-quinolin-2-yl)-(4-methyl-pyridin-2-yl)-amine
(7) 6-(Quinolin-2-ylamino)-nicotinonitrile
(8) Quinolin-2-yl-(4-trifluoromethoxy-phenyl)-amine
(9) Pyridin-2-yl-quinolin-3-yl-amine
(10) (3-Methoxy-pyridin-2-yl)-quinolin-3-yl-amine
(11) Quinolin-3-yl-(5-trifluoromethyl-pyridin-2-yl)-amine
(12) (5-Nitro-pyridin-2-yl)-quinolin-3-yl-amine
(13) (5-Methyl-pyridin-2-yl)-quinolin-3-yl-amine
(14) 2-(Quinolin-3-ylamino)-isonicotinic acid
(15) Quinolin-6-yl-(5-trifluoromethyl-pyridin-2-yl)-amine
(16) (6-Methyl-pyridin-2-yl)-quinolin-6-yl-amine
(17) N-(6-methylpyridin-2-yl)quinolin-2-amine
(18) 8-chloro-N-(6-methylpyridin-2-yl)quinolin-2-amine
(19) 4-methyl-N-(pyridin-2-yl)quinolin-2-amine
(20) 4-methyl-N-(4-methylpyridin-2-yl)quinolin-2-amine
(21) 3-methyl-N-(4-methylpyridin-2-yl)quinolin-2-amine
(22) 3-methyl-N-(pyridin-2-yl)quinolin-2-amine
(23) 6-((4-methylquinolin-2-yl)amino)nicotinonitrile
(24) 6-((3-methylquinolin-2-yl)amino)nicotinonitrile
(25) 6-chloro-N-(4-methylpyridin-2-yl)quinolin-2-amine
(26) 6-chloro-N-(6-methylpyridin-2-yl)quinolin-2-amine
(27) 4-methyl-N-(5-nitropyridin-2-yl)quinolin-2-amine
(28) N-(3-nitropyridin-2-yl)quinolin-2-amine
(29) 8-chloro-N-(3-nitropyridin-2-yl)quinolin-2-amine
(30) 2-((4-methylquinolin-2-yl)amino)nicotinonitrile
(31) N-(3-methylpyridin-2-yl)quinolin-2-amine
(32) N-(5-methylpyridin-2-yl)quinolin-2-amine
(33) 2-(quinolin-2-ylamino)isonicotinonitrile
(34) N-(5-(trifluoromethyl)pyridin-2-yl)quinolin-2-amine
(35) 8-chloro-N-(3-methylpyridin-2-yl)quinolin-2-amine
(36) 8-chloro-N-(5-methylpyridin-2-yl)quinolin-2-amine
(37) 8-chloro-N-(5-(trifluoromethyl)pyridin-2-yl)quinolin-2-amine
(38) N-(3-methoxypyridin-2-yl)quinolin-2-amine
(39) N-(5-nitropyridin-2-yl)quinolin-2-amine
(40) 6-((8-chloroquinolin-2-yl)amino)nicotinonitrile
(41) N-(5-fluoropyridin-2-yl)quinolin-2-amine
(42) N-(6-(trifluoromethyl)pyridin-2-yl)quinolin-2-amine
(43) 8-chloro-N-(5-fluoropyridin-2-yl)quinolin-2-amine
(44) 2-((8-chloroquinolin-2-yl)amino)nicotinic acid
(45) 4-methyl-N-(6-methylpyridin-2-yl)quinolin-2-amine
(46) 3-methyl-N-(6-methylpyridin-2-yl)quinolin-2-amine
(47) 5-cyano-2-(quinolin-2-ylamino)pyridin-1-ium chloride

(48) 2-((8-chloroquinolin-2-yl)amino)-4-methylpyridin-1-ium chloride
(49) 8-chloro-N-(4-ethylpyridin-2-yl)quinolin-2-amine
(50) 8-chloro-N-(6-ethylpyridin-2-yl)quinolin-2-amine
(51) 8-chloro-N-(4,6-dimethylpyridin-2-yl)quinolin-2-amine
(52) 6-((8-chloroquinolin-2-yl)amino)-2-methylnicotinonitrile
(53) 8-chloro-N-(4-chloropyridin-2-yl)quinolin-2-amine
(54) 8-methyl-N-(4-methylpyridin-2-yl)quinolin-2-amine
(55) N-(5-bromo-4-methylpyridin-2-yl)-8-chloroquinolin-2-amine
(56) 8-chloro-N-(3-ethyl-6-methylpyridin-2-yl)quinolin-2-amine
(57) 8-fluoro-N-(4-methylpyridin-2-yl)quinolin-2-amine
(58) 8-bromo-N-(4-methylpyridin-2-yl)quinolin-2-amine
(59) methyl 6-(quinolin-2-ylamino)nicotinate
(60) methyl 6-[(8-chloroquinolin-2-yl)amino]pyridine-3-carboxylate
(61) methyl 6-[(3-methylquinolin-2-yl)amino]pyridine-3-carboxylate
(62) methyl 2-[(8-chloroquinolin-2-yl)amino]pyridine-3-carboxylate
(63) 8-methoxy-N-(4-methylpyridin-2-yl)quinolin-2-amine
(64) N-(4-methylpyridin-2-yl)-5-nitroquinolin-2-amine
(65) 2-N-(4-methylpyridin-2-yl)quinoline-2,8-diamine
(66) N-(4-methylpyridin-2-yl)-5-aminoquinolin-2-amine
(67) methyl 6-[(4-methylquinolin-2-yl)amino]pyridine-3-carboxylate
(68) 8-chloro-N-[4-(trifluoromethyl)pyridin-2-yl]quinolin-2-amine
(69) 2-[(8-chloroquinolin-2-yl)amino]pyridin-3-ol
(70) 8-chloro-N-[6-(trifluoromethyl)pyridin-2-yl]quinolin-2-amine
(71) 6-chloro-N-(5-fluoropyridin-2-yl)quinolin-2-amine
(72) N-(6-ethylpyridin-2-yl)-3-methylquinolin-2-amine
(73) N-(5-fluoropyridin-2-yl)-3-methylquinolin-2-amine
(74) 3-methyl-N-[5-(trifluoromethyl)pyridin-2-yl]quinolin-2-amine
(75) 4-N-(8-chloroquinolin-2-yl)-1-N,1-N-dimethylbenzene-1,4-diamine
(76) N-(4-methoxyphenyl)quinolin-2-amine
(77) 8-chloro-N-(4-methoxyphenyl)quinolin-2-amine
(78) 4-methyl-N-[4-(trifluoromethoxy)phenyl]quinolin-2-amine
(79) N-(4-methoxyphenyl)-3-methylquinolin-2-amine
(80) 3-methyl-N-[4-(trifluoromethoxy)phenyl]quinolin-2-amine
(81) 1-N,1-N-dimethyl-4-N-(3-methylquinolin-2-yl)benzene-1,4-diamine
(82) N-[2-methyl-4-(trifluoromethoxy)phenyl]quinolin-2-amine
(83) N-[3-(trifluoromethoxy)phenyl]quinolin-2-amine
(84) N-[2-(trifluoromethoxy)phenyl]quinolin-2-amine
(85) N-(4-nitrophenyl)quinolin-2-amine
(86) N-(3-fluorophenyl)quinolin-2-amine
(87) 8-chloro-N-[3-(trifluoromethoxy)phenyl]quinolin-2-amine
(88) 8-chloro-N-(3-fluorophenyl)quinolin-2-amine
(89) 2-{[4-(trifluoromethoxy)phenyl]amino}quinolin-1-ium chloride
(90) 8-chloro-N-[4-(trifluoromethoxy)phenyl]quinolin-2-amine
(91) 3-methyl-N-[2-methyl-4-(trifluoromethoxy)phenyl]quinolin-2-amine
(92) 3-methyl-N-[3-(trifluoromethoxy)phenyl]quinolin-2-amine
(93) 3-methyl-N-[2-(trifluoromethoxy)phenyl]quinolin-2-amine
(94) 8-chloro-N-[2-methyl-4-(trifluoromethoxy)phenyl]quinolin-2-amine
(95) 3-methyl-2-{[4-(trifluoromethoxy)phenyl]amino}quinolin-1-ium chloride
(96) 6-chloro-N-(4-(trifluoromethoxy)phenyl)quinolin-2-amine
(97) 4-methyl-2-{[4-(trifluoromethoxy)phenyl]amino}quinolin-1-ium chloride
(98) 8-bromo-N-[4-(trifluoromethoxy)phenyl]quinolin-2-amine
(99) 8-fluoro-N-[4-(trifluoromethoxy)phenyl]quinolin-2-amine
(100) 8-methyl-N-[4-(trifluoromethoxy)phenyl]quinolin-2-amine
(101) N-(4-butoxyphenyl)-8-chloroquinolin-2-amine
(102) N-(4-phenoxyphenyl)quinolin-2-amine
(103) 8-methoxy-N-[4-(trifluoromethoxy)phenyl]quinolin-2-amine
(104) 8-chloro-N-[3-chloro-4-(trifluoromethoxy)phenyl]quinolin-2-amine
(105) N-(6-methylpyridin-2-yl)quinolin-3-amine
(106) N-(3-nitropyridin-2-yl)quinolin-3-amine
(107) N-(5-methylpyridin-2-yl)quinolin-6-amine
(108) N-(3-methoxypyridin-2-yl)quinolin-6-amine
(109) 6-chloro-N-(pyrazin-2-yl)quinolin-2-amine
(110) 8-bromo-N-(pyrazin-2-yl)quinolin-2-amine
(111) 8-methyl-N-(pyrazin-2-yl)quinolin-2-amine
(112) 8-chloro-N-(pyrazin-2-yl)quinolin-2-amine
(113) N-(pyrazin-2-yl)quinolin-2-amine
(114) 4-methyl-N-(pyrazin-2-yl)quinolin-2-amine
(115) 3-methyl-N-(pyrazin-2-yl)quinolin-2-amine
(116) 8-fluoro-N-(pyrazin-2-yl)quinolin-2-amine
(117) 8-methoxy-N-(pyrazin-2-yl)quinolin-2-amine
(118) N-(pyridin-3-yl)quinolin-3-amine
(119) 8-chloro-N-(pyridin-4-yl)quinolin-2-amine
(120) N-(pyridin-4-yl)quinolin-2-amine
(121) N-(pyridin-4-yl)quinolin-3-amine
(122) N-[4-(trifluoromethoxy)phenyl]quinolin-3-amine
(123) N-(4-methoxyphenyl)quinolin-3-amine
(124) N-[4-(trifluoromethoxy)phenyl]quinoxalin-2-amine
(125) N-[2-methyl-4-(trifluoromethoxy)phenyl]quinoxalin-2-amine
(126) N-[3-(trifluoromethoxy)phenyl]quinoxalin-2-amine
(127) N-[2-(trifluoromethoxy)phenyl]quinoxalin-2-amine
(128) N-(pyrimidin-2-yl)quinolin-2-amine
(129) 8-chloro-N-(pyrimidin-2-yl)quinolin-2-amine
(130) 4-methyl-N-(pyrimidin-2-yl)quinolin-2-amine
(131) N-(pyrazin-2-yl)quinolin-6-amine
(132) N-(pyrazin-2-yl)quinolin-3-amine
(133) 6-methyl-N-(naphthalen-2-yl)pyridin-2-amine
(134) N-(naphthalen-2-yl)pyridin-2-amine
(135) N-(pyridin-2-yl)quinoxalin-2-amine
(136) N-(4-methylpyridin-2-yl)quinoxalin-2-amine
(137) 6-(quinoxalin-2-ylamino)pyridine-3-carbonitrile
(138) N-(6-methylpyridin-2-yl)quinoxalin-2-amine
(139) N-(4-methylpyridin-2-yl)-3-(trifluoromethyl)quinoxalin-2-amine
(140) N-(3,5-dichloro-4-methylpyridin-2-yl)quinoxalin-2-amine
(141) N-(4-methyl-3-nitropyridin-2-yl)quinoxalin-2-amine
(142) N-(pyrimidin-2-yl)quinoxalin-2-amine
(143) 4-N,4-N-dimethyl-7-N-[4-(trifluoromethoxy)phenyl]quinoline-4,7-diamine
(144) 4-(morpholin-4-yl)-N-[4-(trifluoromethoxy)phenyl]quinolin-7-amine (145) 4-methoxy-N-(pyridin-2-yl)quinolin-7-amine
(146) 4-methoxy-N-(4-methylpyridin-2-yl)quinolin-7-amine
(147) 4-N,4-N-dimethyl-7-N-(4-methylpyridin-2-yl)quinoline-4,7-diamine
(148) 5,8-dimethyl-N-(5-methylpyridin-2-yl)isoquinolin-6-amine
(149) 5,8-dimethyl-N-(5-trifluoromethylpyridin-2-yl)isoquinolin-6-amine
(150) N-(4-methylpyridin-2-yl)-8-nitroquinolin-2-amine
(151) 6-chloro-N-(6-ethylpyridin-2-yl)quinolin-2-amine
(152) 6-chloro-N-(5-methylpyridin-2-yl)quinolin-2-amine
(153) 6-chloro-N-[5-(trifluoromethyl)pyridin-2-yl]quinolin-2-amine
(154) N2-(8-chloroquinolin-2-yl)-4-methylpyridine-2,3-diamine
(155) N-(4-butoxyphenyl)-3-methylquinolin-2-amine
(156) 4-N-(6-chloroquinolin-2-yl)-1-N,1-N-dimethylbenzene-1,4-diamine
(157) 8-chloro-N-(3-chloro-4-methoxyphenyl)quinolin-2-amine
(158) N1-(8-chloroquinolin-2-yl)-4-(trifluoromethoxy)benzene-1,2-diamine
(159) N-(3-aminopyridin-2-yl)quinolin-3-amine
(160) 6-chloro-N-(4-methylpyridin-2-yl)quinoxalin-2-amine
(161) N-(4-ethylpyridin-2-yl)quinoxalin-2-amine
(162) N-(5-bromo-4-methylpyridin-2-yl)quinoxalin-2-amine
(163) N-(4,6-dimethylpyridin-2-yl)quinoxalin-2-amine
(164) [2-(quinoxalin-2-ylamino)pyridin-4-yl]methanol
(165) N-(4-methyl-5-nitropyridin-2-yl)quinoxalin-2-amine
(166) N-(4-methoxyphenyl)-4-(4-methylpiperazin-1-yl)quinolin-7-amine
(167) 4-methoxy-N-[4-(trifluoromethoxy)phenyl]quinolin-7-amine
(168) N-(4-methylpyridin-2-yl)-4-(morpholin-4-yl)quinolin-7-amine
and their pharmaceutically acceptable salts.

Among said compounds, compounds (1), (6), (33), (34), (35), (36), (37), (38), (42), (43), (44), (45), (46), (48), (50), (64), (68), (69), (70), (71), (72), (73), (74), (75), (77), (78), (79), (80), (81), (82), (86), (87), (88), (90), (92), (96), (104), (106), (109), (112), (136), (139), (140) and (141) are of particular interest.

The present invention therefore extends to compounds (1), (6), (33), (34), (35), (36), (37), (38), (42), (43), (44), (45), (46), (48), (50), (64), (68), (69), (70), (71), (72), (73), (74), (75), (77), (78), (79), (80), (81), (82), (86), (87), (88), (90), (92), (96), (104), (106), (109), (112), (136), (139), (140) and (141) or one of its pharmaceutically acceptable salts for use as an agent for preventing, inhibiting or treating AIDS.

Some of said preceding compounds are new and form part of the present invention: (1), (6), (33), (34), (35), (36), (37), (38), (42), (43), (44), (46), (48), (50), (64), (68), (69), (70), (71), (72), (73), (74), (75), (77), (78), (79), (80), (81), (82), (86), (87), (88), (90), (92), (96), (104), (106), (109), (112), (136), (139), (140), (141) and their pharmaceutically acceptable salts, such as hydrobromide, tartrate, citrate, trifluoroacetate, ascorbate, hydrochloride, tartrate, triflate, maleate, mesylate, formate, acetate and fumarate.

The compounds of formulae (I), (Ia), (Ib), (Ic), (Id), (Ie), (If), (Ig), (Ih), (Ii), (Ij), (Ik), (Il), (Im), (Io), (Ip), (Iq), (Ir) and (Tee) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

Among the compounds of formula (I), some of them are new and form part of the invention, as well as their pharmaceutically acceptable salts, such as hydrobromide, tartrate, citrate, trifluoroacetate, ascorbate, hydrochloride, tartrate, triflate, maleate, mesylate, formate, acetate and fumarate.

According to a particular embodiment, the present invention encompasses compounds of formula (Ig) wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group, n is 1 or 2, n' is 1 or 2, R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, R" is a hydrogen atom or a $(C_1-C_4)$alkyl group, R$_1$ and R$_2$ are independently a hydrogen atom or a $(C_1-C_3)$alkyl group, with the proviso that R and R' are not simultaneously a hydrogen atom, and when n and n' are 1 and R is a hydrogen atom then R' is not a —COOH group, or anyone of its pharmaceutically acceptable salt.

According to another particular embodiment, the present invention encompasses compounds of formula (If) wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group, n is 1 or 2, n' is 1 or 2, R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, R" is a hydrogen atom or a $(C_1-C_4)$alkyl group, R$_1$ and R$_2$ are independently a hydrogen atom or a $(C_1-C_3)$alkyl group, or anyone of its pharmaceutically acceptable salt.

According to another particular embodiment, the present invention encompasses compounds of formula (Ih) wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group, n is 1 or 2, n' is 1 or 2, R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, R" is a hydrogen atom or a $(C_1-C_4)$alkyl group, R$_1$ and R$_2$ are independently a hydrogen atom or a $(C_1-C_3)$alkyl group, or anyone of its pharmaceutically acceptable salt.

According to another particular embodiment, the present invention encompasses compounds of formula (Il) wherein:

R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group, and a ($C_1$-$C_3$)alkoxy group, n is 1 or 2, n' is 1 or 2, R' is a hydrogen atom or a group chosen among a ($C_1$-$C_3$)alkyl group, a halogen atom, a hydroxyl group, a —COOR$_1$ group, a —NO$_2$ group, a —NR$_1$R$_2$ group, a ($C_1$-$C_3$)alkoxy group and a —CN group, R" is a hydrogen atom or a ($C_1$-$C_4$)alkyl group, R$_1$ and R$_2$ are independently a hydrogen atom or a ($C_1$-$C_3$)alkyl group, with the proviso that R and R' are not simultaneously a hydrogen atom, or anyone of its pharmaceutically acceptable salt.

According to another particular embodiment, the present invention encompasses compounds of formula (Im) wherein:

R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group, and a ($C_1$-$C_3$)alkoxy group, n is 1 or 2, n' is 1 or 2, R' is a hydrogen atom or a group chosen among a ($C_1$-$C_3$)alkyl group, a halogen atom, a hydroxyl group, a —COOR$_1$ group, a —NO$_2$ group, a —NR$_1$R$_2$ group, a ($C_1$-$C_3$)alkoxy group and a —CN group, R" is a hydrogen atom or a ($C_1$-$C_4$)alkyl group, R$_1$ and R$_2$ are independently a hydrogen atom or a ($C_1$-$C_3$)alkyl group, with the proviso that when n and n' are 1 and R is a hydrogen atom, R' is not a chlorine atom, or anyone of its pharmaceutically acceptable salt.

For a sake of simplification, the following compounds and their corresponding definitions are called "new compounds".

According to another particular embodiment, the present invention encompasses compounds of formula (Ia), as such, wherein:

R" and n are as defined in formula (Ia), n' is 1,

R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a —NO$_2$ group, a ($C_1$-$C_3$)fluoroalkoxy group and a ($C_1$-$C_3$)alkoxy group, R' is a hydrogen atom or a halogen atom or a group chosen among a ($C_1$-$C_3$)alkyl group, a —COOR$_1$ group, and a —CN group, and wherein:

with the proviso that when R and R' are not simultaneously a hydrogen atom, when n is 1, R is not a methyl group in ortho or para position with respect to Z, Z being N, when R' is a hydrogen atom, R is not a bromine atom or a chlorine atom, when R is a hydrogen atom, R' is not a methyl or ethyl group, a —COOH group, a COOC$_2$H$_5$ group or a bromine atom, said bromine atom being in ortho position of the bond linked to NR", or one of its pharmaceutically acceptable salt.

Still according to this particular embodiment, the present invention more particularly focuses on compounds of formula (Ia), as such, wherein, R independently represent a hydrogen atom, a ($C_1$-$C_3$) fluoroalkyl group, a halogen atom, a —CN group or a ($C_1$-$C_3$) alkyl group, R" is as defined in formula (Ia), R' is a hydrogen atom, a halogen atom or a —NO$_2$ group, n' is 1, n is 1, with the proviso that when n is 1, R is not a methyl group in ortho or para position with respect to Z, Z being N, R is not a bromine atom or a chlorine atom when R' is a hydrogen atom, or one of its pharmaceutically acceptable salt.

Still according to this particular embodiment, the present invention more preferably focuses on compounds of formula (Ia'), as such,

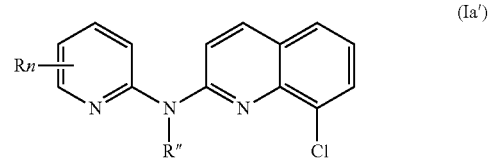

wherein,

R independently represent a hydrogen atom, a ($C_1$-$C_3$) alkyl group, a ($C_1$-$C_3$)fluoroalkyl group, a halogen atom or a hydroxyl group, R" is as defined in formula (Ia), n is 1 or 2, and preferably 1, or one of its pharmaceutically acceptable salt.

The present invention further relates to a compound of formula (Ib) as defined above, as such

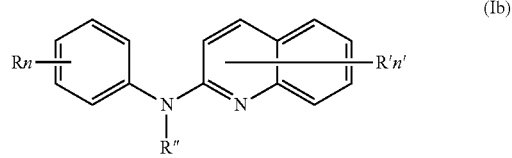

wherein:

R' and R" are as defined in formula (Ib), n is 1, and

R is a hydrogen atom or a ($C_1$-$C_3$)fluoroalkoxy group, or one of its pharmaceutically acceptable salt.

Still according to this particular embodiment, the present invention more particularly focuses on compounds of formula (Ib) wherein:

R is a hydrogen atom or a ($C_1$-$C_3$)fluoroalkoxy group,

R' is a hydrogen atom, a halogen atom or a ($C_1$-$C_4$)alkyl group,

R" is as defined in the formula (Ib), n' is 1 or 2 and is preferably 1, n is 1 or 2 and is preferably 1, or one of its pharmaceutically acceptable salt.

Still according to this particular embodiment, the present invention more particularly focuses on compounds of formula (IW)

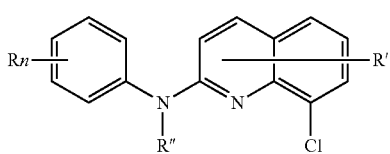

(Ib')

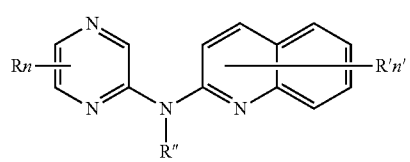

(Ie)

wherein:
R, R" and n are as defined in formula (Ib),
R' is as defined in formula (Ib),
with the proviso that R' is different from a methyl group in position 4 on the quinoline,
or one of its pharmaceutically acceptable salt.

Still according to this particular embodiment, the present invention more particularly focuses on compounds of formula (Ib")

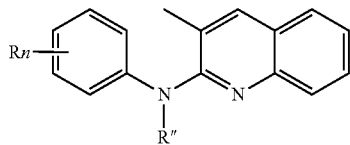

(Ib")

wherein:
R, R" and n are as defined in formula (Ib),
with the proviso that when n is 1, R is not a hydrogen atom, a methyl group in para of the bond linked to NR", a ethoxy group in para of the bond linked to NR", nor a fluorine atom in para of the bond linked to NR",
or one of its pharmaceutically acceptable salt.

According to another particular embodiment, the present invention encompasses compounds of formula (Ic), as such, wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a —NO$_2$ group, a —NR$_1$R$_2$ group and a $(C_1-C_3)$alkoxy group, $R_1$ and $R_2$ are independently a hydrogen atom or a $(C_1-C_3)$alkyl group, n is 1 or 2, and advantageously 1,
n' is 1 or 2,
R" is as defined in formula (Ic),
R' is a hydrogen atom or a group chosen among a $(C_1-C_3)$alkyl group, a —NO$_2$ group, a —NR$_1$R$_2$ group and a $(C_1-C_3)$alkoxy group,
with the proviso that
R and R' are not simultaneously a hydrogen atom,
R is not a bromine atom when R' is a hydrogen atom,
or one of its pharmaceutically acceptable salt.

Still according to this particular embodiment, the present invention more particularly focuses on compounds of formula (Ic), as such, wherein,
R is a hydrogen atom or a —NO$_2$ group,
n is 1,
R', R" and n' are as defined in formula (Ic), and
R' is preferably a $(C_1-C_3)$alkyl group or a hydrogen atom,
or one of its pharmaceutically acceptable salt.

The present invention further relates to a compound of formula (Ie) as defined above, as such wherein:
R, R', R" n and n' are as defined in formula (I),
with the proviso that
when R is a hydrogen atom, R' is not a bromine atom,
or one of its pharmaceutically acceptable salt.

According to another particular embodiment, the present invention encompasses compounds of formula (Io), as such, wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group and a $(C_1-C_3)$alkoxy group,
$R_1$ and $R_2$ are independently a hydrogen atom or a $(C_1-C_3)$alkyl group,
n is 1, 2 or 3,
n' is 1 or 2,
R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group,
R" is a hydrogen atom or a $(C_1-C_4)$alkyl group,
with the proviso that
when R is a hydrogen atom and n' is 1, R' is not a hydroxyl group,
or one of its pharmaceutically acceptable salt.

Still according to this particular embodiment, the present invention more particularly focuses on compounds of formula (Io'), as such, wherein

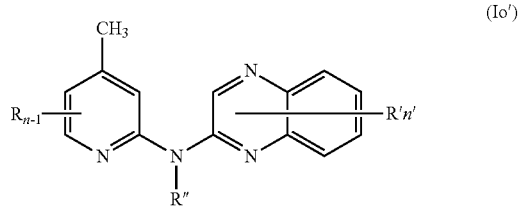

(Io')

wherein:
n is 1, 2 or 3,
n' is 1 or 2,
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group and a $(C_1-C_3)$alkoxy group, and is preferably a —NO$_2$ group, a hydrogen atom or a halogen atom,
R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a ($C_1$-$C_3$)alkoxy group and a —CN group, a ($C_1$-$C_3$)fluroralkyl group, and preferably is a hydrogen atom or a ($C_1$-$C_3$)fluoroalkyl group, $R_1$ and $R_2$ are as defined in formula (Io), R" is a hydrogen atom or a ($C_1$-$C_4$)alkyl group, or one of its pharmaceutically acceptable salt.

Among said compounds as such, compounds (1), (2), (5)-(8), (10)-(16), (18), (21)-(44), (46)-(75), (77)-(84), (86)-(119), (121), (124)-(130), (132), (135)-(141), (143)-(147), (149)-(168) and their pharmaceutically acceptable salts are of particular interest.

The present invention therefore extends to compounds (1), (2), (5)-(8), (10)-(16), (18), (21)-(44), (46)-(75), (77)-(84), (86)-(119), (121), (124)-(130), (132), (135)-(141), (143)-(147), (149)-(168) and their pharmaceutically acceptable salts, as such.

More preferably, compounds (8), (75), (77)-(84), (86)-(104), (109)-(117), (155)-(158) and their pharmaceutically acceptable salts are of particular interest.

The present invention therefore extends more preferably to compounds (8), (75), (77)-(84), (86)-(104), (109)-(117), (155)-(158) and their pharmaceutically acceptable salts, such as hydrobromide, tartrate, citrate, trifluoroacetate, ascorbate, hydrochloride, tartrate, triflate, maleate, mesylate, formate, acetate and fumarate.

Still more preferably, the present invention extends to compounds (75), (77), (78), (79), (80), (81), (82), (86), (87), (88), (90), (92), (96), (104), (109), (112), and their pharmaceutically acceptable salts, such as hydrobromide, tartrate, citrate, trifluoroacetate, ascorbate, hydrochloride, tartrate, triflate, maleate, mesylate, formate, acetate and fumarate.

The new compounds of the present invention, i.e. compounds of formulae (Ia), (Ic), (Io), (Ib), (Ib'), (Ib") and (Ie) and the specific compounds as listed above, are not only useful as agent for inhibiting, preventing or treating AIDS but can also be useful for inhibiting, preventing or treating premature aging and for inhibiting, preventing or treating cancer, and more particularly colorectal cancer, pancreatic cancer, lung cancer including non-small cell lung cancer, breast cancer, bladder cancer, gall bladder cancer, liver cancer, thyroid cancer, melanoma, uterine/cervical cancer, oesophageal cancer, kidney cancer, ovarian cancer, prostate cancer, head and neck cancer and stomach cancer, etc.

According to an aspect of the invention said compounds may be useful to inhibit, prevent and/or treat diseases with premature aging and that are likely related to an aberrant splicing of the nuclear lamin A gene. Among all, said disease may include Hutchinson Guilford Progeria Syndrome (HGPS), progeria, premature aging associated with HIV infection, muscular dystrophy, Charcot-Marie-Tooth disorder, Werner syndrome, but also atherosclerosis, insulin resistant type II diabetes, cataracts, osteoporosis and aging of the skin such as restrictive dermopathy.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) can be prepared according to scheme 1 below.

Scheme 1

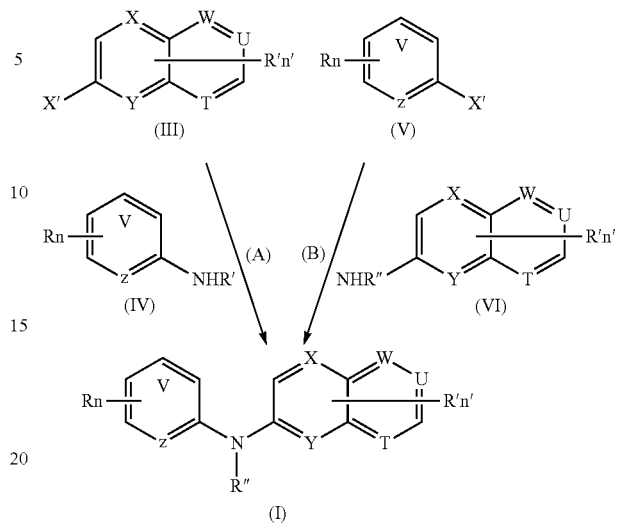

As appears in said scheme two routes are available for recovering a compound of formula (I) according to the present invention.

The synthesis is based on a coupling reaction alternatively starting from a halogeno-bicycle of formula (III), wherein X, Y, W, T, U, n', R' and R" are as defined above and X' is a chlorine atom or a bromine atom or from a chloro-monocycle of formula (V), wherein Z, V, n and R are as defined above and X' is a chlorine atom or a bromine atom.

According to route (A), the compound of formula (III) is placed in a protic solvent such as tert-butanol. The compound of formula (IV) is then added in a molar ratio ranging from 1 to 1.5 with respect to the compound of formula (III) in presence of an inorganic base, such as $Cs_2CO_3$ or $K_2CO_3$ in a molar ratio ranging from 1 and 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (III), and in the presence of a catalyst, such as $Pd(OAc)_2$ or $Pd_2dba_3$ in an amount ranging from 2 mol % and 10 mol % relative to the total amount of compound of formula (III). The reaction mixture can then be heated at a temperature ranging from 80 to 120° C., for example at 90° C. and stirred for a time ranging form 15 to 25 hours, for example during 20 hours under inert gas and for example argon. The reaction mixture can be concentrated under reduced pressure.

According to route (B) the compound of formula (V) is placed in a protic solvent such as tert-butanol. The compound of formula (VI) is then added in a molar ratio ranging from 1 to 1.5 with respect to the compound of formula (V) in presence of an inorganic base, such as $Cs_2CO_3$ or $K_2CO_3$ in a molar ratio ranging from 1 to 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (V), and in the presence of a catalyst, such as $Pd(OAc)_2$ or $Pd_2dba_3$ in an amount ranging from 2 mol % to 10 mol % relative to the total amount of compound of formula (V). The reaction mixture can then be heated at a temperature ranging from 80 to 120° C., for example at 90° C. and stirred for a time ranging form 15 to 25 hours, for example during 20 hours under inert gas and for example argon. The reaction mixture can be concentrated under reduced pressure.

The starting compounds of formula (III), (IV), (V) and (VI) are commercially available or can be prepared according to methods known to the person skilled in the art.

The chemical structures and spectroscopic data of some compounds of formula (I) of the invention are illustrated respectively in the following Table I and Table II.

TABLE I

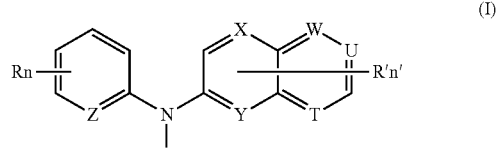

| | Formula (Ia) |
|---|---|
| 1 | 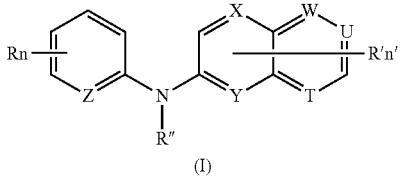 |
| 2 | 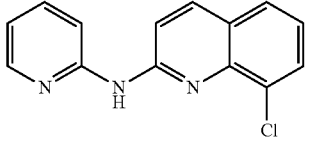 [SMILES: Clc1cccc2ccc(Nc3ccccn3)nc12] |
| 3 | 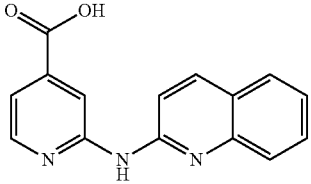 [SMILES: O=C(O)c1ccnc(Nc2ccc3ccccc3n2)c1] |
| 4 | 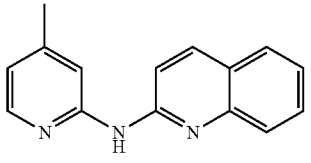 [SMILES: Cc1ccnc(Nc2ccc3ccccc3n2)c1] |
| 5 | 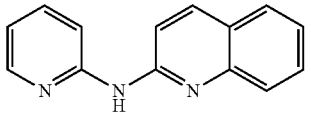 [SMILES: c1ccc(Nc2ccc3ccccc3n2)nc1] |
| 6 | 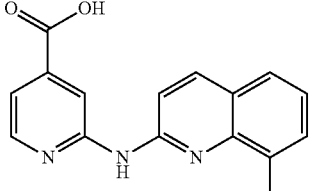 |

TABLE I-continued

| | |
|---|---|
| 7 | 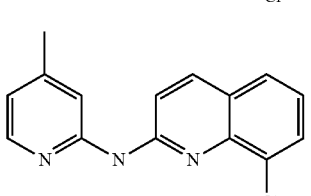 |
| 17 | 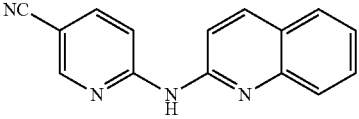 [SMILES: N#Cc1ccc(Nc2ccc3ccccc3n2)nc1] |
| 18 | 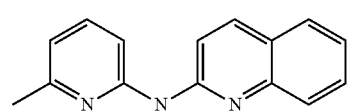 |
| 19 | 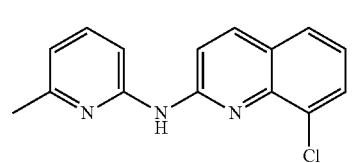 [SMILES: Cc1cccc(Nc2ccc3cccc(Cl)c3n2)n1] |
| 20 | 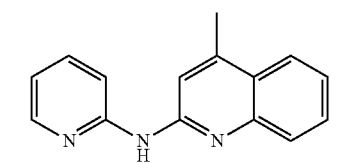 [SMILES: Cc1cc(Nc2ccccn2)nc2ccccc12] |
| 21 | 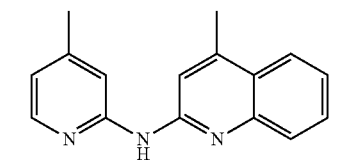 [SMILES: Cc1ccnc(Nc2cc(C)c3ccccc3n2)c1] |
| 22 | 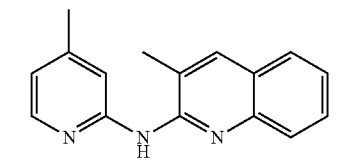 [SMILES: Cc1ccnc(Nc2nc3ccccc3cc2C)c1] |
| 23 | 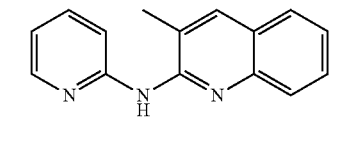 [SMILES: Cc1cc2ccccc2nc1Nc1ccccn1] |
| 24 | 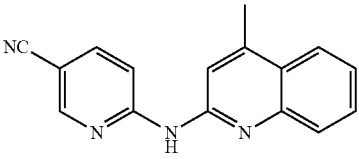 [SMILES: Cc1cc(Nc2ccc(C#N)cn2)nc2ccccc12] |

TABLE I-continued
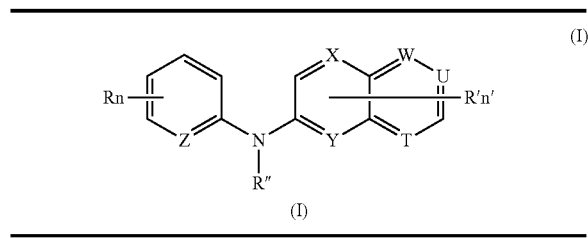
| 25 | 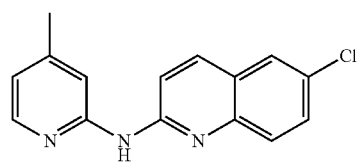 [SMILES: Cc1ccnc(Nc2ccc3cc(Cl)ccc3n2)c1] |
| --- | --- |
| 26 | 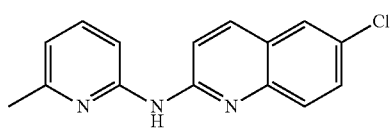 [SMILES: Cc1cccc(Nc2ccc3cc(Cl)ccc3n2)n1] |
| 27 | 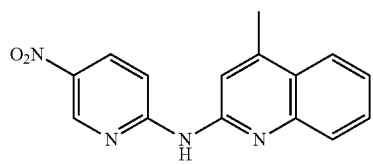 [SMILES: Cc1cc(Nc2ccc([N+](=O)[O-])cn2)nc2ccccc12] |
| 28 | 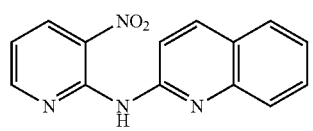 [SMILES: O=[N+]([O-])c1cccnc1Nc1ccc2ccccc2n1] |
| 29 | 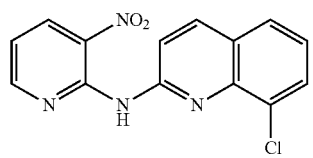 [SMILES: O=[N+]([O-])c1cccnc1Nc1ccc2cccc(Cl)c2n1] |
| 30 | 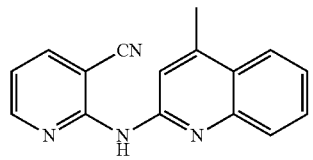 [SMILES: Cc1cc(Nc2ncccc2C#N)nc2ccccc12] |
| 31 | 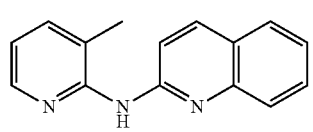 [SMILES: Cc1cccnc1Nc1ccc2ccccc2n1] |
| 32 | 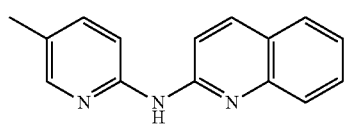 [SMILES: Cc1ccc(Nc2ccc3ccccc3n2)nc1] |
| 33 | 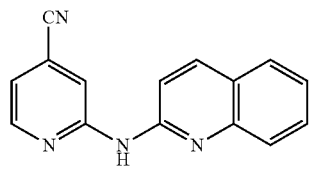 [SMILES: N#Cc1ccnc(Nc2ccc3ccccc3n2)c1] |
TABLE I-continued
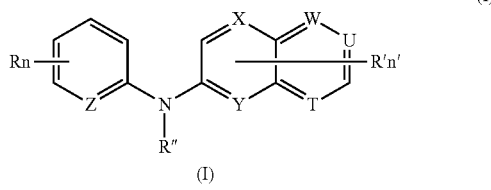
| 34 | 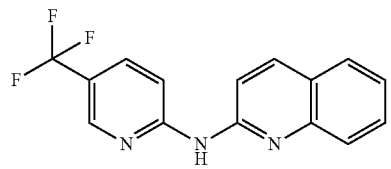 [SMILES: FC(F)(F)c1ccc(Nc2ccc3ccccc3n2)nc1] |
| --- | --- |
| 35 |  |
| 36 | 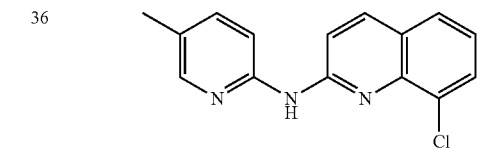 |
| 37 | 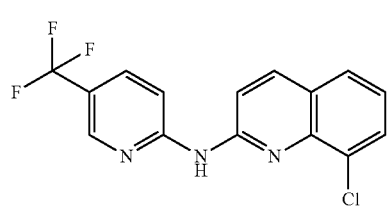 [SMILES: FC(F)(F)c1ccc(Nc2ccc3cccc(Cl)c3n2)nc1] |
| 38 | 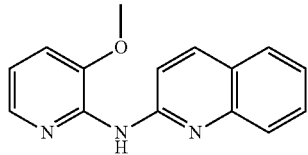 [SMILES: COc1cccnc1Nc1ccc2ccccc2n1] |
| 39 | 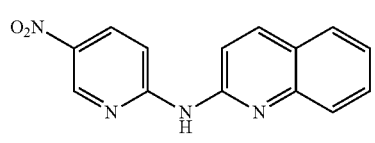 [SMILES: O=[N+]([O-])c1ccc(Nc2ccc3ccccc3n2)nc1] |
| 40 | 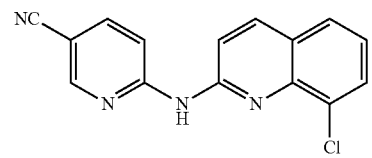 [SMILES: N#Cc1ccc(Nc2ccc3cccc(Cl)c3n2)nc1] |
| 41 | 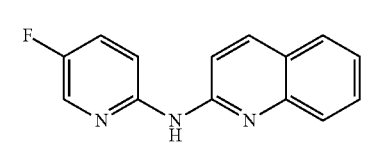 [SMILES: Fc1ccc(Nc2ccc3ccccc3n2)nc1] |

TABLE I-continued
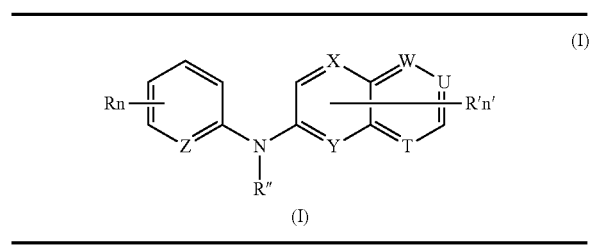
| 42 | 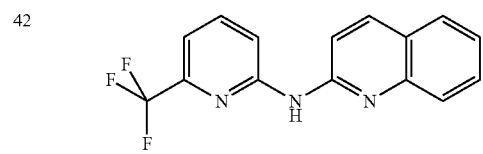 |
| 43 | 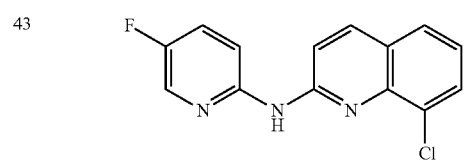 |
| 44 | 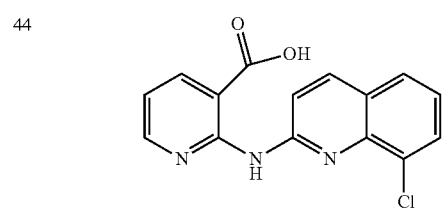 |
| 45 | 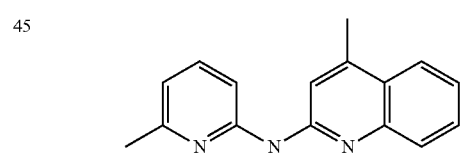 |
| 46 | 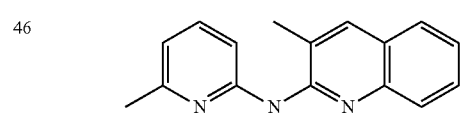 |
| 47 | 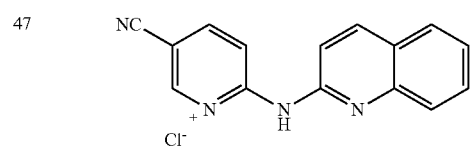 |
| 48 | 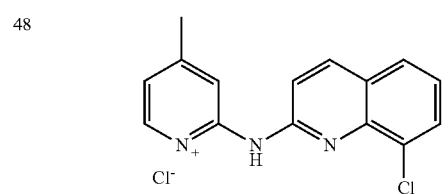 |
| 49 | 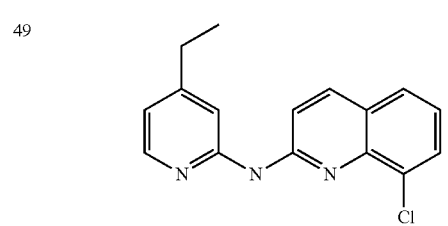 |
TABLE I-continued
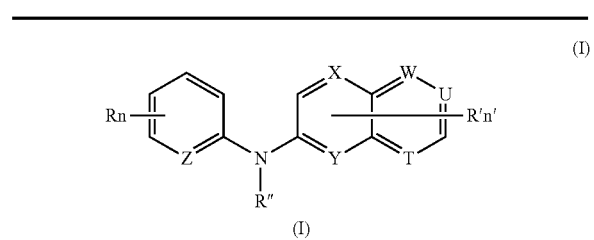
| 50 | 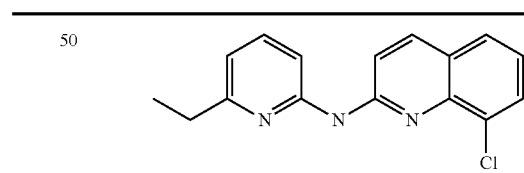 |
| 51 | 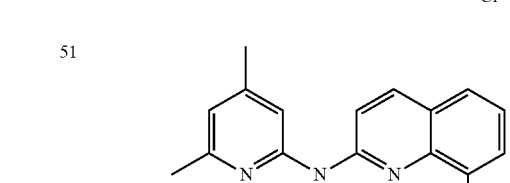 |
| 52 | 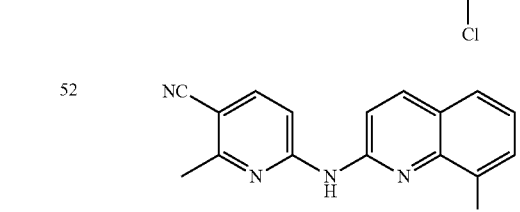 |
| 53 | 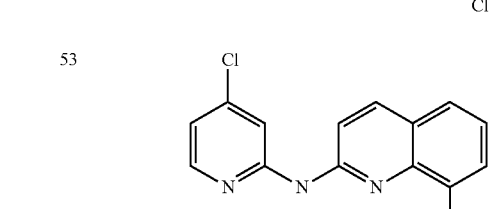 |
| 54 | 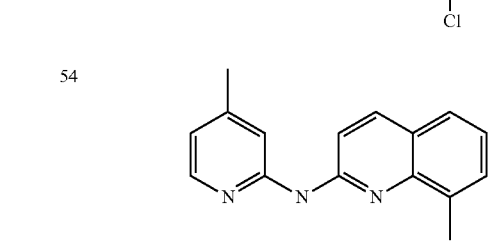 |
| 55 |  |
| 56 | 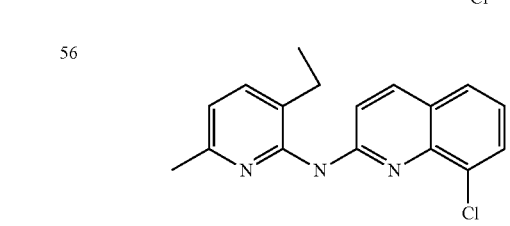 |

TABLE I-continued
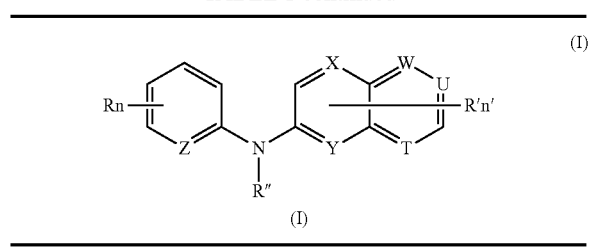
| 57 | 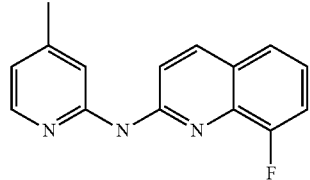 |
| 58 | 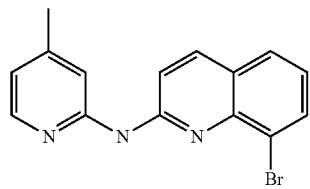 [SMILES: Cc1ccnc(Nc2ccc3cccc(F)c3n2)c1] |
| 59 | 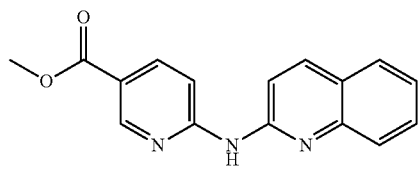 [SMILES: COC(=O)c1ccc(Nc2ccc3ccccc3n2)nc1] |
| 60 | 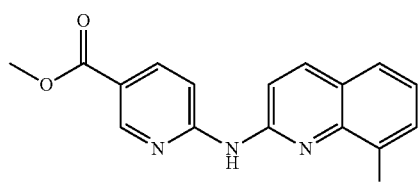 |
| 61 | 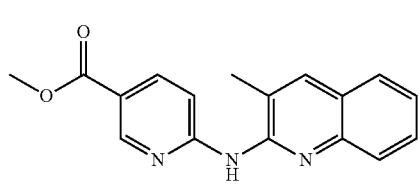 [SMILES: COC(=O)c1ccc(Nc2nc3ccccc3cc2C)nc1] |
| 62 | 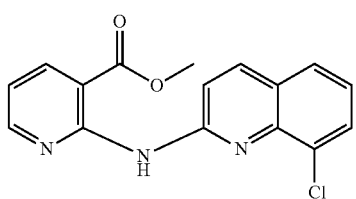 [SMILES: COC(=O)c1cccnc1Nc1ccc2cccc(Cl)c2n1] |
| 63 | 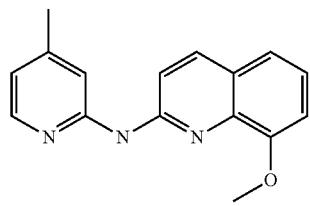 [SMILES: COc1cccc2ccc(Nc3cc(C)ccn3)nc12] |
TABLE I-continued
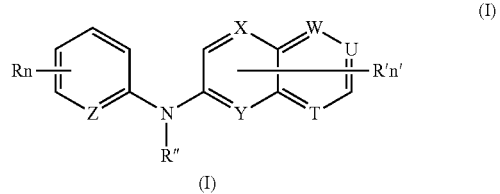
| 64 | 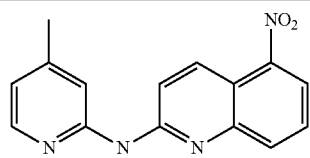 [SMILES: Cc1ccnc(Nc2ccc3c([N+](=O)[O-])cccc3n2)c1] |
| 65 | 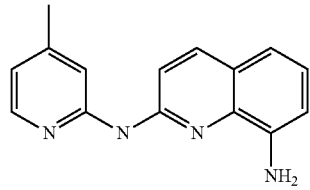 [SMILES: Cc1ccnc(Nc2ccc3cccc(N)c3n2)c1] |
| 66 | 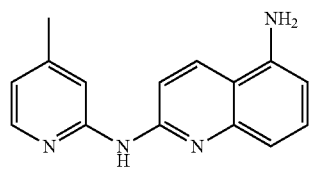 [SMILES: Cc1ccnc(Nc2ccc3c(N)cccc3n2)c1] |
| 67 | 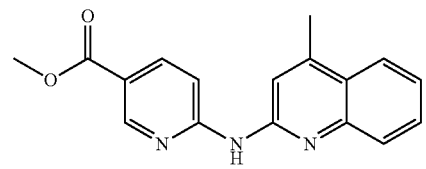 [SMILES: COC(=O)c1ccc(Nc2cc(C)c3ccccc3n2)nc1] |
| 68 | 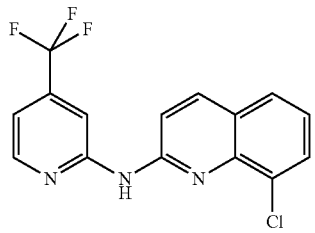 [SMILES: FC(F)(F)c1ccnc(Nc2ccc3cccc(Cl)c3n2)c1] |
| 69 | 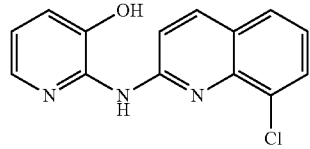 [SMILES: Oc1cccnc1Nc1ccc2cccc(Cl)c2n1] |
| 70 | 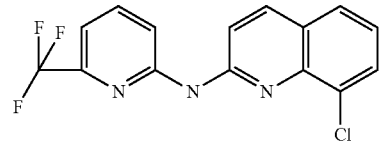 [SMILES: FC(F)(F)c1cccc(Nc2ccc3cccc(Cl)c3n2)n1] |
| 71 | 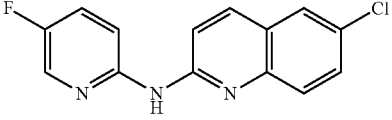 [SMILES: Fc1ccc(Nc2ccc3cc(Cl)ccc3n2)nc1] |

TABLE I-continued

Formula (I) with substituents as shown

| # | Structure description |
|---|---|
| 72 | 6-ethylpyridin-2-yl-NH-(3-methylquinolin-2-yl) |
| 73 | 5-fluoropyridin-2-yl-NH-(3-methylquinolin-2-yl) |
| 74 | 5-(trifluoromethyl)pyridin-2-yl-NH-(3-methylquinolin-2-yl) |
| 150 | 4-methylpyridin-2-yl-N-(8-nitroquinolin-2-yl) |
| 151 | 6-ethylpyridin-2-yl-N-(6-chloroquinolin-2-yl) |
| 152 | 5-methylpyridin-2-yl-N-(6-chloroquinolin-2-yl) |
| 153 | 5-(trifluoromethyl)pyridin-2-yl-N-(6-chloroquinolin-2-yl) |
| 154 | 3-amino-4-methylpyridin-2-yl-N-(8-chloroquinolin-2-yl) |

Formula (Ib)

| # | Structure description |
|---|---|
| 8 | 4-(trifluoromethoxy)phenyl-NH-(quinolin-2-yl) |
| 75 | 4-(dimethylamino)phenyl-NH-(8-chloroquinolin-2-yl) |
| 76 | 4-methoxyphenyl-NH-(quinolin-2-yl) |
| 77 | 4-methoxyphenyl-NH-(8-chloroquinolin-2-yl) |
| 78 | 4-(trifluoromethoxy)phenyl-NH-(4-methylquinolin-2-yl) |
| 79 | 4-methoxyphenyl-NH-(3-methylquinolin-2-yl) |
| 80 | 5-(trifluoromethoxy)pyridin-2-yl-NH-(3-methylquinolin-2-yl) |
| 81 | 4-(dimethylamino)phenyl-NH-(3-methylquinolin-2-yl) |
| 82 | 4-(trifluoromethoxy)-2-methylphenyl-NH-(quinolin-2-yl) |
| 83 | 3-(trifluoromethoxy)phenyl-NH-(quinolin-2-yl) |

TABLE I-continued
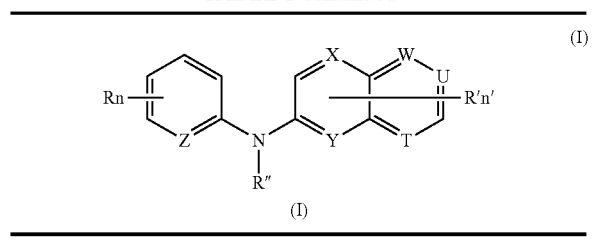

TABLE I-continued
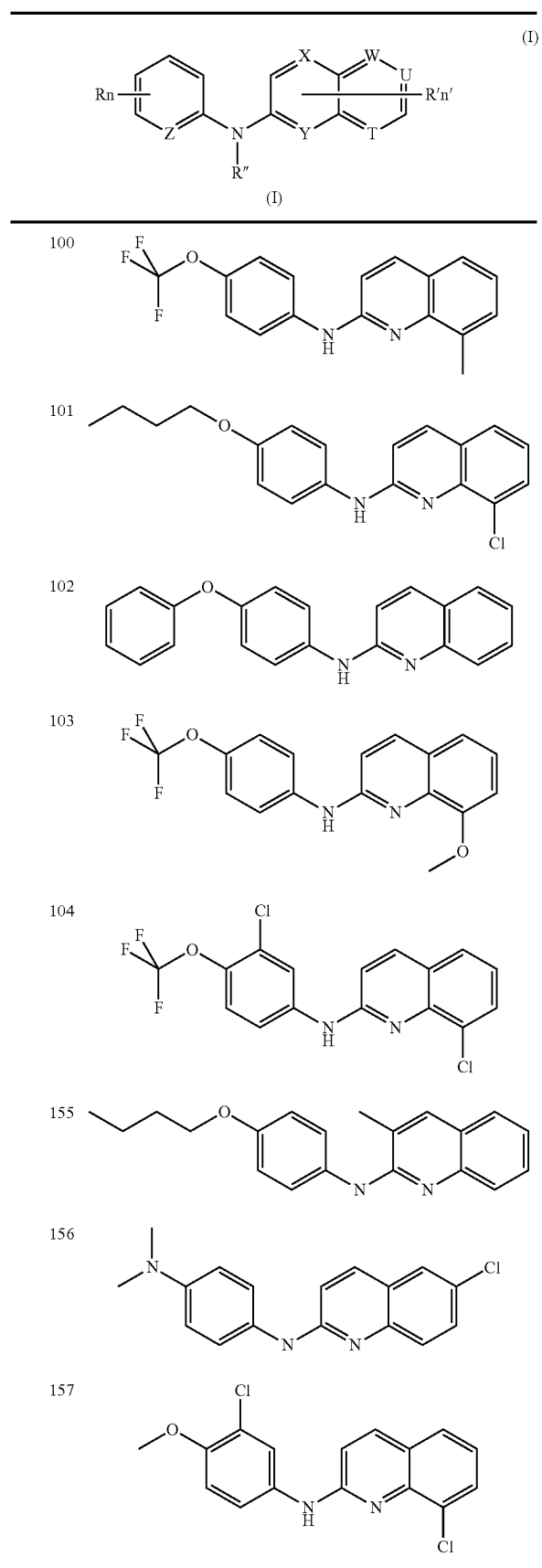
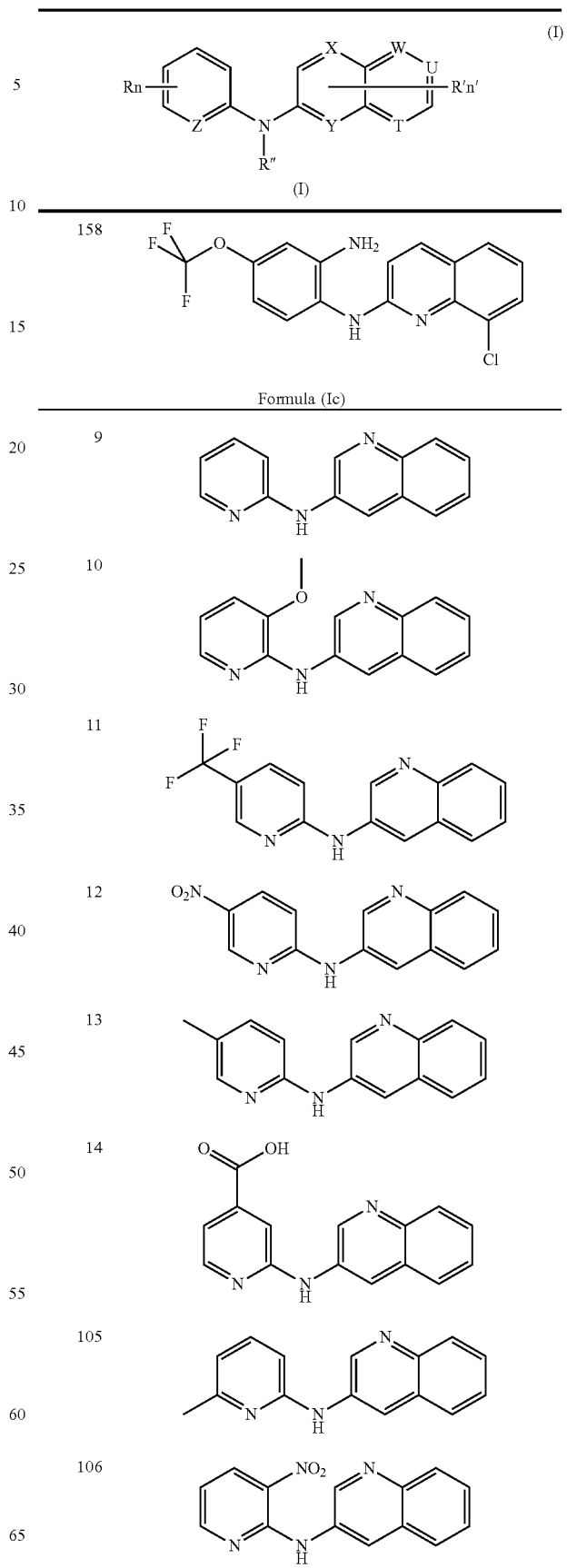

TABLE I-continued
| | | |
|---|---|---|
| 159 | 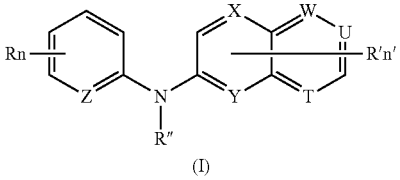 Formula (Id) | |
| 15 | 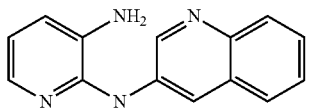 [SMILES: Nc1cccnc1Nc1cnc2ccccc2c1] | |
| 16 | 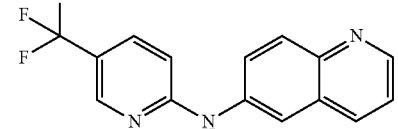 | |
| 107 | 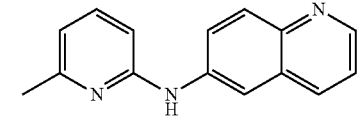 [SMILES: Cc1cccc(Nc2ccc3ncccc3c2)n1] | |
| 108 | 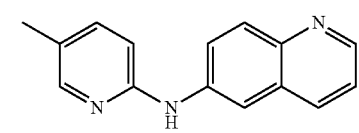 [SMILES: Cc1ccc(Nc2ccc3ncccc3c2)nc1] Formula (Ie) | |
| 109 | 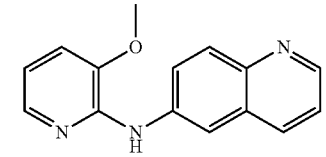 [SMILES: COc1cccnc1Nc1ccc2ncccc2c1] | |
| 110 | 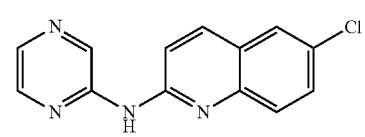 [SMILES: Clc1ccc2nc(Nc3cnccn3)ccc2c1] | |
| 111 | 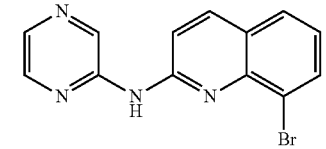 [SMILES: Brc1cccc2ccc(Nc3cnccn3)nc12] | |
| 112 | 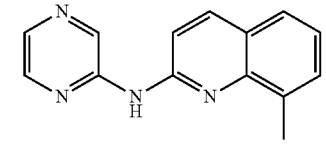 [SMILES: Cc1cccc2ccc(Nc3cnccn3)nc12] | |
TABLE I-continued
| | | |
|---|---|---|
| 113 | 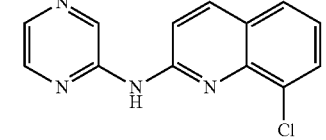 | |
| 114 | 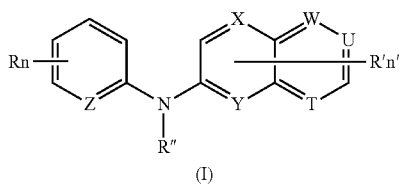 | |
| 115 | 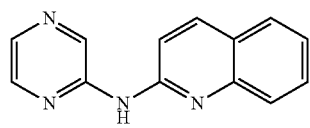 [SMILES: c1ccc2nc(Nc3cnccn3)ccc2c1] | |
| 116 | 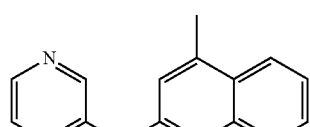 | |
| 117 | 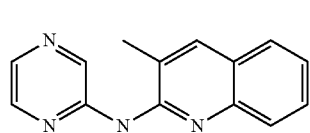 Formula (If) | |
| 118 | 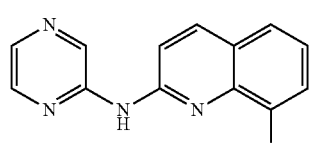 Formula (Ig) | |
| 119 | 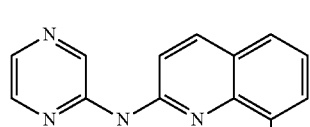 | |
| 120 | 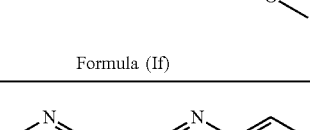 | |

TABLE I-continued
| | | (I) |
|---|---|---|
Formula (Ih)
| 121 | 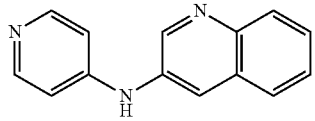 [SMILES: c1ccc2ncc(Nc3ccncc3)cc2c1] |
|---|---|
Formula (Ii)
| 122 | 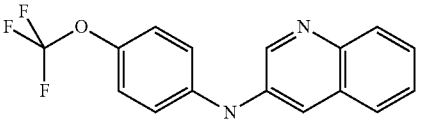 [SMILES: FC(F)(F)Oc1ccc(Nc2cnc3ccccc3c2)cc1] |
|---|---|
| 123 | 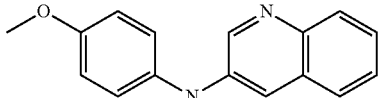 |
Formula (Ij)
| 124 | 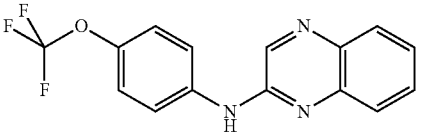 [SMILES: FC(F)(F)Oc1ccc(Nc2cnc3ccccc3n2)cc1] |
|---|---|
| 125 | 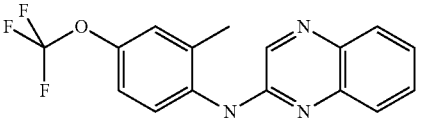 [SMILES: Cc1cc(OC(F)(F)F)ccc1Nc1cnc2ccccc2n1] |
| 126 | 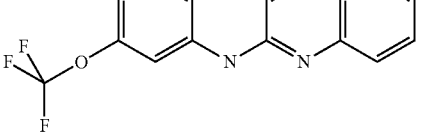 |
| 127 | 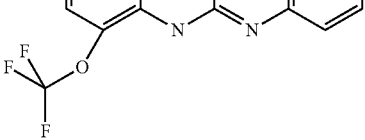 |
Formula (Ik)
| 128 | 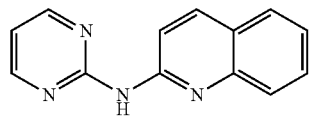 [SMILES: c1cnc(Nc2ccc3ccccc3n2)nc1] |
|---|---|
TABLE I-continued
| | | (I) |
|---|---|---|
| 129 | 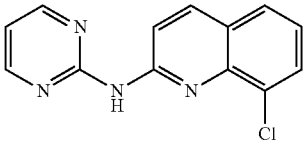 [SMILES: Clc1cccc2ccc(Nc3ncccn3)nc12] |
|---|---|
| 130 | 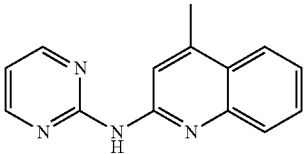 [SMILES: Cc1cc(Nc2ncccn2)nc2ccccc12] |
Formula (Il)
| 131 | 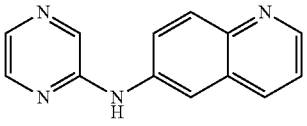 [SMILES: c1cnc2ccc(Nc3cnccn3)cc2c1] |
|---|---|
Formula (Im)
| 132 | 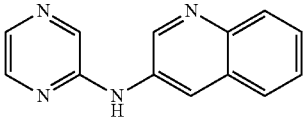 [SMILES: c1ccc2ncc(Nc3cnccn3)cc2c1] |
|---|---|
Formula (Io)
| 135 | 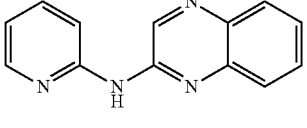 |
|---|---|
| 136 | 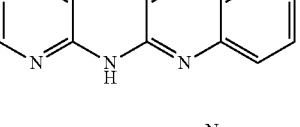 |
| 137 | 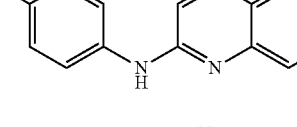 |
| 138 | 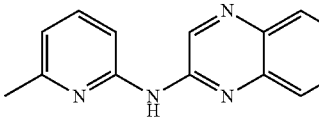 |

TABLE I-continued

| # | Structure |
|---|---|
| 139 | 4-methyl-3-(trifluoromethyl)pyridin-2-yl quinoxalin-2-yl amine |
| 140 | 3,5-dichloro-4-methylpyridin-2-yl quinoxalin-2-yl amine |
| 141 | 4-methyl-3-nitropyridin-2-yl quinoxalin-2-yl amine |
| 160 | 4-methylpyridin-2-yl 6-chloroquinoxalin-2-yl amine |
| 161 | 4-ethylpyridin-2-yl quinoxalin-2-yl amine |
| 162 | 5-bromo-4-methylpyridin-2-yl quinoxalin-2-yl amine |
| 163 | 4,6-dimethylpyridin-2-yl quinoxalin-2-yl amine |
| 164 | 4-(hydroxymethyl)pyridin-2-yl quinoxalin-2-yl amine |
| 165 | 4-methyl-5-nitropyridin-2-yl quinoxalin-2-yl amine |
| 142 | pyrimidin-2-yl quinoxalin-2-yl amine (Formula Ip) |
| 143 | N,N-dimethyl-7-[(4-trifluoromethoxyphenyl)amino]quinolin-4-amine (Formula Iq) |
| 144 | 4-morpholino-7-[(4-trifluoromethoxyphenyl)amino]quinoline |
| 166 | 4-(4-methylpiperazin-1-yl)-7-[(4-methoxyphenyl)amino]quinoline |
| 167 | 4-methoxy-7-[(4-trifluoromethoxyphenyl)amino]quinoline |

TABLE I-continued

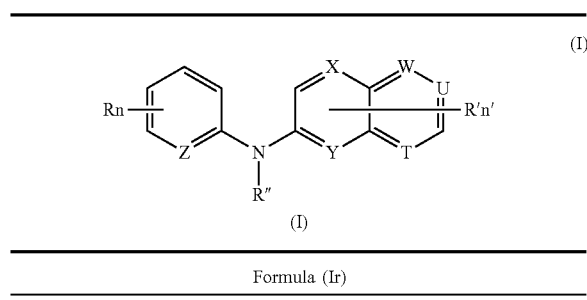

Formula (Ir)

| | |
|---|---|
| 145 | 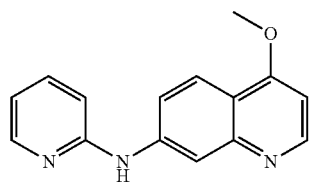 [SMILES: COc1ccnc2cc(Nc3ccccn3)ccc12] |
| 146 | 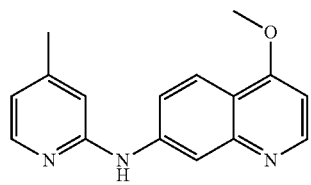 [SMILES: COc1ccnc2cc(Nc3cc(C)ccn3)ccc12] |
| 147 | 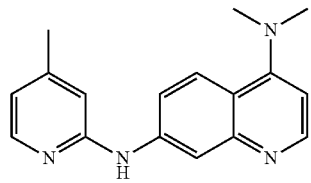 [SMILES: Cc1ccnc(Nc2ccc3c(N(C)C)ccnc3c2)c1] |

TABLE I-continued

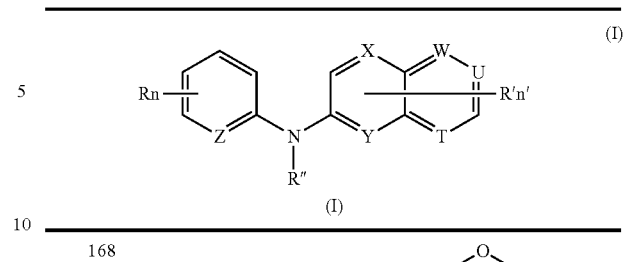

| | |
|---|---|
| 168 | 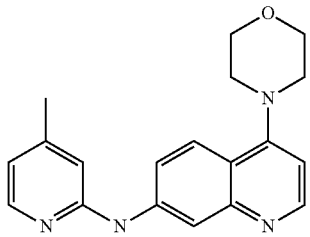 [SMILES: Cc1ccnc(Nc2ccc3c(N4CCOCC4)ccnc3c2)c1] |

Formula (Iee)

| | |
|---|---|
| 148 | 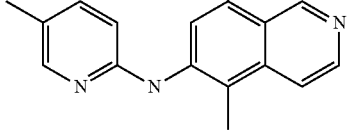 |
| 149 | 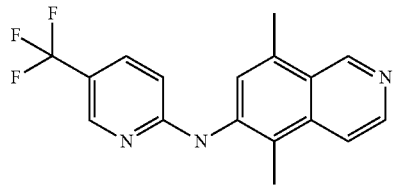 [SMILES: Cc1cc(Nc2ccc(C(F)(F)F)cn2)c(C)c2ccncc12] |

TABLE II

| Ex | Characterizations |
|---|---|
| 1 | MS (ESI) [M + H]$^+$ = 256 |
| 2 | $^1$H NMR (300 MHz, D$_2$O) δ 8.31 (d, J = 5.1, 1H), 8.21 (d, J = 9.3, 1H), 7.60 (d, J = 7.5, 3H), 7.34 (dd, J = 6.2, 15.6, 2H), 7.18 (s, 1H), 6.99 (d, J = 9.1, 1H)<br>MS (ESI) [M + H]$^+$ = 266 |
| 5 | MS (ESI) [M + H]$^+$ = 300 |
| 6 | $^1$H NMR (300 MHz, DMSO) δ 10.23 (s, 1H), 8.96 (s, 1H), 8.18 (d, J = 8.8, 2H), 7.78 (dd, J = 7.7, 13.7, 2H), 7.46 (d, J = 8.9, 1H), 7.31 (t, J = 7.8, 1H), 6.86 (d, J = 4.3, 1H), 2.37 (s, 3H).<br>$^{13}$C NMR (75 MHz, DMSO) δ 153.63, 153.61, 148.37, 147.32, 142.65, 137.52, 129.68, 129.47, 126.82, 125.06, 123.26, 118.36, 115.10, 113.31, 21.24.<br>MS (ESI) [M + H]$^+$ = 270 |
| 7 | $^1$H NMR (300 MHz, DMSO) δ 10.71 (s, 1H), 8.71 (d, J = 1.4, 1H), 8.62 (d, J = 8.9, 1H), 8.24 (d, J = 8.9, 1H), 8.17 (dd, J = 1.9, 8.9, 1H), 7.89-7.74 (m, 2H), 7.66 (dd, J = 7.9, 14.2, 2H), 7.42 (t, J = 7.3, 1H).<br>$^{13}$C NMR (75 MHz, DMSO) δ 156.09, 152.40, 152.11, 146.24, 141.07, 137.83, 129.87, 127.67, 126.78, 124.50, 124.21, 118.04, 114.49, 111.67, 100.12.<br>MS (ESI) [M + H]$^+$ = 247 |
| 8 | $^1$H NMR (300 MHz, CDCl$_3$) δ 7.92 (d, J = 8.9, 1H), 7.79 (d, J = 8.4, 1H), 7.65 (t, J = 7.7, 3H), 7.59 (dd, J = 7.1, 8.3, 1H), 7.31 (t, J = 7.0, 1H), 7.20 (d, J = 8.5, 2H), 6.88 (d, J = 8.9, 1H), 6.80 (s, 1H)<br>$^{13}$C NMR (75 MHz, CDCl$_3$) δ 153.88, 147.62, 144.35, 139.26, 138.11, 130.13, 127.65, 127.12, 124.43, 123.70, 122.20, 120.95, 112.25.<br>MS (ESI) [M + H]$^+$ = 305 |
| 10 | $^1$H NMR (300 MHz, CDCl$_3$) δ 9.10 (d, J = 2.5, 1H), 8.83 (d, J = 2.6, 1H), 8.02 (d, J = 7.9, 1H), 7.94 (dd, J = 1.3, 5.0, 1H), 7.85-7.79 (m, 1H), 7.52 (pd, J = 1.5, 6.9, 2H), 7.33 (s, 1H), 7.04 (dd, J = 1.2, 7.9, 1H), 6.81 (dd, J = 5.1, 7.9, 1H), 3.95 (s, 3H) |
| 11 | MS (ESI) [M + H]$^+$ = 290 |
| 12 | $^1$H NMR (300 MHz, CDCl$_3$) δ 9.18 (d, J = 2.7, 1H), 8.86 (d, J = 2.5, 1H), 8.56 (d, J = 2.3, 1H), 8.33 (dd, J = 2.7, 9.2, 1H), 8.08 (d, J = 8.5, 1H), 7.83 (d, J = 8.5, 1H), 7.71-7.63 (m, 2H), 7.57 (t, J = 7.4, 2H), 6.82 (d, J = 9.1, 1H) |

TABLE II-continued

| Ex | Characterizations |
|---|---|
| 13 | $^1$H NMR (300 MHz, CDCl$_3$) δ 8.83 (d, J = 2.6, 1H), 8.37 (d, J = 2.3, 1H), 8.00 (d, J = 8.2, 1H), 7.71 (d, J = 7.7, 1H), 7.59-7.51 (m, 1H), 7.46 (dd, J = 7.3, 15.1, 2H), 6.71 (d, J = 8.3, 1H), 6.67 (d, J = 7.4, 1H), 2.49 (s, 3H)<br>$^{13}$C NMR (75 MHz, CDCl$_3$) δ 157.13, 154.59, 145.81, 144.43, 138.78, 134.54, 129.22, 128.86, 127.41, 127.27, 121.48, 115.41, 106.50, 24.18.<br>MS (ESI) [M + H]$^+$ = 236 |
| 14 | MS (ESI) [M + H]$^+$ = 266 |
| 15 | MS (ESI) [M + H]$^+$ = 290 |
| 16 | $^1$H NMR (300 MHz, CDCl$_3$) δ 8.77 (dd, J = 1.5, 4.2, 1H), 8.04 (dd, J = 4.7, 8.7, 2H), 7.92 (d, J = 2.4, 1H), 7.59 (dd, J = 2.5, 9.1, 1H), 7.47 (t, J = 7.8, 1H), 7.35 (dd, J = 4.2, 8.3, 1H), 6.87 (s, 1H), 6.81 (d, J = 8.2, 1H), 6.70 (d, J = 7.4, 1H), 2.50 (s, 3H)<br>MS (ESI) [M + H]$^+$ = 236 |
| 18 | $^1$H NMR (300 MHz, CDCl$_3$) δ 8.53 (d, J = 59.9, 2H), 7.76 (d, J = 8.6, 1H), 7.58 (t, J = 8.3, 2H), 7.42 (d, J = 7.8, 1H), 7.09 (t, J = 7.7, 1H), 6.95 (d, J = 8.7, 1H), 6.71 (d, J = 7.3, 1H), 2.38 (s, 3H) |
| 21 | $^1$H NMR (300 MHz, CDCl$_3$) δ 8.78 (s, 1H), 8.13 (d, J = 5.1, 1H), 7.89 (d, J = 8.3, 1H), 7.79 (s, 1H), 7.63 (d, J = 8.0, 1H), 7.56 (d, J = 7.3, 1H), 7.38 (s, 1H), 7.33 (t, J = 7.5, 1H), 6.79 (d, J = 4.9, 1H), 2.44 (s, 6H) |
| 22 | $^1$H NMR (300 MHz, CDCl$_3$) δ 8.95 (d, J = 8.4, 1H), 8.28 (d, J = 5.7, 1H), 7.87 (d, J = 8.3, 1H), 7.78 (s, 1H), 7.76-7.70 (m, 1H), 7.62 (d, J = 8.0, 1H), 7.60-7.52 (m, 1H), 7.42 (s, 1H), 7.32 (t, J = 7.4, 1H), 6.95 (dd, J = 5.1, 6.5, 1H), 2.45 (s, 3H) |
| 23 | $^1$H NMR (300 MHz, CDCl$_3$) δ 8.64 (d, J = 8.4, 1H), 8.55 (d, J = 2.1, 1H), 8.03 (s, 1H), 7.90 (d, J = 8.5, 4H), 7.66 (t, J = 7.6, 1H), 7.44 (t, J = 7.6, 1H), 7.06 (s, 1H), 2.67 (s, 4H) |
| 24 | $^1$H NMR (300 MHz, CDCl$_3$) δ 9.09 (d, J = 8.9, 1H), 8.53 (d, J = 1.7, 1H), 7.94 (dd, J = 2.2, 8.9, 1H), 7.92-7.84 (m, 2H), 7.67 (d, J = 8.6, 2H), 7.65-7.58 (m, 1H), 7.40 (t, J = 7.4, 1H), 2.49 (s, 3H) |
| 25 | $^1$H NMR (300 MHz, CDCl$_3$) δ 8.16 (d, J = 5.2, 1H), 8.10 (s, 1H), 7.90 (d, J = 8.8, 1H), 7.79 (d, J = 9.0, 1H), 7.66 (d, J = 2.2, 1H), 7.55 (dd, J = 2.3, 8.9, 1H), 7.39 (d, J = 9.0, 1H), 6.79 (d, J = 5.2, 1H), 2.42 (s, 3H)<br>MS (ESI) [M + H]$^+$ = 270 |
| 26 | $^1$H NMR (300 MHz, CDCl$_3$) δ 8.06 (d, J = 8.3, 1H), 7.70 (d, J = 9.0, 1H), 7.64 (d, J = 8.9, 1H), 7.49 (t, J = 7.9, 2H), 7.40 (dd, J = 2.3, 8.9, 1H), 7.18 (d, J = 8.9, 1H), 6.68 (d, J = 7.4, 1H), 2.38 (s, 3H)<br>MS (ESI) [M + H]$^+$ = 270 |
| 27 | $^1$H NMR (300 MHz, CDCl$_3$) δ 9.17 (d, J = 2.5, 1H), 8.71 (s, 1H), 8.49 (dd, J = 2.6, 9.0, 1H), 7.99 (s, 1H), 7.93 (d, J = 8.9, 2H), 7.74-7.64 (m, 1H), 7.48 (dd, J = 4.2, 11.4, 1H), 7.09 (s, 1H), 2.71 (s, 3H) |
| 28 | $^1$H NMR (300 MHz, CDCl$_3$) δ 8.64-8.51 (m, 3H), 8.18 (d, J = 9.0, 1H), 7.93 (d, J = 8.4, 1H), 7.79 (d, J = 8.1, 1H), 7.73-7.64 (m, 1H), 7.51-7.41 (m, 1H), 7.00 (dd, J = 4.6, 8.2, 1H), 6.75 (dd, J = 4.6, 8.3, 0H) |
| 29 | $^1$H NMR (300 MHz, CDCl$_3$) δ 10.77 (s, 1H), 8.60 (s, 3H), 8.19 (d, J = 8.2, 1H), 7.76 (dd, J = 6.6, 25.5, 2H), 7.38 (d, J = 7.2, 1H), 7.04 (d, J = 4.4, 1H) |
| 30 | $^1$H NMR (300 MHz, CDCl$_3$) δ 8.46 (dd, J = 1.9, 5.0, 1H), 7.87 (dd, J = 2.0, 7.6, 1H), 7.82 (d, J = 7.3, 1H), 7.60 (t, J = 7.3, 2H), 7.43-7.33 (m, 1H), 6.90 (dd, J = 5.0, 7.6, 1H), 2.64 (s, 3H) |
| 31 | $^1$H NMR (300 MHz, CDCl$_3$) δ 8.44 (d, J = 9.1, 1H), 8.17 (d, J = 4.8, 1H), 8.03 (d, J = 9.1, 1H), 7.78 (d, J = 8.4, 1H), 7.68 (d, J = 8.0, 1H), 7.62-7.54 (m, 1H), 7.39 (d, J = 7.3, 1H), 7.32 (t, J = 7.5, 1H), 6.82 (dd, J = 5.0, 7.3, 1H), 2.31 (s, 3H)<br>MS (ESI) [M + H]$^+$ = 236 |
| 32 | $^1$H NMR (300 MHz, CDCl$_3$) δ 8.23 (d, J = 8.5, 1H), 8.10 (s, 1H), 7.91 (d, J = 8.9, 1H), 7.82 (d, J = 8.4, 1H), 7.62 (d, J = 8.3, 1H), 7.56 (d, J = 7.3, 1H), 7.50 (dd, J = 1.8, 8.5, 1H), 7.37-7.24 (m, 2H), 2.26 (s, 3H)<br>MS (ESI) [M + H]$^+$ = 236 |
| 33 | $^1$H NMR (300 MHz, CDCl$_3$) δ 8.87 (s, 1H), 8.32 (d, J = 5.0, 1H), 7.95 (d, J = 8.8, 1H), 7.84 (d, J = 8.3, 1H), 7.60 (dd, J = 7.4, 14.1, 2H), 7.32 (t, J = 7.5, 1H), 7.04 (dd, J = 5.0, 9.0, 2H)<br>MS (ESI) [M + H]$^+$ = 247 |
| 34 | $^1$H NMR (300 MHz, CDCl$_3$) δ 8.52 (s, 1H), 8.45 (d, J = 8.6, 1H), 8.01 (d, J = 8.8, 1H), 7.87 (dd, J = 2.5, 8.5, 2H), 7.72-7.56 (m, 2H), 7.39 (d, J = 9.0, 2H)<br>MS (ESI) [M + H]$^+$ = 290 |
| 35 | $^1$H NMR (300 MHz, CDCl$_3$) δ 8.32 (d, J = 9.1, 1H), 8.07 (d, J = 4.8, 1H), 7.93 (d, J = 9.1, 1H), 7.59 (t, J = 7.9, 1H), 7.52 (d, J = 8.0, 1H), 7.36 (d, J = 7.2, 1H), 7.14 (t, J = 7.8, 1H), 6.77 (dd, J = 5.0, 7.3, 1H), 2.29 (s, 3H)<br>MS (ESI) [M + H]$^+$ = 270 |
| 36 | $^1$H NMR (300 MHz, CDCl$_3$) δ 8.70 (d, J = 7.2, 1H), 8.01 (s, 1H), 7.82 (d, J = 8.9, 1H), 7.62 (d, J = 7.6, 1H), 7.53 (dd, J = 1.8, 8.6, 1H), 7.46 (d, J = 7.9, 1H), 7.12 (t, J = 7.8, 1H), 7.05 (d, J = 8.8, 1H), 2.21 (s, 3H)<br>MS (ESI) [M + H]$^+$ = 270 |
| 37 | $^1$H NMR (300 MHz, CDCl$_3$) δ 9.08 (d, J = 8.5, 1H), 8.55 (s, 1H), 8.36 (s, 1H), 8.02 (d, J = 8.1, 2H), 7.77 (d, J = 7.2, 1H), 7.62 (d, J = 7.6, 1H), 7.35-7.24 (m, 1H), 7.12 (d, J = 8.8, 1H)<br>MS (ESI) [M + H]$^+$ = 324 |
| 38 | $^1$H NMR (300 MHz, CDCl$_3$) δ 8.69 (d, J = 9.1, 1H), 7.97 (d, J = 9.1, 1H), 7.80-7.74 (m, 1H), 7.70 (d, J = 8.4, 1H), 7.59 (d, J = 8.0, 1H), 7.54-7.45 (m, 1H), 7.22 (t, J = 7.5, 1H), 6.87 (d, J = 7.9, 1H), 6.68 (dd, J = 5.0, 7.9, 1H), 3.73 (s, 3H)<br>MS (ESI) [M + H]$^+$ = 252 |

TABLE II-continued

| Ex | Characterizations |
|---|---|
| 39 | $^1$H NMR (300 MHz, CDCl$_3$) δ 8.57 (d, J = 29.4, 1H), 7.80 (d, J = 8.8, 1H), 7.66 (t, J = 6.7, 2H), 7.46 (d, J = 7.9, 1H), 7.14 (t, J = 7.8, 1H), 7.06 (d, J = 8.8, 1H), 6.79 (d, J = 7.3, 1H), 2.73 (dd, J = 7.6, 15.2, 2H), 1.28 (t, J = 7.7, 3H) |
| 40 | $^1$H NMR (300 MHz, DMSO) δ 9.75 (s, 1H), 9.12 (d, J = 2.3, 1H), 8.50 (d, J = 2.2, 1H), 8.48 (s, 1H), 8.13 (s, 1H), 7.83 (s, 1H), 7.80 (s, 1H), 7.64 (t, J = 7.7, 1H), 7.45 (t, J = 7.8, 1H) |
| 41 | $^1$H NMR (300 MHz, CDCl$_3$) δ 8.52 (dd, J = 2.8, 8.6, 1H), 8.35 (s, 1H), 8.15 (d, J = 2.3, 1H), 7.94 (d, J = 8.8, 1H), 7.84 (d, J = 8.2, 1H), 7.65 (d, J = 7.8, 1H), 7.59 (d, J = 7.2, 1H), 7.50-7.40 (m, 1H), 7.33 (t, J = 7.4, 1H), 7.11 (d, J = 8.9, 1H)<br>MS (ESI) [M + H]$^+$ = 240 |
| 42 | $^1$H NMR (300 MHz, CDCl$_3$) δ 8.55 (d, J = 6.8, 1H), 8.01 (d, J = 8.9, 2H), 7.82 (dd, J = 9.1, 17.3, 2H), 7.69 (d, J = 8.0, 1H), 7.63 (t, J = 7.6, 1H), 7.37 (t, J = 7.5, 1H), 7.32-7.18 (m, 2H)<br>MS (ESI) [M + H]$^+$ = 290 |
| 43 | $^1$H NMR (300 MHz, DMSO) δ 10.41 (s, 1H), 9.08 (dd, J = 4.1, 9.3, 1H), 8.31 (d, J = 2.9, 1H), 8.20 (d, J = 8.9, 1H), 7.88-7.70 (m, 3H), 7.44 (d, J = 8.9, 1H), 7.32 (t, J = 7.8, 1H)<br>$^{13}$C NMR (75 MHz, DMSO) δ 156.30, 153.32, 153.04, 150.17, 142.55, 137.73, 135.06, 134.74, 129.58, 129.49, 126.86, 125.29, 125.14, 125.04, 123.36, 114.91, 113.36.<br>MS (ESI) [M + H]$^+$ = 274 |
| 44 | $^1$H NMR (300 MHz, CDCl$_3$) δ 11.09 (s, 1H), 8.78 (d, J = 9.0, 1H), 8.42 (dd, J = 1.9, 4.7, 1H), 8.28 (dd, J = 1.9, 7.8, 1H), 8.11 (d, J = 9.1, 1H), 7.73 (d, J = 7.5, 1H), 7.65 (d, J = 8.1, 1H), 7.27 (dd, J = 6.4, 9.2, 1H), 6.88 (dd, J = 4.8, 7.8, 1H)<br>MS (ESI) [M + H]$^+$ = 300 |
| 46 | $^1$H NMR (300 MHz, CDCl$_3$) δ 8.59 (d, J = 8.3, 1H), 7.73 (d, J = 8.3, 1H), 7.57 (s, 1H), 7.51 (t, J = 7.9, 1H), 7.43 (t, J = 9.2, 2H), 7.17 (t, J = 7.4, 1H), 6.67 (d, J = 7.4, 1H), 2.36 (s, 3H), 2.28 (s, 3H) |
| 47 | $^1$H NMR (300 MHz, MeOD) δ 8.99 (s, 1H), 8.76 (d, J = 9.2, 1H), 8.32 (d, J = 8.7, 1H), 8.22 (d, J = 8.6, 1H), 8.11 (d, J = 7.8, 1H), 8.01 (t, J = 7.1, 1H), 7.76 (t, J = 7.4, 1H), 7.55-7.43 (m, 2H)<br>MS (ESI) [M + H]$^+$ = 247 |
| 48 | $^1$H NMR (300 MHz, MeOD) δ 8.48 (d, J = 9.1, 1H), 8.40 (d, J = 6.7, 1H), 7.94 (d, J = 8.4, 1H), 7.90 (d, J = 7.8, 1H), 7.54 (t, J = 8.0, 1H), 7.38 (d, J = 8.6, 1H), 7.30 (s, 2H), 2.58 (s, 3H)<br>MS (ESI) [M + H]$^+$ = 270 |
| 49 | $^1$H NMR (300 MHz, CDCl$_3$) δ 9.34 (s, 1H), 8.95 (s, 1H), 8.21 (d, J = 5.1, 1H), 7.87 (d, J = 8.9, 1H), 7.71 (d, J = 7.5, 1H), 7.52 (d, J = 7.9, 1H), 7.19 (t, J = 7.8, 1H), 7.05 (d, J = 8.9, 1H), 6.84 (d, J = 5.1, 1H), 2.76 (q, J = 7.6, 2H), 1.37 (t, J = 7.6, 3H) |
| 50 | $^1$H NMR (300 MHz, CDCl$_3$) δ 8.57 (d, J = 29.4, 1H), 7.80 (d, J = 8.8, 1H), 7.66 (t, J = 6.7, 2H), 7.46 (d, J = 7.9, 1H), 7.14 (t, J = 7.8, 1H), 7.06 (d, J = 8.8, 1H), 6.79 (d, J = 7.3, 1H), 2.73 (dd, J = 7.6, 15.2, 2H), 1.28 (t, J = 7.7, 3H) |
| 51 | $^1$H NMR (300 MHz, CDCl$_3$) δ 8.64 (s, 1H), 8.06 (s, 1H), 7.89 (d, J = 8.7, 1H), 7.71 (d, J = 7.4, 1H), 7.54 (t, J = 7.8, 1H), 7.20 (t, J = 7.7, 1H), 7.02 (d, J = 8.8, 1H), 6.67 (s, 1H), 2.43 (s, 3H), 2.39 (s, 3H)<br>$^{13}$C NMR (75 MHz, CDCl$_3$) δ 156.15, 153.17, 152.82, 150.16, 143.70, 137.92, 131.34, 129.89, 126.49, 125.47, 123.43, 118.62, 114.47, 111.02, 24.13, 21.70.<br>MS (ESI) [M + H]$^+$ = 284 |
| 52 | $^1$H NMR (300 MHz, CDCl$_3$) δ 8.89 (d, J = 8.8, 1H), 8.05 (d, J = 8.8, 1H), 8.01 (s, 1H), 7.93 (d, J = 8.8, 1H), 7.79 (d, J = 7.5, 1H), 7.64 (d, J = 8.0, 1H), 7.32 (t, J = 7.8, 1H), 7.13 (d, J = 8.8, 1H), 2.67 (s, 3H) |
| 53 | $^1$H NMR (300 MHz, CDCl$_3$) δ 9.27 (s, 1H), 8.33 (d, J = 5.7, 1H), 8.13 (d, J = 5.2, 1H), 8.00 (d, J = 8.8, 1H), 7.76 (d, J = 7.4, 1H), 7.60 (d, J = 8.0, 1H), 7.29 (d, J = 7.9, 1H), 7.07 (d, J = 8.9, 1H), 6.97 (d, J = 4.8, 1H) |
| 54 | MS (ESI) [M + H]$^+$ = 250 |
| 55 | $^1$H NMR (300 MHz, CDCl$_3$) δ 8.19 (s, 1H), 7.90 (d, J = 9.0, 1H), 7.63 (d, J = 7.5, 1H), 7.52 (d, J = 7.9, 1H), 7.33 (d, J = 7.4, 1H), 7.14 (t, J = 7.8, 1H), 6.69 (d, J = 7.5, 1H), 2.70 (dd, J = 7.3, 14.8, 2H), 2.47 (s, 3H), 1.26 (t, J = 7.7, 3H) |
| 56 | $^1$H NMR (300 MHz, CDCl$_3$) δ 8.20 (s, 1H), 7.90 (d, J = 9.0, 1H), 7.63 (d, J = 7.5, 1H), 7.52 (d, J = 7.9, 1H), 7.33 (d, J = 7.4, 1H), 7.14 (t, J = 7.8, 1H), 6.69 (d, J = 7.5, 1H), 2.70 (dd, J = 7.3, 14.8, 2H), 2.47 (s, 3H), 1.25 (dd, J = 7.5, 15.5, 3H) |
| 57 | MS (ESI) [M + H]$^+$ = 253 |
| 58 | MS (ESI) [M + H]$^+$ = 314-316 |
| 59 | $^1$H NMR (300 MHz, CDCl$_3$) δ 8.91 (d, J = 1.7, 1H), 8.46 (d, J = 8.8, 1H), 8.28 (dd, J = 2.0, 8.8, 1H), 8.23 (s, 1H), 8.03 (d, J = 8.8, 1H), 7.88 (d, J = 8.3, 1H), 7.70 (d, J = 8.0, 1H), 7.67-7.58 (m, 1H), 7.38 (t, J = 7.4, 1H), 7.32 (d, J = 8.8, 2H), 3.91 (s, 3H) |
| 60 | $^1$H NMR (300 MHz, CDCl$_3$) δ 8.94 (d, J = 8.9, 1H), 8.91 (d, J = 1.8, 1H), 8.37 (dd, J = 2.2, 8.8, 1H), 8.04 (d, J = 8.9, 2H), 7.77 (d, J = 7.5, 1H), 7.62 (d, J = 7.2, 1H), 7.30 (t, J = 7.8, 2H), 7.19 (d, J = 8.8, 2H), 3.92 (s, 3H) |
| 61 | $^1$H NMR (300 MHz, CDCl$_3$) δ 8.96 (d, J = 8.8, 1H), 8.85 (d, J = 1.3, 1H), 8.28 (d, J = 9.9, 1H), 7.84 (d, J = 8.0, 1H), 7.77 (s, 1H), 7.65 (s, 1H), 7.59 (d, J = 8.4, 2H), 7.53 (d, J = 8.4, 1H), 7.31 (t, J = 7.4, 1H), 3.88 (s, 4H), 2.42 (s, 4H)<br>MS (ESI) [M + H]$^+$ = 294 |
| 62 | $^1$H NMR (300 MHz, CDCl$_3$) δ 11.02 (s, 1H), 8.75 (d, J = 9.2, 1H), 8.44 (d, J = 3.7, 1H), 8.31 (d, J = 7.9, 1H), 8.10 (d, J = 9.0, 1H), 7.72 (d, J = 7.5, 1H), 7.64 (d, J = 8.2, 1H), 7.27 (d, J = 8.1, 1H), 6.88 (dd, J = 4.7, 7.8, 1H), 3.97 (s, 3H)<br>MS (ESI) [M + H]$^+$ = 314 |
| 63 | MS (ESI) [M + H]$^+$ = 266 |

TABLE II-continued

| Ex | Characterizations |
|---|---|
| 64 | ¹H NMR (300 MHz, DMSO) δ 10.38 (s, 1H), 8.56 (s, 1H), 8.28 (d, J = 9.1, 1H), 8.20-8.03 (m, 3H), 7.50 (d, J = 8.7, 1H), 7.45 (d, J = 8.0, 1H), 6.88 (d, J = 4.4, 1H), 2.37 (s, 3H) |
| 65 | MS (ESI) [M + H]⁺ = 314-316 |
| 66 | MS (ESI) [M + H]⁺ = 250 |
| 67 | ¹H NMR (300 MHz, DMSO) δ 10.51 (s, 1H), 8.83 (d, J = 2.3, 1H), 8.62 (d, J = 9.3, 1H), 8.24 (dd, J = 2.7, 9.1, 1H), 7.96 (d, J = 8.9, 1H), 7.81 (d, J = 7.8, 1H), 7.67 (t, J = 7.6, 1H), 7.45 (d, J = 11.2, 2H), 3.86 (s, 3H), 2.62 (s, 3H)<br>MS (ESI) [M + H]⁺ = 294 |
| 68 | ¹H NMR (300 MHz, CDCl₃) δ 9.57 (s, 1H), 8.44 (d, J = 4.8, 1H), 8.05 (d, J = 8.8, 1H), 7.86 (s, 1H), 7.80 (d, J = 7.5, 1H), 7.64 (d, J = 8.0, 1H), 7.31 (t, J = 7.8, 1H), 7.19 (d, J = 4.3, 1H), 7.04 (d, J = 8.8, 1H) |
| 69 | ¹H NMR (300 MHz, CDCl₃) δ 9.12 (s, 1H), 7.94 (d, J = 8.6, 1H), 7.71 (d, J = 7.5, 1H), 7.57 (d, J = 7.8, 1H), 7.40 (s, 1H), 7.25 (d, J = 10.2, 2H), 7.17 (s, 1H), 7.05 (s, 1H) |
| 70 | ¹H NMR (300 MHz, CDCl₃) δ 9.07 (d, J = 8.5, 1H), 7.97 (d, J = 8.8, 1H), 7.90 (t, J = 8.0, 1H), 7.84 (s, 1H), 7.75 (dd, J = 1.1, 7.5, 1H), 7.62-7.55 (m, 1H), 7.31 (d, J = 7.6, 1H), 7.27 (t, J = 7.8, 1H), 7.08 (d, J = 8.8, 1H)<br>MS (ESI) [M + H]⁺ = 274 |
| 71 | MS (ESI) [M + H]⁺ = 274 |
| 72 | ¹H NMR (300 MHz, CDCl₃) δ 8.67 (d, J = 7.9, 1H), 7.83 (d, J = 8.3, 1H), 7.71 (s, 1H), 7.69-7.61 (m, 1H), 7.57 (d, J = 7.9, 2H), 7.52 (d, J = 7.1, 1H), 7.28 (t, J = 7.4, 1H), 2.74 (q, J = 7.6, 2H), 2.42 (s, 3H), 1.31 (t, J = 7.6, 3H)<br>MS (ESI) [M + H]⁺ = 264 |
| 73 | ¹H NMR (300 MHz, CDCl₃) δ 8.91 (dd, J = 3.8, 9.0, 1H), 8.11 (d, J = 2.9, 1H), 7.81 (d, J = 8.3, 1H), 7.71 (s, 1H), 7.56 (dd, J = 7.4, 14.1, 2H), 7.51-7.42 (m, 1H), 7.29 (d, J = 7.2, 1H), 2.38 (s, 3H)<br>MS (ESI) [M + H]⁺ = 254 |
| 74 | ¹H NMR (300 MHz, CDCl₃) δ 8.96 (d, J = 8.3, 1H), 8.49 (s, 1H), 7.89 (dd, J = 1.9, 9.0, 1H), 7.82 (d, J = 8.2, 1H), 7.72 (s, 1H), 7.57 (t, J = 8.7, 3H), 7.33 (t, J = 7.4, 1H), 2.37 (s, 3H)<br>MS (ESI) [M + H]⁺ = 304 |
| 75 | ¹H NMR (300 MHz, CDCl₃) δ 7.83 (d, J = 9.0, 1H), 7.69 (dd, J = 1.3, 7.6, 1H), 7.53 (dd, J = 1.2, 8.0, 1H), 7.42 (d, J = 8.9, 2H), 7.15 (t, J = 7.8, 1H), 6.89 (d, J = 8.9, 2H), 6.79 (d, J = 8.9, 2H), 2.97 (s, 6H) |
| 77 | ¹H NMR (300 MHz, CDCl₃) δ 7.83 (d, J = 8.8, 1H), 7.70 (d, J = 7.6, 1H), 7.59 (d, J = 8.6, 2H), 7.52 (d, J = 7.3, 1H), 7.16 (t, J = 7.7, 1H), 6.94 (d, J = 8.4, 3H), 6.86 (d, J = 8.8, 1H), 3.82 (s, 3H)<br>¹³C NMR (75 MHz, CDCl₃) δ 156.40, 155.54, 144.29, 138.09, 132.96, 130.44, 129.99, 126.61, 125.22, 123.29, 122.66, 114.73, 112.16, 55.74.<br>MS (ESI) [M + H]⁺ = 285 |
| 78 | ¹H NMR (300 MHz, CDCl₃) δ 7.80 (t, J = 7.6, 2H), 7.64 (d, J = 8.9, 2H), 7.61-7.55 (m, 1H), 7.33 (t, J = 7.6, 1H), 7.19 (d, J = 8.7, 2H), 2.59 (s, 3H) |
| 79 | ¹H NMR (300 MHz, CDCl₃) δ 7.78 (d, J = 8.4, 1H), 7.76-7.71 (m, 2H), 7.69 (s, 1H), 7.57 (dd, J = 1.1, 8.0, 1H), 7.51 (ddd, J = 1.5, 7.0, 8.4, 1H), 7.29-7.21 (m, 1H), 6.96-6.90 (m, 2H), 3.82 (s, 3H), 2.35 (s, 3H) |
| 80 | ¹H NMR (300 MHz, CDCl₃) δ 7.92 (d, J = 8.9 Hz, 2H), 7.84 (d, J = 8.3 Hz, 1H), 7.78 (s, 1H), 7.62 (d, J = 8.0 Hz, 1H), 7.57 (t, J = 7.7 Hz, 1H), 7.32 (t, J = 7.4 Hz, 1H), 7.24 (d, J = 8.7 Hz, 2H), 6.53 (s, 1H), 2.42 (s, 3H)<br>¹³C NMR (75 MHz, CDCl₃) δ 152.46, 146.25, 143.86, 139.33, 136.83, 128.93, 126.96, 126.71, 124.75, 123.56, 121.88, 120.44, 119.95, 17.77.<br>MS (ESI) [M + H]⁺ = 319 |
| 81 | ¹H NMR (300 MHz, CDCl₃) δ 7.75 (d, J = 8.3, 1H), 7.66 (d, J = 8.5, 3H), 7.55 (d, J = 7.8, 1H), 7.48 (t, J = 7.6, 1H), 7.20 (d, J = 7.2, 1H), 6.80 (d, J = 8.8, 2H), 6.32 (s, 1H), 2.93 (s, 7H), 2.35 (s, 3H) |
| 82 | ¹H NMR (300 MHz, CDCl₃) δ 7.92 (d, J = 8.9, 1H), 7.82-7.70 (m, 2H), 7.66 (d, J = 7.8, 1H), 7.59 (t, J = 7.6, 1H), 7.30 (dd, J = 6.0, 13.5, 1H), 7.14 (s, 1H), 7.11 (s, 1H), 6.84 (d, J = 8.9, 1H), 2.32 (s, 3H)<br>MS (ESI) [M + H]⁺ = 319 |
| 83 | ¹H NMR (300 MHz, CDCl₃) δ 7.93-7.86 (m, 1H), 7.85 (s, 1H), 7.82 (d, J = 8.4, 1H), 7.59 (dd, J = 8.2, 15.5, 2H), 7.44-7.38 (m, 2H), 7.29 (dd, J = 8.3, 16.8, 2H), 6.91 (d, J = 9.0, 1H), 6.87 (d, J = 8.3, 1H)<br>MS (ESI) [M + H]⁺ = 305 |
| 84 | ¹H NMR (300 MHz, CDCl₃) δ 8.67 (d, J = 8.1, 1H), 7.92 (d, J = 8.9, 1H), 7.85 (d, J = 8.4, 1H), 7.63 (d, J = 7.6, 1H), 7.58 (d, J = 7.3, 1H), 7.30 (dd, J = 6.8, 14.8, 3H), 7.02 (t, J = 7.8, 1H), 6.89 (d, J = 8.9, 1H)<br>MS (ESI) [M + H]⁺ = 305 |
| 86 | ¹H NMR (300 MHz, CDCl₃) δ 7.93 (d, J = 8.9, 1H), 7.83 (d, J = 8.3, 1H), 7.70 (d, J = 12.0, 1H), 7.61 (dd, J = 7.9, 18.1, 2H), 7.32 (d, J = 7.9, 1H), 7.31-7.25 (m, 1H), 7.21 (t, J = 6.5, 1H), 6.92 (d, J = 8.9, 1H), 6.79-6.68 (m, 1H)<br>MS (ESI) [M + H]⁺ = 239 |
| 87 | ¹H NMR (300 MHz, CDCl₃) δ 8.27 (s, 1H), 7.76 (d, J = 8.9, 1H), 7.67 (d, J = 7.5, 1H), 7.51 (d, J = 8.2, 1H), 7.45 (d, J = 7.9, 1H), 7.28 (d, J = 8.2, 1H), 7.14 (t, J = 7.8, 1H), 6.86 (d, J = 10.1, 1H), 6.76 (d, J = 8.9, 1H)<br>MS (ESI) [M + H]⁺ = 339 |
| 88 | ¹H NMR (300 MHz, CDCl₃) δ 8.11 (dt, J = 2.1, 12.1, 1H), 7.76 (d, J = 8.9, 1H), 7.66 (dd, J = 1.2, 7.6, 1H), 7.45 (dd, J = 1.1, 8.0, 1H), 7.22 (dd, J = 1.4, 7.2, 2H), 7.18 (d, |

TABLE II-continued

| Ex | Characterizations |
|---|---|

J = 7.6, 1H), 7.12 (d, J = 7.8, 1H), 6.75 (d, J = 8.9, 1H), 6.69 (d, J = 7.9, 1H)
MS (ESI) [M + H]$^+$ = 273

89  $^1$H NMR (300 MHz, DMSO) δ 11.38 (s, 1H), 8.41 (d, J = 9.1, 1H), 7.93 (d, J = 7.8, 1H), 7.80 (dt, J = 8.1, 20.9, 4H), 7.50 (d, J = 7.8, 3H), 7.36 (d, J = 9.3, 1H)

90  $^1$H NMR (300 MHz, CDCl$_3$) δ 7.84 (d, J = 9.1, 2H), 7.79 (d, J = 8.9, 1H), 7.67 (dd, J = 1.2, 7.6, 1H), 7.48 (dd, J = 1.1, 8.0, 1H), 7.18 (s, 3H), 6.89 (s, 1H), 6.75 (d, J = 8.9, 1H)
$^{13}$C NMR (75 MHz, CDCl$_3$) δ 153.88, 144.30, 143.91, 139.00, 138.25, 131.13, 130.13, 126.55, 125.42, 123.45, 122.50, 122.17, 120.49, 119.10, 113.24.
MS (ESI) [M + H]$^+$ = 339

91  $^1$H NMR (300 MHz, CDCl$_3$) δ 8.74 (s, 1H), 8.54 (s, 1H), 8.46 (d, J = 8.8, 1H), 7.91 (dd, J = 5.5, 14.5, 2H), 7.79 (d, J = 8.9, 1H), 7.67 (d, J = 2.1, 1H), 7.56 (dd, J = 2.3, 8.9, 1H), 7.35 (d, J = 8.9, 1H)

92  $^1$H NMR (300 MHz, CDCl$_3$) δ 8.67 (d, J = 7.9, 1H), 7.83 (d, J = 8.3, 1H), 7.71 (s, 1H), 7.69-7.61 (m, 1H), 7.55 (dd, J = 7.5, 14.4, 2H), 7.29 (d, J = 7.8, 1H), 6.80 (d, J = 7.4, 1H)

93  $^1$H NMR (300 MHz, CDCl$_3$) δ 9.21 (dd, J = 1.5, 8.4, 1H), 7.85 (d, J = 8.4, 1H), 7.73 (s, 1H), 7.58 (d, J = 7.8, 1H), 7.53 (dd, J = 1.3, 8.3, 1H), 7.40-7.35 (m, 1H), 7.32 (dd, J = 1.1, 4.6, 1H), 7.31-7.24 (m, 2H), 7.04 (s, 1H), 7.02-6.94 (m, 1H), 2.38 (s, 3H)

94  $^1$H NMR (300 MHz, CDCl$_3$) δ 8.16 (d, J = 8.7, 1H), 7.83 (d, J = 8.9, 1H), 7.63 (d, J = 7.6, 1H), 7.48 (d, J = 8.0, 1H), 7.13 (t, J = 7.8, 1H), 7.08 (s, 1H), 7.04 (s, 2H), 6.81 (d, J = 8.9, 2H), 2.27 (s, 3H)
MS (ESI) [M + H]$^+$ = 353

95  $^1$H NMR (300 MHz, MeOD) δ 8.42 (s, 1H), 7.94 (d, J = 7.9, 1H), 7.83 (d, J = 8.1, 1H), 7.78 (d, J = 7.1, 1H), 7.72 (d, J = 8.7, 2H), 7.58 (d, J = 8.2, 3H), 2.60 (s, 3H)
MS (ESI) [M + H]$^+$ = 319

96  $^1$H NMR (300 MHz, CDCl$_3$) δ 7.79 (d, J = 8.9, 1H), 7.70 (d, J = 8.9, 1H), 7.64 (d, J = 8.9, 2H), 7.59 (d, J = 2.1, 1H), 7.50 (dd, J = 2.3, 8.9, 1H), 7.19 (d, J = 8.6, 2H), 6.85 (d, J = 8.9, 1H)
MS (ESI) [M + H]$^+$ = 281

97  $^1$H NMR (300 MHz, MeOD) δ 8.11 (d, J = 8.4, 1H), 7.81 (s, 2H), 7.62 (s, J = 8.7, 3H), 7.51 (d, J = 8.3, 2H), 7.12 (s, 1H), 2.77 (s, 3H)
MS (ESI) [M + H]$^+$ = 319

98  MS (ESI) [M + H]$^+$ = 383-385

99  MS (ESI) [M + H]$^+$ = 320

100  MS (ESI) [M + H]$^+$ = 316

101  $^1$H NMR (300 MHz, CDCl$_3$) δ 7.82 (d, J = 8.9, 1H), 7.70-7.63 (m, 1H), 7.51 (dd, J = 5.3, 7.6, 3H), 7.14 (t, J = 7.8, 1H), 6.91 (d, J = 8.8, 3H), 6.85 (d, J = 9.0, 2H), 3.96 (t, J = 6.5, 2H), 1.84-1.68 (m, 3H), 1.49 (dd, J = 7.4, 15.0, 3H), 0.97 (t, J = 7.4, 3H)
MS (ESI) [M + H]$^+$ = 327

102  $^1$H NMR (300 MHz, CDCl$_3$) δ 7.89 (d, J = 8.9, 1H), 7.76 (d, J = 8.5, 1H), 7.63 (d, J = 8.1, 1H), 7.59 (s, 1H), 7.54 (d, J = 8.8, 2H), 7.38-7.24 (m, 3H), 7.09 (d, J = 7.4, 1H), 7.02 (dd, J = 2.4, 8.8, 4H), 6.90 (d, J = 8.9, 1H)
MS (ESI) [M + H]$^+$ = 313

103  MS (ESI) [M + H]$^+$ = 334

104  $^1$H NMR (300 MHz, CDCl$_3$) δ 8.49 (d, J = 2.5, 1H), 7.89 (d, J = 8.8, 1H), 7.72 (d, J = 7.6, 1H), 7.63 (dd, J = 2.5, 8.9, 1H), 7.53 (d, J = 8.0, 1H), 7.23 (dd, J = 6.2, 14.0, 2H), 7.04 (s, 1H), 6.81 (d, J = 8.8, 1H)
MS (ESI) [M + H]$^+$ = 373

105  $^1$H NMR (300 MHz, CDCl$_3$) δ 8.85 (d, J = 2.6, 1H), 8.45 (d, J = 2.3, 1H), 8.01 (d, J = 8.1, 1H), 7.71 (d, J = 7.8, 1H), 7.58 (s, 1H), 7.53 (d, J = 7.6, 1H), 7.51-7.45 (m, 2H), 7.45-7.36 (m, 1H), 6.72-6.62 (m, 2H), 2.48 (s, 3H)
13C NMR (75 MHz, CDCl$_3$) δ 157.18, 154.80, 145.42, 143.80, 138.17, 135.04, 128.88, 128.76, 127.17, 127.04, 120.69, 115.22, 106.73, 24.38

106  $^1$H NMR (300 MHz, DMSO) δ 10.24 (s, 1H), 9.06 (d, J = 2.3, 1H), 8.65 (d, J = 1.8, 1H), 8.60 (d, J = 8.3, 1H), 8.56 (d, J = 4.5, 1H), 7.97 (dd, J = 8.2, 14.4, 2H), 7.69 (t, J = 6.9, 1H), 7.59 (t, J = 7.4, 1H), 7.08 (dd, J = 4.6, 8.3, 1H)
MS (ESI) [M + H]$^+$ = 267

107  $^1$H NMR (300 MHz, CDCl$_3$) δ 8.77 (dd, J = 1.5, 4.3, 1H), 8.06 (dd, J = 10.8, 18.4, 3H), 7.93 (d, J = 2.4, 1H), 7.57 (dd, J = 2.4, 9.0, 1H), 7.39 (ddd, J = 3.1, 8.3, 12.5, 3H), 6.93 (d, J = 8.4, 1H), 6.89 (s, 1H), 2.29 (s, 3H)

108  $^1$H NMR (300 MHz, CDCl$_3$) δ 8.72 (dd, J = 1.6, 4.2, 1H), 8.61 (d, J = 2.4, 1H), 8.11 (d, J = 8.3, 1H), 8.00 (d, J = 9.0, 1H), 7.91 (dd, J = 1.2, 5.0, 1H), 7.69 (dd, J = 2.4, 9.1, 1H), 7.35-7.26 (m, 2H), 7.01 (dd, J = 1.2, 7.9, 1H), 6.77 (dd, J = 5.1, 7.8, 1H), 3.93 (s, 3H)

109  $^1$H NMR (300 MHz, CDCl$_3$) δ 9.68 (s, 1H), 8.21 (s, 2H), 7.94 (d, J = 8.9, 1H), 7.79 (d, J = 9.2, 1H), 7.67 (d, J = 2.3, 1H), 7.56 (dd, J = 2.3, 8.9, 1H), 7.34 (d, J = 8.9, 1H)
MS (ESI) [M + H]$^+$ = 257

110  1H NMR (300 MHz, CDCl$_3$) δ 10.32 (s, 1H), 8.33-8.21 (m, 2H), 8.05 (d, J = 8.9, 1H), 8.00 (dd, J = 1.2, 7.6, 1H), 7.69 (dd, J = 1.1, 7.8, 1H), 7.61 (s, 1H), 7.30-7.22 (m, 3H), 7.16 (d, J = 8.8, 1H).
MS (ESI) [M + H]$^+$ = 301-303

111  $^1$H NMR (300 MHz, CDCl$_3$) δ 7.82 (d, J = 8.9, 1H), 7.70-7.63 (m, 1H), 7.51 (dd, J = 5.3, 7.6, 3H), 7.14 (t, J = 7.8, 1H), 6.91 (d, J = 8.8, 3H), 6.85 (d, J = 9.0, 2H), 3.96 (t, J = 6.5, 2H), 1.84-1.68 (m, 3H), 1.49 (dd, J = 7.4, 15.0, 3H), 0.97 (t, J = 7.4, 3H)

112  $^1$H NMR (300 MHz, CDCl$_3$) δ 7.89 (d, J = 8.9, 1H), 7.76 (d, J = 8.5, 1H), 7.63 (d, J = 8.1, 1H), 7.59 (s, 1H), 7.54 (d, J = 8.8, 2H), 7.38-7.24 (m, 3H), 7.09 (d, J = 7.4,

TABLE II-continued

| Ex | Characterizations |
|---|---|
| | 1H), 7.02 (dd, J = 2.4, 8.8, 4H), 6.90 (d, J = 8.9, 1H)<br>$^{13}$C NMR (75 MHz, DMSO) δ 152.94, 150.19, 142.48, 142.18, 138.20, 137.55, 135.74, 129.71, 126.99, 125.35, 123.84, 114.75.<br>MS (ESI) [M + H]$^+$ = 255 |
| 113 | $^1$H NMR (300 MHz, CDCl$_3$) δ 9.74 (s, 1H), 8.20 (s, 2H), 8.03 (d, J = 8.6, 1H), 7.87 (d, J = 7.6, 1H), 7.80 (s, 1H), 7.70 (d, J = 8.0, 1H), 7.63 (t, J = 7.7, 1H), 7.37 (t, J = 7.4, 1H), 7.30 (d, J = 8.7, 1H) |
| 114 | $^1$H NMR (300 MHz, CDCl$_3$) δ 9.67 (s, 1H), 8.34-8.12 (m, 2H), 7.84 (d, J = 8.0, 2H), 7.70-7.54 (m, 1H), 7.38 (t, J = 7.6, 1H), 7.17 (s, 1H), 2.61 (s, 3H)<br>MS (ESI) [M + H]$^+$ = 237 |
| 115 | $^1$H NMR (300 MHz, CDCl$_3$) δ 10.15 (s, 1H), 8.24-8.12 (m, 2H), 7.79 (s, 1H), 7.71 (s, 1H), 7.55 (t, J = 8.3, 2H), 7.30 (t, J = 7.9, 1H), 2.38 (s, 3H)<br>MS (ESI) [M + H]$^+$ = 237 |
| 116 | MS (ESI) [M + H]$^+$ = 240 |
| 117 | MS (ESI) [M + H]$^+$ = 253 |
| 118 | MS (ESI) [M + H]$^+$ = 222 |
| 119 | MS (ESI) [M + H]$^+$ = 256 |
| 121 | MS (ESI) [M + H]$^+$ = 222 |
| 124 | $^1$H NMR (300 MHz, CDCl$_3$) δ 8.42 (s, 1H), 7.95 (dd, J = 1.3, 8.2, 1H), 7.87-7.78 (m, 3H), 7.70-7.61 (m, 1H), 7.55-7.47 (m, 1H), 7.26 (dd, J = 2.4, 6.5, 3H), 6.90 (s, 1H)<br>MS (ESI) [M + H]$^+$ = 306 |
| 125 | $^1$H NMR (300 MHz, CDCl$_3$) δ 8.42 (s, 1H), 8.03 (d, J = 9.5, 1H), 7.92 (d, J = 8.2, 1H), 7.73 (d, J = 8.2, 1H), 7.61 (t, J = 7.3, 1H), 7.46 (t, J = 7.2, 1H), 7.13 (s, 2H), 6.84 (s, 1H), 2.35 (s, 3H) |
| 126 | $^1$H NMR (300 MHz, CDCl$_3$) δ 8.40 (s, 1H), 8.03 (s, 1H), 7.94 (d, J = 8.2, 1H), 7.84 (d, J = 8.2, 1H), 7.65 (t, J = 7.4, 1H), 7.53 (d, J = 7.1, 1H), 7.48 (d, J = 7.2, 1H), 7.35 (t, J = 8.2, 1H), 7.22 (s, 1H), 6.94 (d, J = 8.1, 1H) |
| 127 | $^1$H NMR (300 MHz, CDCl$_3$) δ 8.85 (dd, J = 1.0, 8.3, 1H), 8.47 (s, 1H), 7.96 (d, J = 8.2, 1H), 7.85 (d, J = 8.3, 1H), 7.72-7.61 (m, 1H), 7.57-7.47 (m, 1H), 7.42-7.36 (m, 1H), 7.33 (d, J = 10.0, 1H), 7.14 (s, 1H), 7.13-7.04 (m, 1H) |
| 128 | $^1$H NMR (300 MHz, CDCl$_3$) δ 9.17 (s, 1H), 8.68 (d, J = 9.1, 1H), 8.64 (d, J = 4.8, 2H), 8.15 (d, J = 9.1, 1H), 7.87 (d, J = 8.4, 1H), 7.76 (d, J = 8.1, 1H), 7.64 (t, J = 7.7, 1H), 7.39 (t, J = 7.5, 1H), 6.87 (t, J = 4.8, 1H)<br>$^{13}$C NMR (75 MHz, CDCl3) δ 158.34, 138.07, 129.85, 127.63, 127.31, 124.34, 114.20, 113.90. |
| 129 | $^1$H NMR (300 MHz, CDCl$_3$) δ 9.14 (s, 1H), 8.73 (d, J = 21.2, 3H), 8.17 (s, 1H), 7.73 (d, J = 20.3, 2H), 7.28 (d, J = 9.6, 2H), 6.91 (s, 1H) |
| 130 | $^1$H NMR (300 MHz, CDCl$_3$) δ 9.05 (s, 1H), 8.64 (d, J = 4.8, 2H), 8.52 (s, 1H), 7.89 (dd, J = 8.5, 14.6, 2H), 7.63 (t, J = 7.5, 1H), 7.41 (t, J = 7.4, 1H), 6.86 (t, J = 4.8, 1H), 2.74 (s, 3H)<br>MS (ESI) [M + H]$^+$ = 237 |
| 132 | $^1$H NMR (300 MHz, CDCl$_3$) δ 8.86 (d, J = 2.6, 1H), 8.70 (d, J = 2.5, 1H), 8.32 (d, J = 1.1, 1H), 8.25-8.21 (m, 1H), 8.10 (d, J = 2.7, 1H), 8.06 (d, J = 8.3, 1H), 7.82 (dd, J = 1.2, 7.9, 1H), 7.66-7.51 (m, 3H), 6.89 (s, 1H) |
| 135 | $^1$H NMR (300 MHz, CDCl$_3$) δ 9.09 (s, 1H), 8.71 (s, 1H), 8.54 (d, J = 8.4, 1H), 8.37 (dd, J = 1.0, 4.9, 1H), 7.96 (d, J = 8.2, 1H), 7.85 (d, J = 8.3, 1H), 7.82-7.74 (m, 1H), 7.66 (t, J = 7.6, 1H), 7.52 (dd, J = 7.0, 8.1, 1H), 7.02 (dd, J = 5.0, 7.2, 1H)<br>MS (ESI) [M + H]$^+$ = 223 |
| 136 | $^1$H NMR (300 MHz, CDCl$_3$) δ 9.02 (s, 1H), 8.70 (s, 1H), 8.30 (s, 1H), 8.20 (d, J = 5.1, 1H), 7.94 (d, J = 8.1, 1H), 7.84 (d, J = 8.2, 1H), 7.64 (t, J = 7.6, 1H), 7.49 (t, J = 8.1, 1H), 6.83 (d, J = 5.0, 1H), 2.43 (s, 3H)<br>$^{13}$C NMR (75 MHz, CDCl$_3$) δ 153.28, 150.20, 148.55, 147.40, 140.93, 139.83, 138.35, 130.44, 129.16, 127.18, 126.28, 119.70, 113.75, 21.87.<br>MS (ESI) [M + H]$^+$ = 237 |
| 137 | $^1$H NMR (300 MHz, DMSO) δ 11.10 (s, 1H), 9.03 (s, 1H), 8.82-8.75 (m, 1H), 8.56 (d, J = 8.9, 1H), 8.24 (dd, J = 2.3, 8.9, 1H), 7.96 (dd, J = 1.2, 8.2, 1H), 7.87 (dd, J = 1.0, 8.3, 1H), 7.79-7.71 (m, 1H), 7.61 (ddd, J = 1.4, 7.0, 8.3, 1H)<br>MS (ESI) [M + H]$^+$ = 248 |
| 138 | $^1$H NMR (300 MHz, CDCl$_3$) δ 8.72 (s, 1H), 8.53 (s, 1H), 8.20 (d, J = 8.3, 1H), 7.93 (d, J = 8.2, 1H), 7.81 (d, J = 8.3, 1H), 7.62 (td, J = 3.4, 8.1, 2H), 7.53-7.43 (m, 1H), 6.83 (d, J = 7.4, 1H), 2.48 (s, 3H)<br>$^{13}$C NMR (75 MHz, CDCl$_3$) δ 156.86, 152.27, 148.40, 140.92, 139.70, 139.00, 138.35, 130.42, 129.13, 127.14, 126.27, 117.76, 110.01, 24.15.<br>MS (ESI) [M + H]$^+$ = 237 |
| 139 | $^1$H NMR (300 MHz, CDCl$_3$) δ 8.53 (s, 1H), 8.20 (d, J = 4.8, 1H), 8.04 (d, J = 8.3, 1H), 7.92 (d, J = 8.4, 1H), 7.87 (s, 1H), 7.79 (t, J = 7.6, 1H), 7.60 (t, J = 7.6, 1H), 6.88 (d, J = 4.7, 1H), 2.46 (s, 3H) |
| 140 | $^1$H NMR (300 MHz, CDCl$_3$) δ 9.93 (s, 1H), 8.19 (s, 1H), 8.05 (d, J = 8.1, 1H), 7.99 (s, 1H), 7.82 (d, J = 8.2, 1H), 7.69 (t, J = 7.6, 1H), 7.59 (t, J = 8.2, 1H), 2.53 (s, 4H) |
| 141 | $^1$H NMR (300 MHz, CDCl$_3$) δ 9.72 (s, 1H), 9.35 (s, 1H), 8.30 (d, J = 5.0, 1H), 8.05 (d, J = 7.7, 1H), 7.87 (d, J = 7.0, 1H), 7.66 (dd, J = 7.4, 16.9, 3H), 6.92 (d, J = 4.9, 1H), 2.58 (s, 3H) |
| 143 | $^1$H NMR (300 MHz, DMSO) δ 8.85 (s, 1H), 8.42 (d, J = 5.3, 1H), 7.96 (d, J = 9.1, 1H), 7.44 (s, 1H), 7.30 (d, J = 5.4, 4H), 7.28-7.21 (m, 2H), 6.66 (d, J = 5.3, 1H), 2.99 (s, 6H) |

TABLE II-continued

| Ex | Characterizations |
|---|---|
| | ¹³C NMR (75 MHz, DMSO) δ 156.82, 150.25, 149.69, 143.79, 141.71, 125.95, 122.33, 118.88, 117.37, 115.95, 109.39, 104.92, 43.57 |
| | MS (ESI) [M + H]+ = 348 |
| 144 | MS (ESI) [M + H]⁺ = 390 |
| 145 | MS (ESI) [M + H]⁺ = 252 |
| 146 | ¹H NMR (300 MHz, DMSO) δ 9.34 (s, 1H), 8.59 (d, J = 5.2, 1H), 8.53 (s, 1H), 8.13 (d, J = 5.1, 1H), 7.98 (d, J = 9.0, 1H), 7.66 (d, J = 9.1, 1H), 6.80 (d, J = 5.2, 1H), 6.76 (s, 1H), 6.69 (d, J = 4.9, 1H), 4.00 (s, 3H), 2.26 (s, 3H). |
| | ¹³C NMR (75 MHz, DMSO) δ 161.31, 155.67, 151.63, 150.25, 147.77, 147.01, 142.97, 121.56, 119.16, 116.61, 114.75, 112.60, 111.41, 98.91, 55.78, 20.66. |
| | MS (ESI) [M + H]⁺ = 266 |
| 147 | MS (ESI) [M + H]⁺ = 279 |
| 149 | MS (ESI) [M + H]⁺ = 318 |
| 150 | MS (ESI) [M + H]⁺ = 280 |
| 151 | ¹H NMR (300 MHz, CDCl₃) δ 8.35 (s, 1H), 8.04 (d, J = 8.3, 1H), 7.82 (d, J = 8.9, 1H), 7.74 (d, J = 8.9, 1H), 7.60 (t, J = 7.8, 2H), 7.50 (dd, J = 2.3, 8.9, 1H), 7.36 (d, J = 8.9, 1H), 6.79 (d, J = 7.4, 1H), 2.75 (q, J = 7.6, 2H), 1.30 (t, J = 7.6, 3H). |
| | MS (ESI) [M + H]⁺ = 284 |
| 152 | ¹H NMR (300 MHz, CDCl₃) δ 8.30 (d, J = 8.5, 1H), 8.08 (s, 1H), 7.90 (d, J = 9.0, 1H), 7.77 (d, J = 8.9, 1H), 7.65 (d, J = 2.2, 1H), 7.55 (td, J = 2.0, 8.8, 2H), 7.39 (d, J = 9.0, 1H), 2.31 (s, 3H). |
| | MS (ESI) [M + H]⁺ = 270 |
| 153 | ¹H NMR (300 MHz, CDCl₃) δ 8.75 (s, 1H), 8.54 (s, 1H), 8.46 (d, J = 8.8, 1H), 7.91 (dd, J = 5.5, 14.5, 2H), 7.79 (d, J = 8.9, 1H), 7.67 (d, J = 2.1, 1H), 7.56 (dd, J = 2.3, 8.9, 1H), 7.35 (d, J = 8.9, 1H). |
| | MS (ESI) [M + H]⁺ = 324 |
| 154 | ¹H NMR (300 MHz, DMSO) δ 9.08 (s, 1H), 8.12 (d, J = 8.4, 1H), 7.73 (d, J = 8.2, 2H), 7.66 (d, J = 10.0, 1H), 7.53 (s, 1H), 7.25 (s, 1H), 6.82 (s, 1H), 5.10 (s, 2H), 2.16 (s, 4H). |
| | MS (ESI) [M + H]⁺ = 285 |
| 155 | ¹H NMR (300 MHz, CDCl₃) δ 7.68 (d, J = 8.3, 1H), 7.61 (s, 1H), 7.56 (d, J = 11.5, 2H), 7.44 (d, J = 8.3, 1H), 7.38 (d, J = 7.8, 1H), 7.13 (t, J = 7.4, 1H), 6.80 (d, J = 8.7, 2H), 3.85 (t, J = 6.5, 2H), 2.18 (s, 3H). 1.73-1.58 (m, 2H), 1.48-1.31 (m, 2H), 0.88 (t, J = 7.3, 3H) |
| | MS (ESI) [M + H]⁺ = 307 |
| 156 | ¹H NMR (300 MHz, CDCl₃) δ 7.75 (d, J = 9.1, 1H), 7.62 (d, J = 8.9, 1H), 7.58 (d, J = 2.2, 1H), 7.48 (dd, J = 2.4, 8.9, 1H), 7.30 (d, J = 8.9, 2H), 6.86 (d, J = 9.0, 1H), 6.77 (d, J = 8.9, 2H), 6.71 (s, 1H), 2.97 (s, 6H) |
| | MS (ESI) [M + H]⁺ = 298 |
| 157 | ¹H NMR (300 MHz, CDCl₃) δ 7.98 (d, J = 2.6, 1H), 7.89 (d, J = 8.9, 1H), 7.72 (d, J = 7.5, 1H), 7.62 (dd, J = 2.6, 8.8, 1H), 7.55 (d, J = 7.8, 1H), 7.20 (t, J = 7.8, 1H), 6.95 (d, J = 8.9, 1H), 6.84 (d, J = 8.9, 1H), 6.79 (s, 1H), 3.91 (s, 3H) |
| | MS (ESI) [M + H]⁺ = 319 |
| 158 | ¹H NMR (300 MHz, CDCl₃) δ 7.89 (d, J = 9.0, 1H), 7.70 (dd, J = 1.2, 7.5, 1H), 7.56 (dd, J = 1.1, 8.0, 1H), 7.30 (d, J = 8.6, 1H), 7.20 (t, J = 7.8, 1H), 6.71 (t, J = 5.9, 2H), 6.64 (d, J = 9.5, 1H). |
| | MS (ESI) [M + H]⁺ = 354 |
| 159 | ¹H NMR (300 MHz, CDCl₃) δ 8.80 (d, J = 2.6, 1H), 8.37 (d, J = 2.6, 1H), 8.01 (d, J = 8.1, 1H), 7.91 (dd, J = 1.6, 4.9, 1H), 7.78-7.70 (m, 1H), 7.58-7.43 (m, 2H), 7.09 (dd, J = 1.6, 7.6, 1H), 6.84 (dd, J = 4.9, 7.6, 1H), 6.69 (s, 1H), 3.82-3.07 (m, 2H). |
| 160 | ¹H NMR (300 MHz, CDCl₃) δ 9.68-8.90 (m, 1H), 8.77 (s, 1H), 8.35 (s, 1H), 8.14 (d, J = 5.0, 1H), 7.96 (s, 1H), 7.79 (d, J = 8.8, 1H), 7.61 (d, J = 8.5, 1H), 6.88 (d, J = 4.8, 1H), 2.46 (s, 3H) |
| 161 | ¹H NMR (300 MHz, CDCl₃) δ 9.98 (s, 1H), 8.70 (s, 1H), 8.45 (s, 1H), 8.27 (d, J = 5.2, 1H), 7.94 (d, J = 8.1, 1H), 7.84 (d, J = 8.2, 1H), 7.63 (t, J = 7.5, 1H), 7.48 (t, J = 7.5, 1H), 6.87 (d, J = 5.0, 1H), 2.74 (q, J = 7.6, 2H), 1.34 (t, J = 7.6, 3H). |
| | MS (ESI) [M + H]⁺ = 251 |
| 162 | ¹H NMR (300 MHz, CDCl₃) δ 8.73 (s, 1H), 8.70-8.60 (m, 1H), 8.48 (s, 1H), 8.31 (s, 1H), 7.98 (d, J = 8.1, 1H), 7.86 (d, J = 7.9, 1H), 7.68 (t, J = 8.2, 1H), 7.54 (t, J = 8.1, 1H), 2.49 (s, 3H) |
| | MS (ESI) [M + H]⁺ = 315 |
| 163 | ¹H NMR (300 MHz, CDCl₃) δ 8.75 (s, 1H), 8.68 (s, 1H), 8.01 (s, 1H), 7.95 (d, J = 8.2, 1H), 7.84 (d, J = 8.3, 1H), 7.64 (t, J = 8.2, 1H), 7.49 (t, J = 7.0, 1H), 6.69 (s, 1H), 2.45 (s, 3H), 2.38 (s, 3H) |
| | MS (ESI) [M + H]⁺ = 251 |
| 164 | ¹H NMR (300 MHz, DMSO) δ 10.46 (s, 1H), 9.00 (s, 1H), 8.41 (s, 1H), 8.24 (d, J = 3.0, 1H), 7.90 (d, J = 8.2, 1H), 7.79 (d, J = 8.3, 1H), 7.69 (t, J = 7.0, 1H), 7.52 (t, J = 7.4, 1H), 6.98 (d, J = 4.8, 1H), 5.45 (q, J = 5.6, 1H), 4.58 (d, J = 5.7, 2H). |
| | MS (ESI) [M + H]⁺ = 253 |
| 165 | ¹H NMR (300 MHz, CDCl₃) δ 9.07 (s, 1H), 8.79 (s, 1H), 8.51 (s, 1H), 8.18 (s, 1H), 8.09-8.01 (m, 1H), 7.94 (d, J = 8.4, 1H), 7.81-7.71 (m, 1H), 7.69-7.59 (m, 1H), 2.80 (s, 3H) |
| | MS (ESI) [M + H]⁺ = 282 |
| 166 | ¹H NMR (300 MHz, CDCl₃) δ 8.49 (d, J = 5.0, 1H), 7.77 (d, J = 9.0, 1H), 7.32 (d, J = 2.0, 1H), 7.12 (d, J = 9.0, 2H), 6.99 (dd, J = 2.0, J = 9.0, 1H), 6.82 (d, J = 9.0, 2H), |

TABLE II-continued

| Ex | Characterizations |
|---|---|
|  | 6.57 (d, J = 5.0, 1H), 5.78 (s, 1H), 3.74 (s, 3H), 3.17 (s, 4H), 2.62 (s, 4H), 2.34 (s, 3H) |
| 167 | MS (ESI) [M + H]$^+$ = 335 |
| 168 | MS (ESI) [M + H]$^+$ = 321 |

The following examples are provided as illustrations and in no way limit the scope of this invention.

The following examples illustrate in detail the preparation of some compounds according to the invention. The structures of the products obtained have been confirmed by NMR spectra.

EXAMPLES

According to route (A), the compound of formula (III) is placed in a protic solvent such as tert-butanol. The compound of formula (IV) is then added in a 1.1 molar ratio with respect to the compound of formula (III) in presence of Cs$_2$CO$_3$, in a 2.8 molar ratio, in the presence of Xantphos (4,5-Bis(diphenylphosphino)-9,9-dimethylxanthene), in a 2 mol % amount relative to the total amount of compound of formula (III), and in the presence of Pd(OAc)$_2$, in a 2 mol % amount relative to the total amount of compound of formula (III). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compounds (6), (43), (77), (80), (90), (112) and (136).

According to route (B), the compound of formula (V) is placed in a protic solvent such as tert-butanol. The compound of formula (VI) is then added in a 1.1 molar ratio with respect to the compound of formula (V) in presence of Cs$_2$CO$_3$ in a 2.8 molar ratio, in the presence of Xantphos (4,5-Bis(diphenylphosphino)-9,9-dimethylxanthene) in a 2 mol % amount relative to the total amount of compound of formula (V), and in the presence of a Pd(OAc)$_2$, in a 2 mol % amount relative to the total amount of compound of formula (V). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compound (106).

Example 1

Compound (6) of the Table I

According to route (A), a mixture of 2,8-dichloroquinoline (1.5 g) and 2-amino-4methylpyridine (904 mg), Pd(OAc)$_2$ (34 mg), XantPhos (88 mg) and Cs$_2$CO$_3$ (7.0 g) in 30 mL of t-BuOH gave compound (6) (1.3 g).

$^1$H NMR (300 MHz, DMSO) δ 10.23 (s, 1H), 8.96 (s, 1H), 8.18 (d, J=8.8, 2H), 7.78 (dd, J=7.7, 13.7, 2H), 7.46 (d, J=8.9, 1H), 7.31 (t, J=7.8, 1H), 6.86 (d, J=4.3, 1H), 2.37 (s, 3H).

$^{13}$C NMR (75 MHz, DMSO) δ 153.63, 153.61, 148.37, 147.32, 142.65, 137.52, 129.68, 129.47, 126.82, 125.06, 123.26, 118.36, 115.10, 113.31, 21.24.

MS (ESI) [M+H]$^+$=270

Example 2

Compound (43) of the Table I

According to route (A), a mixture of 2,8-dichloroquinoline (394 mg) and 2-amino-5fluoropyridine (246 mg), Pd(OAc)$_2$ (9 mg), XantPhos (23 mg) and Cs$_2$CO$_3$ (1.8 g) in 8 mL of t-BuOH gave compound (43) (320 mg).

$^1$H NMR (300 MHz, DMSO) δ 10.41 (s, 1H), 9.08 (dd, J=4.1, 9.3, 1H), 8.31 (d, J=2.9, 1H), 8.20 (d, J=8.9, 1H), 7.88-7.70 (m, 3H), 7.44 (d, J=8.9, 1H), 7.32 (t, J=7.8, 1H).

$^{13}$C NMR (75 MHz, DMSO) δ 156.30, 153.32, 153.04, 150.17, 142.55, 137.73, 135.06, 134.74, 129.58, 129.49, 126.86, 125.29, 125.14, 125.04, 123.36, 114.91, 113.36.

MS (ESI) [M+H]$^+$=274

Example 3

Compound (77) of the Table I

According to route (A), a mixture of 2,8-dichloroquinoline (985 mg) and p-anisidine (677 mg), Pd(OAc)$_2$ (22 mg), XantPhos (58 mg) and Cs$_2$CO$_3$ (4.6 g) in 20 mL of t-BuOH gave compound (77) (629 mg).

$^1$H NMR (300 MHz, CDCl$_3$) δ 7.83 (d, J=8.8, 1H), 7.70 (d, J=7.6, 1H), 7.59 (d, J=8.6, 2H), 7.52 (d, J=7.3, 1H), 7.16 (t, J=7.7, 1H), 6.94 (d, J=8.4, 3H), 6.86 (d, J=8.8, 1H), 3.82 (s, 3H).

$^{13}$C NMR (75 MHz, CDCl$_3$) δ 156.40, 155.54, 144.29, 138.09, 132.96, 130.44, 129.99, 126.61, 125.22, 123.29, 122.66, 114.73, 112.16, 55.74.

MS (ESI) [M+H]$^+$=285

Example 4

Compound (80) of the Table I

According to route (A), a mixture of 2-chloro-3-methylquinoline (885 mg) and 4-(trifluoromethoxy)aniline (743 µL), Pd(OAc)$_2$ (22 mg), XantPhos (58 mg) and Cs$_2$CO$_3$ (4.6 g) in 20 mL of t-BuOH gave compound (80) (1.3 g).

$^1$H NMR (300 MHz, CDCl$_3$) δ 7.92 (d, J=8.9 Hz, 2H), 7.84 (d, J=8.3 Hz, 1H), 7.78 (s, 1H), 7.62 (d, J=8.0 Hz, 1H), 7.57 (t, J=7.7 Hz, 1H), 7.32 (t, J=7.4 Hz, 1H), 7.24 (d, J=8.7 Hz, 2H), 6.53 (s, 1H), 2.42 (s, 3H).

$^{13}$C NMR (75 MHz, CDCl$_3$) δ 152.46, 146.25, 143.86, 139.33, 136.83, 128.93, 126.96, 126.71, 124.75, 123.56, 121.88, 120.44, 119.95, 17.77.

MS (ESI) [M+H]$^+$=319

Example 5

Compound (90) of the Table I

According to route (A), a mixture of 2,8-dichloroquinoline (984 mg) and 4-(trifluoromethoxy)aniline (743 µL), Pd(OAc)$_2$ (22 mg), XantPhos (58 mg) and Cs$_2$CO$_3$ (4.6 g) in 20 mL of t-BuOH gave compound (90) (1.1 g).

$^1$H NMR (300 MHz, CDCl$_3$) δ 7.84 (d, J=9.1, 2H), 7.79 (d, J=8.9, 1H), 7.67 (dd, J=1.2, 7.6, 1H), 7.48 (dd, J=1.1, 8.0, 1H), 7.18 (s, 3H), 6.89 (s, 1H), 6.75 (d, J=8.9, 1H).

$^{13}$C NMR (75 MHz, CDCl$_3$) δ 153.88, 144.30, 143.91, 139.00, 138.25, 131.13, 130.13, 126.55, 125.42, 123.45, 122.50, 122.17, 120.49, 119.10, 113.24.

MS (ESI) [M+H]$^+$=339

Example 6

Compound (106) of the Table I

According to route (B), a mixture of 3-aminoquinoline (316 mg) and 2-chloro-3nitropyridine (315 mg), Pd(OAc)$_2$ (22 mg), XantPhos (58 mg) and Cs$_2$CO$_3$ (4.6 g) in 20 mL of t-BuOH gave compound (106) (374.1 mg).

$^1$H NMR (300 MHz, DMSO) δ 10.24 (s, 1H), 9.06 (d, J=2.3, 1H), 8.65 (d, J=1.8, 1H), 8.60 (d, J=8.3, 1H), 8.56 (d, J=4.5, 1H), 7.97 (dd, J=8.2, 14.4, 2H), 7.69 (t, J=6.9, 1H), 7.59 (t, J=7.4, 1H), 7.08 (dd, J=4.6, 8.3, 1H).

MS (ESI) [M+H]$^+$=267

Example 7

Compound (112) of the Table I

According to route (A), a mixture of 2,8-dichloroquinoline (958 mg) and aminopyrazine (522 mg), Pd(OAc)$_2$ (22 mg), XantPhos (58 mg) and Cs$_2$CO$_3$ (4.6 g) in 20 mL of t-BuOH gave compound (112) (728 mg).

$^1$H NMR (300 MHz, DMSO) δ 10.58 (s, 1H), 10.26 (s, 1H), 8.36 (s, 1H), 8.27 (s, 2H), 7.91-7.74 (m, 2H), 7.50 (d, J=8.8, 1H), 7.37 (t, J=7.6, 1H).

$^{13}$C NMR (75 MHz, DMSO) δ 152.94, 150.19, 142.48, 142.18, 138.20, 137.55, 135.74, 129.71, 126.99, 125.35, 123.84, 114.75.

MS (ESI) [M+H]$^+$=255

Example 7

Compound (136) of the Table I

According to route (A), a mixture of 2-chloroquinoxaline (82.0 mg) and 2-amino-4methylpyridine (59.4 mg), Pd(OAc)$_2$ (2.2 mg), XantPhos (5.8 mg) and Cs$_2$CO$_3$ (456 mg) in 2 mL of t-BuOH gave compound (136) (35.4 mg).

$^1$H NMR (300 MHz, CDCl$_3$) δ 9.02 (s, 1H), 8.70 (s, 1H), 8.30 (s, 1H), 8.20 (d, J=5.1, 1H), 7.94 (d, J=8.1, 1H), 7.84 (d, J=8.2, 1H), 7.64 (t, J=7.6, 1H), 7.49 (t, J=8.1, 1H), 6.83 (d, J=5.0, 1H), 2.43 (s, 3H).

$^{13}$C NMR (75 MHz, CDCl$_3$) δ 153.28, 150.20, 148.55, 147.40, 140.93, 139.83, 138.35, 130.44, 129.16, 127.18, 126.28, 119.70, 113.75, 21.87.

MS (ESI) [M+H]$^+$=237

Example 8

Method for Synthesizing the Compounds of the Present Invention

Typical Procedure for Pd-Catalysed Aminations

To a solution of halogeno compound (0.5 mmol, 1 equiv) in tert-butanol (2 mL) were added the amino moiety (0.55 mmol, 1.1 equiv), Cs$_2$CO$_3$ (456 mg, 1.4 mmol, 2.8 equiv), Xantphos (4,5-Bis(diphenylphosphino)-9,9-dimethylxanthene) (5.8 mg, 0.01 mmol, 2 mol %), Pd(OAc)$_2$ (2.2 mg, 0.01 mmol, 2 mol %). The reaction mixture was heated at 90° C. and stirred for 20 h under argon. The reaction mixture was concentrated under reduced pressure. The residue was purified by column chromatography on silica gel to yield pure compounds.

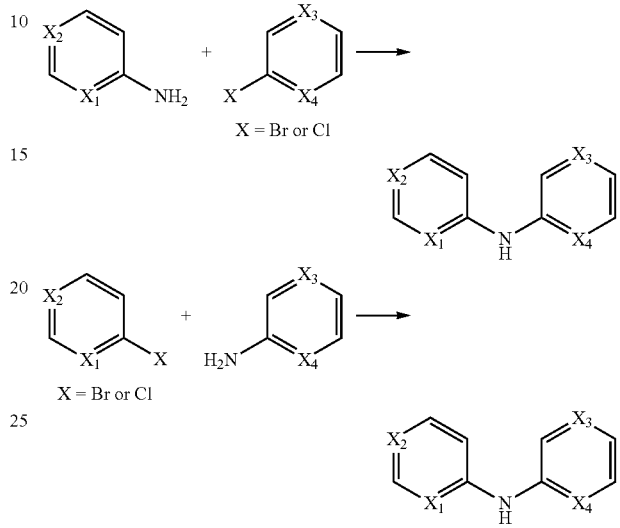

For example this procedure permitted to synthesize the following compounds:

Isoquinolin-5-yl-(3-methoxy-pyridin-2-yl)-amine $^1$H NMR (300 MHz, CDCl$_3$) δ 9.24 (s, 1H), 8.66 (dd, J=1.7, 6.8, 1H), 8.55 (d, J=6.0, 1H), 7.85 (d, J=5.0, 1H), 7.76 (d, J=6.0, 1H), 7.69-7.58 (m, 2H), 7.53 (s, 1H), 7.06 (d, J=7.7, 1H), 6.78 (dd, J=5.1, 7.8, 1H), 3.99 (s, 3H).

$^{13}$C NMR (75 MHz, CDCl$_3$) δ 153.23, 146.60, 142.97, 142.79, 138.53, 134.82, 129.53, 129.13, 127.95, 121.66, 119.82, 115.18, 115.05, 114.09, 100.15, 55.80.

(8-Chloro-quinolin-2-yl)-(4-methyl-pyridin-2-yl)-amine: (6) of the table I $^1$H NMR (300 MHz, CDCl3) δ 8.82 (s, 1H), 8.17 (d, J=5.1, 1H), 8.09 (s, 1H), 7.98 (d, J=8.9, 1H), 7.76 (dd, J=1.2, 7.6, 1H), 7.61 (dd, J=1.0, 8.0, 1H), 7.26 (t, J=7.8, 2H), 7.15 (d, J=8.7, 1H), 6.83 (d, J=5.0, 1H), 2.46 (s, 3H).

$^{13}$C NMR (75 MHz, CDCl3) δ 153.52, 153.14, 149.90, 147.43, 143.68, 138.08, 131.37, 129.98, 126.56, 125.58, 123.58, 119.17, 114.52, 114.02, 21.84.

(3-Methoxy-pyridin-2-yl)-quinolin-3-yl-amine: (10) of the table I $^1$H NMR (300 MHz, DMSO) δ 9.17 (d, J=2.5, 1H), 8.97 (d, J=2.4, 1H), 8.79 (s, 1H), 7.94-7.79 (m, 3H), 7.58-7.46 (m, 2H), 7.31 (d, J=7.9, 1H), 6.88 (dd, J=5.0, 7.9, 1H), 3.94 (s, 3H).

Pharmacological Data

The compounds of the invention have been the subject of pharmacological tests which have demonstrated their relevance as active substances in therapy and in particular for preventing, inhibiting or treating AIDS.

Example 9

Development of IDC16 Derivative Compounds

The inventors have shown that compound IDC16 (BAKKOUR et al., cited above, 2007) interacts functionally with the SF2/ASF complex and thus contributes to blocking alternative splicing during HIV replication, leading to the termination of the production of Tat protein.

Accordingly, the family of polycyclic indoles, to which compound IDC16 belongs, is known to exhibit the properties of DNA intercalating agents. Such compounds thus present a risk in terms of undesirable side effects.

The inventors thus sought to develop novel molecules exhibiting activity comparable to IDC16, in terms of activity inhibiting HIV splicing, but while not exhibiting the characteristics of DNA intercalating agents.

In their initial hypothesis, the inventors considered that the two polar heterocycles at the two ends of compound IDC16 were associated with its activity and that the two median rings were of less importance.

Based on this hypothesis, the inventors considered that:
the nitrogen of the indoline and of the D ring of IDC16 might act as acceptors of hydrogen bonds;
the N-methylated 4-pyridinone motif might be preserved in the analogues;
the flat tetracyclic geometry was not optimal and it might be wise to replace the B and C rings by other motifs to limit DNA intercalating properties.

Example 10

Inhibition of HIV-1 Production in Infected Peripheral Blood Mononuclear Cells (PBMCs)

Material and Methods

The first determination is that of the concentration of compound that exhibits the fewest side effects in terms of cell viability and progression of the cell cycle.

Within this framework, the peripheral blood mononuclear cells (PBMCs) of healthy donors are isolated by centrifugation on a FICOLL gradient. The cells are then cultivated to a density of $2.5 \times 10^6$ cells/ml with RPMI medium supplemented with 1% inactivated human AB serum, then incubated at 37° C., 5% $CO_2$ for an additional hour. The peripheral blood mononuclear cells are then recovered and cultivated for two days in RPMI medium supplemented with 10% fetal calf serum.

A standard experiment using 96 plates to test 30 molecules in triplicates including positive and negative controls, is performed as follows:

50 $10^6$ Ficoll purified PBMCs (10% DMSO 90% FCS) are washed with RPMI 10% FCS and resuspended in 25 ml of RPMI 10% FCS, glutamax containing 1000 U/ml of IL2 and 5 μg/ml PHA. The cells are then incubated for 3 days at 37° C. before to be washed with 50 ml PBS then with 50 ml RPMI 10% FCS. The cells are resuspended in 100 μl of RPMI 10% FCS containing 100 U/ml IL2 and seeded in 96 wells (1.5 $10^5$ cells/well). Viral infection is performed with 1 ng of AdaM/well. 100 μl of tested molecules at concentration of 10 μM are added to each well. Virus production is determined by p24 antigen immunosorbent assays after 3 and 6 days of infection (Kit Innogenetics). Typically PBMCs are prepared from several healthy donors (around 11 different donors). Dose response curves were then established with selected compounds to determine $IC_{50}$.

Protocol for Cytotoxicity:

To evaluate the cytotoxicity of different compounds we used the same protocol as above to seed the HOS-CD4$^+$-CCR5$^+$ cells or PBMCs in a final volume of 100 μl without adding the virus. After an incubation for 48 h at 37° C., the medium was removed and cells were incubated with 20 μl of CellTiter96 AqueousOne solution to determine the number of viable cells in proliferation and cytotoxicity assays (Promega). CellTiter96 AqueousOne is a colorimetric assay solution that has many advantages compared to MTT assays and gives us satisfactory results.

We have also evaluated the effect of selected molecules on CD4 and CD8 proliferation using the division tracking dye carboxyfluorescein diacetate succinimidyl ester (CFSE) (In vitrogen).

RESULTS

| Compound number | $IC_{50}$ in nM | Inhibition of p24 production in HIV infected PBMCs from different donors |
|---|---|---|
| Formula (Ia) | | |
| 1 | nd | 4 out 6 donnors |
| 6 | 0.1 | 9 out 14 donnors |
| 33 | nd | 5 out 6 donnors |
| 34 | nd | 6 out 8 donnors |
| 35 | nd | 6 out 8 donnors |
| 36 | nd | 6 out 8 donnors |
| 37 | nd | 4 out 6 donnors |
| 38 | nd | 4 out 6 donnors |
| 42 | nd | 4 out 6 donnors |
| 43 | 0.1 | 8 out of 10 donnors |
| 44 | nd | 4 out 6 donnors |
| 45 | nd | 4 out of 4 donnors |
| 46 | nd | 4 out of 4 donnors |
| 48 | nd | 4 out 4 donnors |
| 50 | nd | 4 out of 4 donnors |
| 64 | nd | 5 out of 5 donnors |
| 68 | nd | 4 out of 4 donnors |
| 69 | nd | 4 out of 4 donnors |
| 70 | nd | 4 out of 4 donnors |
| 71 | nd | 4 out of 4 donnors |
| 72 | nd | 4 out of 4 donnors |
| 73 | nd | 4 out of 4 donnors |
| 74 | nd | 4 out of 4 donnors |
| Formula (Ib) | | |
| 75 | nd | 6 out of 7 donnors |
| 77 | 0.05 | 11 out of 13 donnors |
| 78 | nd | 7 out of 8 donnors |
| 79 | nd | 7 out of 8 donnors |
| 80 | 1 | 7 out of 8 donnors |
| 81 | nd | 4 out of 4 donnors |
| 82 | nd | 4 out of 4 donnors |
| 86 | nd | 3 out of 4 donnors |
| 87 | nd | 4 out of 4 donnors |
| 88 | nd | 4 out of 4 donnors |
| 90 | 0.1 | 8 out of 10 donnors |
| 92 | nd | 3 out of 5 donnors |
| 96 | nd | 5 out of 6 donnors |
| 104 | nd | 4 out of 4 donnors |
| Formula (Ic) | | |
| 106 | 0.5 | 6 out of 6 donnors |
| Formula (Ie) | | |
| 109 | nd | 8 out of 8 donnors |
| 112 | 0.1 | 12 out of 13 donnors |
| Formula (Io) | | |
| 136 | nd | 6 out of 8 donnors |
| 139 | nd | 4 out of 4 donnors |
| 140 | nd | 4 out of 4 donnors |
| 141 | nd | 4 out of 4 donnors |

Example 11

Inhibition of HIV-1 Production in Infected Macrophages

In order to generalize the HIV-1 replication effect of the molecules of the present invention to other cell types, we examined various steps of the viral cycle in cells treated with the various drug at a concentration of 5 μM and submitted to one-round infection.

For such experiences, macrophages can be infected by the Ada-M R5 HIV strain and treated for 18 hours with various concentrations of the compounds of the present invention. The culture medium is then eliminated and the cells washed with an abundance of PBS. The cells are then cultivated under normal conditions. The culture medium and the cells are then collected at days 4, 7 and 14. Finally, virus replication is measured indirectly by determining the level of p24 antigen in both the culture supernatant and the cellular lysate by the ELISA method. In parallel, cell viability of the macrophages in the presence of the compounds of of the present invention is measured as before.

For this purpose, we exposed HOS-CD4$^+$-CCR5$^+$ cells to defective virions obtained by cotransfecting 293T cells with a plasmid encoding the R5 envelope of the AD8 strain and another plasmid containing the entire HIV-1 genome mutated in the envelope gene and harbouring a luciferase marker gene fused to nef (Connor R I, Chen B K, Choe S, Landau N R. (1995) Vpr is required for efficient replication of human immunodeficiency virus type-1 in mononuclear phagocytes. Virology 206: 935-944.). The amounts of luciferase activity in cells infected with these virions reflect both the number of integrated proviruses and expression of multiply spliced species encoding nef/luc. Two days post-infection, luciferase activity in HOS-CD4+-CCR5+ infected cells was measured.

The results are shown below:

| Compound | Results |
|---|---|
| 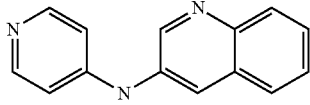 (121) of the table I | + |
| 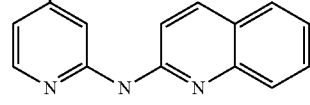 (2) of the table I | − |
| 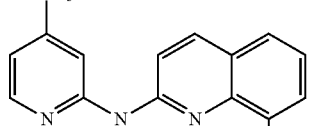 (6) of the table I | + |
| 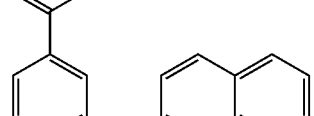 (5) of the table I | − |
| 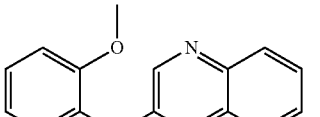 (10) of the table I | + |
| 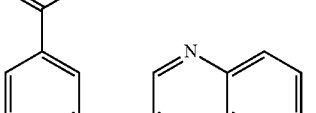 (14) of the table I | − |
| 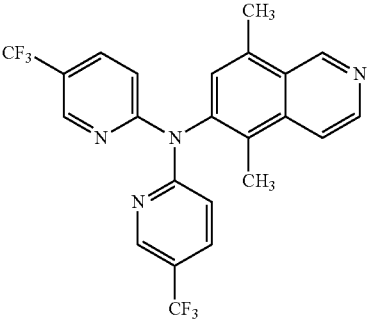 [SMILES: Cc1cc(N(c2ccc(C(F)(F)F)cn2)c2ccc(C(F)(F)F)cn2)c(C)c2ccncc12] | − |
| 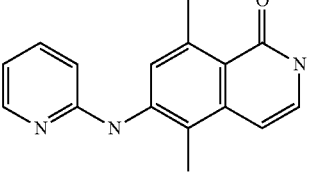 | − |
| 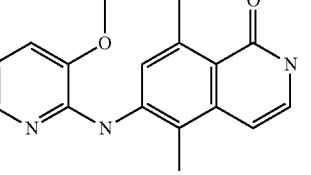 | − |
| 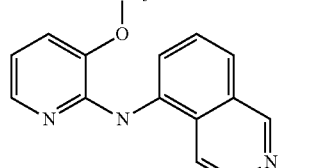 | + |
| 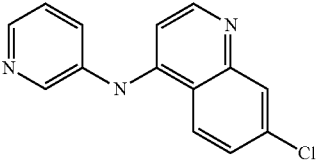 [SMILES: Clc1ccc2c(Nc3cccnc3)ccnc2c1] | − |

The results established that the compounds of the present invention show a luciferase inhibitory effect, thus showing that these compounds inhibit viral RNA splicing.

A further object of the invention consists of a pharmaceutical composition comprising at least one compound of formula (Ib) or (Ie) or anyone of compounds (8), (75), (77)-(84), (86)-(104), (109)-(117), (155)-(158) and their pharmaceutically acceptable salts, such as hydrobromide, tartrate, citrate, trifluoroacetate, ascorbate, hydrochloride, tartrate, triflate, maleate, mesylate, formate, acetate and fumarate and, optionally, a pharmaceutically acceptable support.

As examples of pharmaceutically acceptable supports, the composition can include emulsions, microemulsions, oil in water emulsions, anhydrous lipids and water in oil emulsions or other types of emulsions.

The inventive composition can further include one or more additives such as diluents, excipients, stabilizers and preservatives. Such additives are well known to those skilled in the art and are described notably in "*Ullmann's Encyclopedia of Industrial Chemistry, 6$^{th}$ Ed.*" (various editors, 1989-1998, Marcel Dekker) and in "*Pharmaceutical Dosage Forms and Drug Delivery Systems*" (ANSEL et al., 1994, WILLIAMS & WILKENS).

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

Still a further object consists of the use of at least one compound of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present invention in preparing a drug to treat, in a subject, a disease resulting from at least one splicing anomaly.

Therefore, the present invention relates to a compound of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present invention for preparing a drug to treat, in a subject, a disease resulting from at least one splicing anomaly.

As used in the present application, the term "subject" refers to a mammal such as a rodent, cat, dog, primate or human, preferably said subject is a human.

Preferably, the inventive compounds have the ability to inhibit pre-messenger RNA splicing processes that are either constitutive or, more specifically, dependent on regulating sequences known as an ESE (exonic splicing enhancer), ISE (intronic splicing enhancer), ESS (exonic splicing silencer) and ISS (intronic splicing silencer).

In a particularly preferred way, splicing processes are either constitutive and/or or dependent on ESE regulating sequences.

Preferably, the present invention relates to the use of the at least one compound of formula (I), (I), (Ia), (Ib), (Ic), (Id), (Ie), (If), (Ig), (Ih), (Ti), (Ij), (Ik), (Il), (Im), (Io), (Ip), (Iq), (Ir) or (Tee) as defined above, or one of its pharmaceutically acceptable salts according to the present invention, and more particularly of formula (Ia), (Ib), (Ic), (Ie) and (Io) as described above for preparing a drug to treat, in a subject, AIDS.

Therefore, the present invention relates to a one of said compounds, and more particularly to a compound (1) to (168) or one of its acceptable salts for treating AIDS.

Another object of the invention relates to a therapeutic method for treating a subject for a genetic disease resulting from splicing anomalies comprising the administration of a therapeutically effective quantity of a compound of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, more particularly of formula (Ia), (Ib), (Ic), (Ie) and (Io) as described above, and even more particularly of at least one compound (1) to (168) or one of its acceptable salts.

Preferably, said genetic disease resulting from splicing anomalies is AIDS.

A "therapeutically effective quantity" means a quantity that induces inhibition of the splicing of the pre-mRNAs of interest. Those skilled in the art will be able to determine said therapeutically effective quantity based on their general knowledge and on the methods described in the examples.

The compounds can be administered by any mode of administration such as, for example, by intramuscular, intravenous or oral route, etc.

In one embodiment according to the invention, said composition further includes an excipient making it possible to formulate the inventive compounds in such a way that said composition is provided in solid or liquid form to be prepared and administered by intravenous route.

The inventive compounds preferably will be administered by intravenous route at a concentration of 80-100 mg/m$^2$. The concentration will be chosen by those skilled in the art according to the organ or tissue to be treated, the state of advancement of the disease and the targeting mode used.

The invention claimed is:

1. A compound having the following formula or a pharmaceutically acceptable salt thereof:

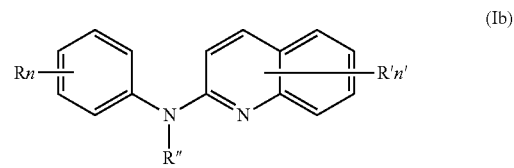

(Ib)

where:
R' is a hydrogen atom, a halogen atom, a ($C_1$-$C_3$)alkyl group, or a ($C_1$-$C_4$)alkoxy group, R" is a hydrogen atom or a ($C_1$-$C_4$)alkyl group, n is 1 or 2, and n' is 1 or 2;

when n is 1, then R is a ($C_1$-$C_3$) fluoroalkoxy group, a $NR_1R_2$ group or a phenoxy group, where $R_1$ and $R_2$ are independently a ($C_1$-$C_3$)group; and when n is 2, then one of the two R is a ($C_1$-$C_3$) fluoroalkoxy group and the other R is a ($C_1$-$C_3$)alkyl group.

2. A compound having the following formula or a pharmaceutically acceptable salt thereof:

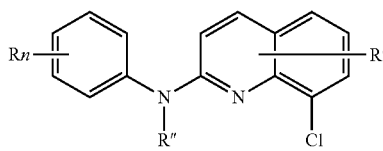

(Ib')

where:
- R independently represents a hydrogen atom, a halogen atom, a (C₁-C₃)alkyl group, a —NR₁R₂ group, a (C₁-C₃)fluoroalkoxy group, a —NO₂ group, a phenoxy group, or a (C₁-C₄)alkoxy group,
- R₁ and R₂ are independently a hydrogen atom or a (C₁-C₃)alkyl group,
- R' is a hydrogen atom, a halogen atom, a (C₁-C₃)alkyl group, or a (C₁-C₄)alkoxy group, with the proviso that R' is different from a methyl group at position 4 of the quinoline group,
- R" is a hydrogen atom or a (C₁-C₄)alkyl group,
- n is 1, 2, or 3, and
- n' is 1 or 2.

3. A compound having the following formula or a pharmaceutically acceptable salt thereof:

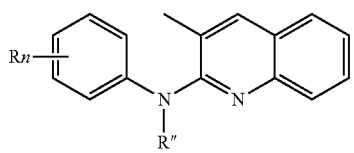

(Ib")

where:
- R independently represents a hydrogen atom, a halogen atom, a (C₁-C₃)alkyl group, a —NR₁R₂ group, a (C₁-C₃)fluoroalkoxy group, a —NO₂ group, a phenoxy group, or a (C₁-C₄)alkoxy group,
- R₁ and R₂ are independently a hydrogen atom or a (C₁-C₃)alkyl group,
- R" is a hydrogen atom or a (C₁-C₄)alkyl group,
- n is 1, 2, or 3, and
- n' is 1 or 2,
- with the proviso that when n is 1, R is not a hydrogen atom, a methyl group in para of the bond linked to NR", an ethoxy group in para of the bond linked to NR", nor a fluorine atom in para of the bond linked to NR".

4. A compound selected from the group consisting of:
(8) Quinolin-2-yl-(4-trifluoromethoxy-phenyl)-amine,
(75) 4-N-(8-chloroquinolin-2-yl)-1-N,1-N-dimethylbenzene-1,4-diamine,
(77) 8-chloro-N-(4-methoxyphenyl)quinolin-2-amine,
(78) 4-methyl-N-[4-(trifluoromethoxy)phenyl]quinolin-2-amine,
(79) N-(4-methoxyphenyl)-3-methylquinolin-2-amine,
(80) 3-methyl-N-[4-(trifluoromethoxy)phenyl]quinolin-2-amine,
(81) 1-N,1-N-dimethyl-4-N-(3-methylquinolin-2-yl)benzene-1,4-diamine,
(82) N-[2-methyl-4-(trifluoromethoxy)phenyl]quinolin-2-amine,
(83) N-[3-(trifluoromethoxy)phenyl]quinolin-2-amine,
(84) N-[2-(trifluoromethoxy)phenyl]quinolin-2-amine,
(86) N-(3-fluorophenyl)quinolin-2-amine,
(87) 8-chloro-N-[3-(trifluoromethoxy)phenyl]quinolin-2-amine,
(88) 8-chloro-N-(3-fluorophenyl)quinolin-2-amine,
(89) N-(4-(trifluoromethoxy)phenyl)quinolin-2-amine
(90) 8-chloro-N-[4-(trifluoromethoxy)phenyl]quinolin-2-amine,
(91) 3-methyl-N-[2-methyl-4-(trifluoromethoxy)phenyl]quinolin-2-amine,
(92) 3-methyl-N-[3-(trifluoromethoxy)phenyl]quinolin-2-amine,
(93) 3-methyl-N-[2-(trifluoromethoxy)phenyl]quinolin-2-amine,
(94) 8-chloro-N-[2-methyl-4-(trifluoromethoxy)phenyl]quinolin-2-amine,
(95) 3-methyl-N-(4-(trifluoromethoxy)phenyl)quinolin-2-amine
(96) 6-chloro-N-(4-(trifluoromethoxy)phenyl)quinolin-2-amine,
(97) 4-methyl-N-(4-(trifluoromethoxy)phenyl)quinolin-2-amine
(98) 8-bromo-N-[4-(trifluoromethoxy)phenyl]quinolin-2-amine,
(99) 8-fluoro-N-[4-(trifluoromethoxy)phenyl]quinolin-2-amine,
(100) 8-methyl-N-[4-(trifluoromethoxy)phenyl]quinolin-2-amine,
(101) N-(4-butoxyphenyl)-8-chloroquinolin-2-amine,
(102) N-(4-phenoxyphenyl)quinolin-2-amine,
(103) 8-methoxy-N-[4-(trifluoromethoxy)phenyl]quinolin-2-amine,
(104) 8-chloro-N-[3-chloro-4-(trifluoromethoxy)phenyl]quinolin-2-amine,
(155) N-(4-butoxyphenyl)-3-methylquinolin-2-amine,
(156) 4-N-(6-chloroquinolin-2-yl)-1-N,1-N-dimethylbenzene-1,4-diamine,
(157) 8-chloro-N-(3-chloro-4-methoxyphenyl)quinolin-2-amine,
(158) N1-(8-chloroquinolin-2-yl)-4-(trifluoromethoxy)benzene-1,2-diamine, and their pharmaceutically acceptable salts.

5. The compound of claim 4, wherein the pharmaceutically acceptable salts are selected from hydrobromide, tartrate, citrate, trifluoroacetate, ascorbate, hydrochloride, triflate, maleate, mesylate, formate, acetate, and fumarate.

6. A pharmaceutical composition comprising at least one compound as defined in claim 1.

7. A pharmaceutical composition comprising at least one compound as defined in claim 2.

8. A pharmaceutical composition comprising at least one compound as defined in claim 3.

9. A pharmaceutical composition comprising at least one compound as defined in claim 4.

10. A pharmaceutical composition comprising at least one compound as defined in claim 5.

11. The pharmaceutical composition according to claim 6, further comprising a pharmaceutically acceptable support.

12. The pharmaceutical composition according to claim 7, further comprising a pharmaceutically acceptable support.

13. The pharmaceutical composition according to claim 8, further comprising a pharmaceutically acceptable support.

14. The pharmaceutical composition according to claim 9, further comprising a pharmaceutically acceptable support.

15. The pharmaceutical composition according to claim 10, further comprising a pharmaceutically acceptable support.

16. A compound having the following formula or a pharmaceutically acceptable salt thereof:

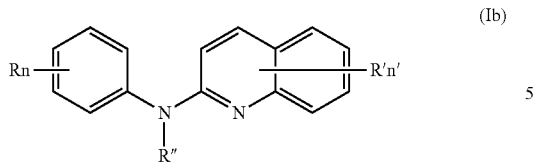

where:
- R independently represents a $(C_1$-$C_3)$fluoroalkoxy group,
- R' is a hydrogen atom, a halogen atom, a $(C_1$-$C_3)$alkyl group or a $(C_1$-$C_4)$alkoxy group,
- R" is a hydrogen atom or a $(C_1$-$C_4)$alkyl group,
- n is 1, and
- n' is 1 or 2.

17. A pharmaceutical composition comprising at least one compound as defined in claim 16.

18. The pharmaceutical composition according to claim 16, further comprising a pharmaceutically acceptable support.

\* \* \* \* \*

UNITED STATES PATENT AND TRADEMARK OFFICE
CERTIFICATE OF CORRECTION

PATENT NO. : 10,017,498 B2
APPLICATION NO. : 14/789250
DATED : July 10, 2018
INVENTOR(S) : Jamal Tazi et al.

It is certified that error appears in the above-identified patent and that said Letters Patent is hereby corrected as shown below:

In the Claims

In Claim 1 (Column 72, Line 62), change:
"$R_1$ and $R_2$ are independently a ($C_1$-$C_3$) group; and"
To:
--$R_1$ and $R_2$ are independently a ($C_1$-$C_3$)alkyl group; and--

Signed and Sealed this
Fourteenth Day of April, 2020

Andrei Iancu
*Director of the United States Patent and Trademark Office*